United States Patent
Lee et al.

(10) Patent No.: US 9,617,344 B2
(45) Date of Patent: Apr. 11, 2017

(54) FUSION PROTEIN COMPRISING TARGETING MOIETY, CLEAVAGE SITE, AND CELL MEMBRANE PENETRATING DOMAIN, AND USE THEREOF

(71) Applicant: Samsung Electronics Co., Ltd., Suwon-si, Gyeonggi-do (KR)

(72) Inventors: Jae Il Lee, Yongin-si (KR); Soshin Ahn, Seoul (KR); Jung Min Kim, Seoul (KR); Jungmin Lee, Seoul (KR); Jung-Hoon Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/794,542

(22) Filed: Jul. 8, 2015

(65) Prior Publication Data

US 2016/0008480 A1    Jan. 14, 2016

(30) Foreign Application Priority Data

Jul. 8, 2014    (KR) ........................ 10-2014-0085106

(51) Int. Cl.
| | | |
|---|---|---|
| *A61K 38/00* | (2006.01) | |
| *A61K 39/00* | (2006.01) | |
| *A61K 39/395* | (2006.01) | |
| *A61K 38/16* | (2006.01) | |
| *C12N 5/00* | (2006.01) | |
| *C12N 15/00* | (2006.01) | |
| *C07H 21/04* | (2006.01) | |
| *C07K 16/00* | (2006.01) | |
| *C12P 21/08* | (2006.01) | |
| *C07K 16/30* | (2006.01) | |
| *A61K 47/48* | (2006.01) | |
| *C07K 16/28* | (2006.01) | |

(52) U.S. Cl.
CPC ........ *C07K 16/30* (2013.01); *A61K 47/48569* (2013.01); *C07K 16/2863* (2013.01); *A61K 38/00* (2013.01); *C07K 2318/20* (2013.01); *C07K 2319/10* (2013.01); *C07K 2319/33* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 5,736,394 A * | 4/1998 | Coleman | ................ C07K 14/82 435/173.1 |
| 5,891,718 A * | 4/1999 | Hobart | ................. C12N 15/635 435/320.1 |
| 6,348,185 B1 | 2/2002 | Piwnica-Worms | |
| 8,043,855 B2 | 10/2011 | Aremendariz Borunda et al. | |
| 8,445,443 B2 | 5/2013 | Jo et al. | |
| 2004/0156827 A1 | 8/2004 | Aremendariz Borunda et al. | |
| 2012/0309934 A1 | 12/2012 | Jon et al. | |
| 2015/0030596 A1* | 1/2015 | Cheong | ................ C07K 14/705 424/134.1 |
| 2015/0119340 A1* | 4/2015 | Kim | ....................... C12N 15/87 514/21.3 |

FOREIGN PATENT DOCUMENTS

| | | |
|---|---|---|
| KR | 100887266 B1 | 2/2009 |
| KR | 1020120125455 A | 11/2012 |
| KR | 1020150053177 A | 5/2015 |

OTHER PUBLICATIONS

Kondo et al., "Highly efficient delivery of p16 antitumor peptide into aggressive leukemia/lymphoma cells using a novel transporter system", *Molecular Cancer Therapeutics*, 3(12): 1623-1630 (2004).
Kondo et al., "Potent synergy of dual antitumor peptides for growth suppression of human glioblastoma cell lines", *Molecular Cancer Therapeutics*, 7(6): 1461-1471 (2008).

* cited by examiner

*Primary Examiner* — Shulamith H Shafer
(74) *Attorney, Agent, or Firm* — Leydig, Voit & Mayer, Ltd.

(57) ABSTRACT

A fusion protein including a targeting moiety, a cleavage site, and a cell membrane penetrating domain, a conjugate including the fusion protein and a bioactive molecule, and methods employing the fusion protein and the conjugate are provided.

22 Claims, 14 Drawing Sheets

FIG. 8A

| Clone | NxC | N-Cap<br>D L G K K L L E A A R A G Q D D E V R I L M A N G A D V N A |
|---|---|---|
| E_01 | N3C | . . . . . . . . . . . . . . . . . . . . . . . . . . . . . . |
| E_67 | N3C | . . . . . . . . . . . . . . . . . . . . . . . . . . . . . . |
| E_68 | N3C | . . . . . . . . . . . . . . . . . . . . . . . . . . . . . . |
| E_69 | N4C | . . . . . . . . . . . . . . . . . . . . . . . . . . . . . . |
| 9_16 | N3C | . . . . . . . . . . . . . . . . . . . . . . . . . . . . . . |
| 9_26 | N3C | . . . . . . . . . . . . . . . . . . . . . . . . . . . . . . |
| 9_29 | N3C | . . . . . . . . . . . . . . . . . . . . . . . . . . . . . . |
| H_14 | N3C | . . . . . . . . . . . . . . . . C . . . . . . . . . . . . . |
| B4_01 | N4C | . . . . . . . . . . . . . . . H . . . . . . . . . . . . . . |
| B4_02 | N3C | . . . . . . . . . . . . . . . . . . . . . . . . . . . . . . |
| B4_07 | N3C | . . . . . . . . . . . . . . . . . . . . . . . . . . . . . . |
| B4_33 | N3C | . . . . . . . . . . . . . . . . . . . . . . . . . . . . . . |
| B4_45 | N3C | . . . . . . . . . . . . . . . . . . . . . . . . . . . . . . |
| B4_50 | N4C | . . . . . . . . . . . . . . . . . . . . . . . . . . . . . . |
| B4_58 | N5C | . . . . . . . . T . . . . . . . . . . . . . . . . . . . . . |
| L_01 | N3C | . . . . . . . . . . . . . . . . . . . . . . . . . . . . . . |
| L_02 | N2C | . . . . . . . . . . . . . . . . . . . . . . . . . . . . . . |
| L_07 | N2C | . . . . . . . . . . . . . . . . . . . . . . . . . . . . . . |
| L_11 | N3C | . . . . . . . . . . . . . . . . . . . . . . . . . . . . . . |
| L_13 | N2C | . . . . . . . . . . . . . . . . . . . . . . . . . . . . . . |
| L_19 | N3C | . . . . . . . . . . . . . . . . . . . . . . . . . . . . . . |
| T_01 | N3C | . . . . . . . . . . . . D . . . . . . . . . . . . . . . . . |
| T_02 | N3C | . . . . . . . V . . . . . . . . . . . . . . . . . . . . . . |
| T_07 | N3C | . . . . . . . . . . . . . . . . . . . . . . . . . . . . . . |
| T_08 | N3C | . . . . . . . . . . . . . . . . . . . . . . . . . . . . . . |
| T_09 | N3C | . . . . . . . . . . . . . S . . . . . . . . . . . . . . . . |
| T_16 | N3C | . . . . . P . . . . . . . . . . . . . . . . . . . . . . . . |
| T_25 | N3C | . . . . . . . . . . . . . . . . . . . . . . . . . . . . . . |
| T_27 | N3C | . . . . . P . . . . . . . . . . . . . . . . . . . . . . . . |
| T_37 | N3C | . . . . . . . . . . . . . . . . . . . . . . . . . . . . . . |
| T_40 | N3C | . . . . . . . . . . S . . . . . . . . . . . . . . . . . . . |

FIG. 8B

| | | L repeat | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Clone | NxC | x | D | x | x | G | x | T | P | L | H | L | A | A | x | x | G | H | L | E | I | V | E | V | L | L | K | z | G | A | D | V | N | A |
| E_01 | N3C | D | . | T | W | . | W | . | . | . | . | . | . | . | Y | Q | . | . | . | . | . | . | . | . | . | . | . | N | . | . | . | . | . | . |
| E_67 | N3C | T | . | N | D | . | N | . | . | . | . | . | S | . | W | I | . | . | . | . | . | . | . | . | . | . | . | H | . | . | . | . | . | . |
| E_68 | N3C | F | . | Y | W | . | M | . | . | . | . | . | . | . | D | N | . | . | . | . | . | . | . | . | . | . | . | H | . | . | . | . | . | . |
| E_69 | N4C | D | . | N | A | . | R | . | . | . | . | . | . | . | N | F | . | . | . | . | . | . | . | . | . | . | . | N | . | . | . | . | . | . |
| 9_16 | N3C | H | . | F | H | . | L | . | . | . | . | . | . | . | G | M | . | . | . | . | . | . | . | . | . | . | . | N | . | . | . | . | . | . |
| 9_26 | N3C | K | . | F | Y | . | I | . | . | . | . | . | . | . | A | Y | . | . | . | . | . | . | . | . | . | . | . | H | . | . | . | . | . | . |
| 9_29 | N3C | H | . | F | Y | . | I | . | . | . | . | . | . | . | N | F | . | . | . | . | . | . | . | . | . | . | . | H | . | . | . | . | . | . |
| H_14 | N3C | T | . | I | H | . | H | . | . | . | . | . | . | . | A | M | . | . | . | . | . | . | . | . | . | . | . | N | . | . | . | . | . | . |
| B4_01 | N4C | V | . | W | M | . | D | . | . | . | . | . | . | . | F | Y | . | . | . | . | . | . | . | . | . | . | . | N | . | . | . | . | . | . |
| B4_02 | N3C | K | . | N | A | . | K | . | A | . | . | . | . | . | V | W | . | . | . | . | . | . | . | . | . | . | . | N | . | . | . | . | . | . |
| B4_07 | N3C | R | . | V | F | . | W | . | . | . | . | . | . | . | V | D | . | . | . | . | . | . | . | . | . | . | . | Y | . | . | . | . | . | . |
| B4_33 | N3C | E | . | A | T | . | F | . | . | . | . | . | . | . | V | W | . | . | . | . | . | . | . | . | . | . | . | N | . | . | . | . | . | . |
| B4_45 | N3C | R | . | D | G | . | T | . | . | . | . | . | . | . | N | H | . | . | . | . | . | . | . | . | . | . | . | Y | . | . | . | . | . | . |
| B4_50 | N4C | H | . | R | Y | . | V | . | . | . | . | . | . | . | Y | F | . | . | . | . | . | . | . | . | . | . | . | N | . | . | . | . | . | . |
| B4_58 | N5C | F | . | S | N | . | I | . | . | . | . | . | . | . | F | F | . | . | . | . | . | . | . | . | . | . | . | N | . | . | . | . | . | . |
| L_01 | N3C | N | . | I | S | . | Y | . | . | . | . | . | . | . | Y | V | . | . | Q | . | . | . | . | . | . | . | . | N | . | . | . | . | . | . |
| L_02 | N2C | R | . | M | S | . | Y | . | . | . | . | . | . | . | H | M | . | . | . | . | . | . | . | . | . | . | . | N | . | . | . | . | . | . |
| L_07 | N2C | S | . | K | S | . | Y | . | . | . | . | . | . | . | H | I | . | . | . | . | . | . | . | . | . | . | . | H | . | . | . | . | . | . |
| L_11 | N3C | I | . | T | I | . | L | . | . | . | . | . | . | . | H | D | . | . | . | . | . | . | . | . | . | . | . | N | . | . | . | . | . | . |
| L_13 | N2C | F | . | M | S | . | Y | . | . | . | . | . | . | . | Y | D | . | . | . | . | . | . | . | . | . | . | . | N | . | . | . | . | . | . |
| L_19 | N3C | D | . | N | K | . | D | . | . | . | . | . | . | . | S | F | . | . | . | . | . | . | . | . | . | . | . | N | . | . | . | . | . | . |
| T_01 | N3C | N | . | I | W | . | I | . | . | . | . | . | . | . | I | F | . | . | . | . | . | . | . | . | . | F | . | . | N | . | . | . | . | . | . |
| T_02 | N3C | A | . | H | Q | S | F | . | . | . | . | Y | . | I | F | . | . | . | . | . | . | . | . | . | . | . | . | N | . | . | . | . | . | . |
| T_07 | N3C | Y | . | W | K | . | L | . | . | . | . | . | . | . | I | F | . | . | . | . | . | . | . | S | A | M | . | N | . | . | . | . | . | . |
| T_08 | N3C | W | . | F | L | . | L | I | . | . | R | . | . | . | A | F | . | . | . | . | . | . | . | . | . | . | . | N | . | . | . | . | . | . |
| T_09 | N3C | N | . | F | Q | . | I | . | . | . | . | . | . | . | I | F | . | . | . | . | . | . | . | . | . | . | . | N | . | . | . | . | . | . |
| T_16 | N3C | Y | . | I | V | . | I | . | . | . | . | . | . | . | I | F | . | . | . | . | . | . | . | . | . | . | . | N | . | . | . | . | . | . |
| T_25 | N3C | D | . | R | R | . | I | P | . | . | . | . | . | . | I | F | . | . | . | . | . | . | . | . | . | . | . | H | . | . | . | . | . | . |
| T_27 | N3C | Y | . | R | H | . | L | . | . | . | . | V | . | I | F | . | . | . | . | . | . | . | . | . | . | . | . | H | . | . | . | . | . | . |
| T_37 | N3C | H | . | K | R | . | I | . | . | . | . | . | . | . | I | T | . | . | . | . | M | . | . | . | . | . | . | H | . | . | . | . | . | . |
| T_40 | N3C | N | . | R | V | . | F | . | . | . | . | . | . | . | M | F | . | . | . | . | . | L | . | . | . | . | . | N | . | . | . | . | . | . |

FIG. 8C

| Clone | NxC | x | D | x | x | G | x | T | P | L | H | L | A | A | x | x | G | H | L | E | I | V | E | V | L | L | K | z | G | A | D | V | N | A |
|---|---|---|---|---|---|---|---|---|---|---|---|---|---|---|---|---|---|---|---|---|---|---|---|---|---|---|---|---|---|---|---|---|---|---|
| E_01 | N3C | Y | . | Y | I | . | W | . | . | . | . | . | . | . | D | . | . | . | . | . | . | . | . | . | . | . | . | N | . | . | . | . | . | . |
| E_67 | N3C | D | . | L | L | . | M | . | . | . | . | . | . | . | D | T | . | . | . | . | . | . | . | . | . | . | . | Y | . | . | . | . | . | . |
| E_68 | N3C | S | . | N | F | . | F | . | . | . | . | . | . | . | F | Y | . | . | . | . | . | . | . | . | . | . | . | H | . | . | . | . | . | . |
| E_69 | N4C | K | G | H | H | C | N | . | . | . | . | . | . | . | W | A | . | . | . | . | . | . | . | . | . | . | . | Y | . | . | . | . | . | . |
| 9_16 | N3C | V | . | T | D | . | I | . | L | . | . | . | . | . | Y | Y | . | . | . | . | . | . | . | . | . | . | . | H | . | . | . | . | . | . |
| 9_26 | N3C | H | . | W | N | . | W | . | . | . | . | . | . | . | K | Y | . | . | . | . | . | . | . | . | . | . | . | H | . | . | . | . | . | . |
| 9_39 | N3C | F | . | Y | . | D | N | . | . | . | . | . | . | . | D | A | . | . | . | . | . | . | . | . | . | . | . | Y | . | . | . | . | . | . |
| H_14 | N3C | N | . | W | R | . | F | . | . | . | . | . | . | . | L | N | . | . | . | . | . | . | . | . | . | . | . | N | . | . | . | . | . | . |
| B4_01 | N4C | K | . | T | W | . | D | . | . | . | . | . | . | . | L | L | . | R | . | . | . | . | . | . | . | . | . | H | . | . | . | . | . | . |
| B4_02 | N3C | Y | . | A | S | . | Y | . | L | . | . | . | . | . | R | M | . | . | . | . | . | . | . | . | . | . | . | Y | . | . | . | . | . | . |
| B4_07 | N3C | R | . | V | A | . | R | . | . | . | . | . | . | . | S | F | . | . | . | . | . | . | . | . | . | . | . | Y | . | . | . | . | . | . |
| B4_33 | N3C | N | . | Q | Y | . | Y | . | . | . | . | . | . | . | R | M | . | . | . | . | . | . | . | . | . | . | . | H | . | . | . | . | . | . |
| B4_45 | N3C | N | . | R | Y | . | Y | . | T | . | . | . | . | . | R | H | . | . | . | . | . | . | . | . | . | . | . | H | . | . | . | . | . | . |
| B4_50 | N4C | D | . | H | D | . | Y | . | . | . | . | . | . | . | D | K | . | . | . | . | . | . | . | . | . | . | . | H | . | . | . | . | . | . |
| B4_58 | N5C | H | . | S | Y | . | S | . | . | . | . | . | . | . | N | R | . | . | . | . | . | . | . | . | . | . | . | Y | . | . | . | . | . | . |
| L_01 | N3C | D | . | T | W | . | D | . | . | . | . | . | . | . | L | F | . | . | . | . | . | . | . | . | . | . | . | Y | . | . | . | . | . | . |
| L_02 | N2C | K | . | N | W | . | D | . | . | . | . | . | . | . | I | F | . | . | . | . | . | . | . | . | . | . | . | N | . | . | . | . | . | . |
| L_07 | N2C | H | . | S | W | . | D | . | . | . | . | . | . | . | T | F | . | . | . | . | . | . | . | . | . | . | . | H | . | . | . | . | . | . |
| L_11 | N3C | A | . | N | W | . | I | . | . | . | . | . | . | . | R | R | . | . | . | . | . | . | . | . | . | . | . | H | . | . | . | . | . | . |
| L_13 | N2C | N | . | L | W | . | D | . | . | . | . | . | . | . | T | R | . | . | . | . | . | . | . | . | . | . | . | Y | . | . | . | . | . | . |
| L_19 | N3C | D | . | Y | F | . | D | . | . | . | . | . | . | . | W | S | . | . | . | . | . | . | . | . | . | . | . | Y | . | . | . | . | . | . |
| T_01 | N3C | S | . | F | S | . | F | . | . | . | . | . | . | . | Y | K | . | . | . | . | . | . | . | . | . | . | . | H | . | . | . | . | . | . |
| T_02 | N3C | S | . | W | H | . | N | . | . | . | . | . | . | . | W | I | . | . | . | . | . | . | . | . | . | . | . | Y | . | . | . | . | . | . |
| T_07 | N3C | I | . | F | S | . | R | . | . | . | . | . | . | . | L | I | . | . | . | . | . | . | . | . | . | . | . | Y | . | . | . | . | . | . |
| T_08 | N3C | K | . | T | Y | . | I | . | . | . | . | . | . | . | M | N | . | . | . | . | . | . | . | . | . | . | . | N | . | . | . | . | . | . |
| T_09 | N3C | Y | . | Q | M | . | M | . | . | . | . | . | . | . | W | T | . | . | . | . | . | . | . | . | . | . | . | H | . | . | . | . | . | . |
| T_16 | N3C | Y | . | M | Q | V | N | . | . | . | . | . | . | . | W | L | . | . | . | . | . | . | . | . | . | . | . | N | . | . | . | . | . | . |
| T_25 | N3C | H | . | M | Q | . | R | . | . | . | . | . | . | . | Y | T | . | . | . | . | . | . | . | . | . | . | . | Y | . | . | . | . | . | . |
| T_27 | N3C | I | . | I | I | . | Y | . | . | . | . | . | . | . | W | S | . | . | . | . | . | . | . | . | . | . | . | N | . | . | . | . | . | . |
| T_37 | N3C | V | . | I | Q | . | R | . | . | . | . | . | . | . | W | I | . | . | . | . | . | . | . | . | . | . | . | Y | . | . | . | . | . | . |
| T_40 | N3C | I | . | F | Q | . | K | . | . | . | . | . | . | . | Q | L | . | . | . | . | . | . | . | . | . | . | . | Y | . | . | . | . | . | . |

2. repeat

FIG. 8D

| Clone | NxC | x | D | x | x | G | x | T P L H L A A | x | x | G H L E I V E V L L K | z | G A D V N A |
|---|---|---|---|---|---|---|---|---|---|---|---|---|---|
| | | | | | | | | 3. repeat | | | | | |
| E_01 | N3C | S | D | Y | I | G | D | T P L H L A A | H | N | G H L E I V E V L L K | H | G A D V N A |
| E_67 | N3C | R | D | T | R | G | K | T P L H L A A | R | D | G H L E I V E V L L K | H D | G A D V N A |
| E_68 | N3C | F | D | M | W | G | N | T P L H L A A | Q | N | G H L E I V E V L L K | N | G A D V N A |
| E_69 | N4C | D | D | D | E | G | Y | T P L H L A A | D | I | G H L E I V E V L L K . D | Y | G A D V N A |
| 9_16 | N3C | H | D | Y | A | G | S | T P L H L A A | N | T | G H L E I V E V L L K | N | G A D V N A |
| 9_26 | N3C | I | D | N | A | G | K | T P L H L A A | A | H | G H L E I V E V L L K | Y | G A D V N A |
| 9_29 | N3C | S | D | R | D | G | H | T P L H L A A | R | E | G H L E I V E V L L K | N | G A D V N A |
| H_14 | N3C | T | D | T | A | G | N | T P L H L A A | W | F | G H L E I V E V L L K | N | G A D V N A |
| B4_01 | N4C | I | D | M | R | G | T | T P L H L A A | P | A | G H L E I V E V L L K | Y | G A D V N A |
| B4_02 | N3C | R | D | R | F | G | S | T P L H L A A | W | H | G H L E I V E V L L K | H | G A D V N A |
| B4_07 | N3C | V | D | Y | T | G | T | T P L H L A A | W | H | G H L E I V E V L L K | H | G A D V N A |
| B4_33 | N3C | I | D | V | L | G | T | T P L H L A A | W | H | G H L E I V E V L L K | N | G A D V N A |
| B4_45 | N3C | F | D | N | T | G | Q | T P L H L A A | W | H | G H L E I V E V L L K | Y | G A D V N A |
| B4_50 | N4C | D | D | S | M | G | N | T P L H L A A | R | H | G H L E I V E V L L K | H | G A D V N A |
| B4_58 | N5C | F | D | S | T | G | Q | T P L H L A A | S | Q | G H L E I V E V L L K | Y | G A D V N A |
| L_01 | N3C | H | D | R | F | G | F | T P L H L A A | S | S | G H L E I V E V L L K | H | G A D V N A |
| L_02 | N2C | | | | | | | | | | | | |
| L_07 | N2C | | | | | | | | | | | | |
| L_11 | N3C | D | D | V | Q | G | N | T P L H L A A . T | H | H | G H L E I V E V L L K | H | G A D V N A |
| L_13 | N2C | | | | | | | | | | | | |
| L_19 | N3C | Q | D | Q | R | G | F | T P L H L A A | I | A | G H L E I V E V L L K | Y | G A D V N A |
| T_01 | N3C | N | D | A | T | G | T | T P L H L A A | K | K | G H L E I V E V L L K | N | G A D V N A |
| T_02 | N3C | T | D | H | S | G | S | T P L H L A A | T | L | G H L E I V E V L L K | Y | G A D V N A |
| T_07 | N3C | H | D | S | A | G | S | T P L H L A A | T | K | G H L E I V E V L L K | Y | G A D V N A |
| T_08 | N3C | L | D | N | T | G | S | T P L H L A A | N | Y | G H L E I V E V L L K | H | G A D V N A |
| T_09 | N3C | D | D | T | H | G | A | T P L H L A A | H | T | G H L E I V E V L L K | Y | G A D V N A |
| T_16 | N3C | E | D | S | Y | G | N | T P L H L A A | D | K | G H L E I V E V L L K | N | G A D V N A |
| T_25 | N3C | I | D | F | T | G | H | T P L H L A A | F | R | G H L E I V E V L L K | H | G A D V N A |
| T_27 | N3C | S | D | V | T | G | S | T P L H L A A | D | K | G H L E I V E V L L K | Y | G A D V N A |
| T_37 | N3C | M | D | D | F | G | E | T P L H L A A | R | T | G H L E I V E V L L K | H | G A D V N A |
| T_40 | N3C | L | D | A | R | G | I | T P L H L A A | I | H | G H L E I V E V L L K . p | Y | G A D V N A |

FIG. 8E

4. repeat

| Clone | NxC | x | D | x | x | G | x | T | P | L | H | L | A | A | x | x | G | H | L | E | I | V | E | V | L | L | K | z | G | A | D | V | N | A |
|---|---|---|---|---|---|---|---|---|---|---|---|---|---|---|---|---|---|---|---|---|---|---|---|---|---|---|---|---|---|---|---|---|---|---|
| E_01 | N3C | | | | | | | | | | | | | | | | | | | | | | | | | | | | | | | | | |
| E_67 | N3C | | | | | | | | | | | | | | | | | | | | | | | | | | | | | | | | | |
| E_68 | N3C | | | | | | | | | | | | | | | | | | | | | | | | | | | | | | | | | |
| E_69 | N4C | W | . | M Y | . | R | . | . | . | . | . | . | . | . | S A | . | . | . | . | . | . | . | . | . | . | . | . | Y | . | . | . | . | . | . |
| 9_16 | N3C | | | | | | | | | | | | | | | | | | | | | | | | | | | | | | | | | |
| 9_26 | N3C | | | | | | | | | | | | | | | | | | | | | | | | | | | | | | | | | |
| 9_29 | N3C | | | | | | | | | | | | | | | | | | | | | | | | | | | | | | | | | |
| H_14 | N3C | | | | | | | | | | | | | | | | | | | | | | | | | | | | | | | | | |
| B4_01 | N4C | D | . | V H | . | N | . | . | . | . | . | . | . | . | M S | . | . | . | . | . | . | . | . | . | . | . | . | Y | . | . | . | . | . | . |
| B4_02 | N3C | | | | | | | | | | | | | | | | | | | | | | | | | | | | | | | | | |
| B4_07 | N3C | | | | | | | | | | | | | | | | | | | | | | | | | | | | | | | | | |
| B4_33 | N3C | | | | | | | | | | | | | | | | | | | | | | | | | | | | | | | | | |
| B4_45 | N3C | | | | | | | | | | | | | | | | | | | | | | | | | | | | | | | | | |
| B4_50 | N4C | N | . | F M | . | S | . | . | . | . | . | . | . | . | W S | . | . | . | . | . | . | . | . | . | . | . | . | H | . | . | . | . | . | . |
| B4_58 | N5C | S | . | R M | . | F | . | . | . | . | . | . | . | . | Y T | . | . | . | . | . | . | . | . | . | . | . | . | N | . | . | . | . | . | . |
| L_01 | N3C | | | | | | | | | | | | | | | | | | | | | | | | | | | | | | | | | |
| L_02 | N2C | | | | | | | | | | | | | | | | | | | | | | | | | | | | | | | | | |
| L_07 | N2C | | | | | | | | | | | | | | | | | | | | | | | | | | | | | | | | | |
| L_11 | N3C | | | | | | | | | | | | | | | | | | | | | | | | | | | | | | | | | |
| L_13 | N2C | | | | | | | | | | | | | | | | | | | | | | | | | | | | | | | | | |
| L_19 | N3C | | | | | | | | | | | | | | | | | | | | | | | | | | | | | | | | | |
| T_01 | N3C | | | | | | | | | | | | | | | | | | | | | | | | | | | | | | | | | |
| T_02 | N3C | | | | | | | | | | | | | | | | | | | | | | | | | | | | | | | | | |
| T_07 | N3C | | | | | | | | | | | | | | | | | | | | | | | | | | | | | | | | | |
| T_08 | N3C | | | | | | | | | | | | | | | | | | | | | | | | | | | | | | | | | |
| T_09 | N3C | | | | | | | | | | | | | | | | | | | | | | | | | | | | | | | | | |
| T_16 | N3C | | | | | | | | | | | | | | | | | | | | | | | | | | | | | | | | | |
| T_25 | N3C | | | | | | | | | | | | | | | | | | | | | | | | | | | | | | | | | |
| T_27 | N3C | | | | | | | | | | | | | | | | | | | | | | | | | | | | | | | | | |
| T_37 | N3C | | | | | | | | | | | | | | | | | | | | | | | | | | | | | | | | | |
| T_40 | N3C | | | | | | | | | | | | | | | | | | | | | | | | | | | | | | | | | |

FIG. 8F

| Clone | NxC | x | D | x | x | G | x | T P L H L A A | x | x | G H L E I V E V L L K | z | G A D V N A |
|---|---|---|---|---|---|---|---|---|---|---|---|---|---|
| E_01 | N3C | | | | | | | | | | | | |
| E_67 | N3C | | | | | | | | | | | | |
| E_68 | N3C | | | | | | | | | | | | |
| E_69 | N4C | | | | | | | | | | | | |
| 9_16 | N3C | | | | | | | | | | | | |
| 9_26 | N3C | | | | | | | | | | | | |
| 9_29 | N3C | | | | | | | | | | | | |
| H_14 | N3C | | | | | | | | | | | | |
| B4_01 | N4C | | | | | | | | | | | | |
| B4_02 | N3C | | | | | | | | | | | | |
| B4_07 | N3C | | | | | | | | | | | | |
| B4_33 | N3C | | | | | | | | | | | | |
| B4_45 | N3C | | | | | | | | | | | | |
| B4_50 | N4C | | | | | | | | | | | | |
| B4_58 | N5C | K | | F | V | | W | | Y | R | | H | |
| L_01 | N3C | | | | | | | | | | | | |
| L_02 | N2C | | | | | | | | | | | | |
| L_07 | N2C | | | | | | | | | | | | |
| L_11 | N3C | | | | | | | | | | | | |
| L_13 | N2C | | | | | | | | | | | | |
| L_19 | N3C | | | | | | | | | | | | |
| T_01 | N3C | | | | | | | | | | | | |
| T_02 | N3C | | | | | | | | | | | | |
| T_07 | N3C | | | | | | | | | | | | |
| T_08 | N3C | | | | | | | | | | | | |
| T_09 | N3C | | | | | | | | | | | | |
| T_16 | N3C | | | | | | | | | | | | |
| T_25 | N3C | | | | | | | | | | | | |
| T_27 | N3C | | | | | | | | | | | | |
| T_37 | N3C | | | | | | | | | | | | |
| T_40 | N3C | | | | | | | | | | | | |

FIG. 8G

| Clone | NxC | C-Cap<br>Q D K F G K T A F D I S I D N G N E D L A E I L Q |
|---|---|---|
| E_01 | N3C | . . . . . . . . . . . . . . . . . . . . . . . . . . |
| E_67 | N3C | . . . . . . . . . . . . . . . . . . . . . . . . . . |
| E_68 | N3C | . . . . . . . . . . . . . . . . . . . . . . . . . . |
| E_69 | N4C | . . . . . . . . . . . . . . . . . . . . . . . . . . |
| 9_16 | N3C | . . . . . . . . . . . . . . . . . . . . . . . . . . |
| 9_26 | N3C | . . . . . . . . . . . . . . . . . . . . . . . . . . |
| 9_29 | N3C | . . . . . . . . . . . . . . . . . . . . . . . . . . |
| H_14 | N3C | . . . . . . . . . . . . . . . . . . . . . . . . . . |
| B4_01 | N4C | . . . . . . . . . . . . . . . . . . . . . . . . . . |
| B4_02 | N3C | . . . . . . . . . . . . . . . . . . . . . . . . . . |
| B4_07 | N3C | . . . . . . . . . . . . . . . . . . . . . . . . . . |
| B4_33 | N3C | . . . . . . . . . . . . . . . . . . . . . . . . . . |
| B4_45 | N3C | . . . . . . . . . . . . . . . . . . . . . . . . . . |
| B4_50 | N4C | . . . . . . . . . . . . . . . . . . . . . . . . . . |
| B4_58 | N5C | . . . . . . . . . . . . . . . . . . . . . . . . . . |
| L_01 | N3C | . . . . . . . . . . . . . . . . . . . . . . . . . . |
| L_02 | N2C | . . . . . . . . . . . . . . . . . . . . . . . . . . |
| L_07 | N2C | . . . . . . . . . . . . . . . . . . . . . . . . . . |
| L_11 | N3C | . . . . . . . . . . . . . . . . . . . . . . . . . . |
| L_13 | N2C | . . . . . . . . . . . . . . . . . . . . . . . . . . |
| L_19 | N3C | . . . . . . . . . . . . . . . . . . . . . . . . . . |
| T_01 | N3C | . . . . . . . . . . . . . . . . . . . . . . . . . . |
| T_02 | N3C | . . . . . . . . . . . . . . . . . . . . . . . . . . |
| T_07 | N3C | . . . . . . . . . . . . . . . . . . . . . . . . . . |
| T_08 | N3C | . . . . . . . . . . . . . . . . . . . . . . . . . . |
| T_09 | N3C | . . . . . . . . . . . . . . . . . . . . . . . . . . |
| T_16 | N3C | . . . . . . . . . . . . . . . . . . . . . . . . . . |
| T_25 | N3C | . . . . . . . . . . . . . . . . . . . . . . . . . . |
| T_27 | N3C | . . . . . . . . . . . . . . . . . . . . . . . . . . |
| T_37 | N3C | . . . . . . . . . . . . . . . . . . . . . . . . . . |
| T_40 | N3C | . . . . . . . . . . . . . . . . . . . . . . . . . . |

SEQUENCE LISTING

```
<160> NUMBER OF SEQ ID NOS: 85

<210> SEQ ID NO 1
<211> LENGTH: 156
<212> TYPE: PRT
<213> ORGANISM: Artificial Sequence
<220> FEATURE:
<223> OTHER INFORMATION: Synthetic Wild-Type Human p16

<400> SEQUENCE: 1

Met Glu Pro Ala Ala Gly Ser Ser Met Glu Pro Ser Ala Asp Trp Leu
 1               5                  10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Ala Gly Gly Thr Arg Gly Ser Asn His Ala Arg
    130                 135                 140
```

```
Ile Asp Ala Ala Glu Gly Pro Ser Asp Ile Pro Asp
145                 150                 155

<210> SEQ ID NO 2
<211> LENGTH: 156
<212> TYPE: PRT
<213> ORGANISM: Artificial Sequence
<220> FEATURE:
<223> OTHER INFORMATION: Synthetic Human p16 Variant

<400> SEQUENCE: 2

Met Glu Pro Ala Ala Gly Ser Ser Met Glu Pro Ser Ala Asp Lys Leu
 1               5                  10                  15

Ala Thr Ala Ala Ala Arg Gly Arg Val Glu Val Arg Ala Leu Leu
             20                  25                  30

Glu Ala Gly Ala Asp Pro Asn Ala Pro Asn Ser Tyr Gly Arg Arg Pro
         35                  40                  45

Ile Gln Val Met Met Met Gly Ser Ala Arg Val Ala Glu Leu Leu Leu
     50                  55                  60

Lys His Gly Ala Glu Pro Asn Ser Ala Asp Pro Ala Thr Ser Thr Arg
65                  70                  75                  80

Pro Val His Asp Ala Ala Arg Glu Gly Phe Leu Asp Thr Leu Val Val
                 85                  90                  95

Leu His Arg Ala Gly Ala Arg Leu Asp Ala Arg Asp Ala Trp Gly Arg
            100                 105                 110

Thr Pro Val Asp Leu Ala Glu Glu Leu Gly His Arg Asp Val Ala Arg
        115                 120                 125

Tyr Leu Arg Ala Ala Ala Gly Gly Thr Arg Gly Ser Asn His Ala Arg
    130                 135                 140

Ile Asp Ala Ala Glu Gly Pro Ser Asp Ile Pro Asp
145                 150                 155

<210> SEQ ID NO 3
<211> LENGTH: 468
<212> TYPE: DNA
<213> ORGANISM: Artificial Sequence
<220> FEATURE:
<223> OTHER INFORMATION: Synthetic human p16 variant coding DNA

<400> SEQUENCE: 3
atggaaccgg ctgctggcag ctctatggaa ccgtctgctg acaaactggc taccgctgct      60
gctcgtggtc gtgttgaaga agttcgtgct ctgctggaag ctggtgctga tccgaacgct     120
ccgaactctt acggtcgtcg tccgatccag gttatgatga tgggcagcgc tcgtgttgct     180
gaactgctgc tgaaacacgg tgctgaaccg aacagcgctg accoggctac cagcaccogt     240 ccggttcacg acgctgctcg tgaaggtttc ctggacaccc tggttgttct gcaccgtgct     300
ggtgctcgtc tggacgcgcg tgacgcttgg ggtcgtaccc cggttgacct ggctgaagaa     360
ctgggtcacc gtgacgttgc tcgttacctg cgtgctgctg ctggtggtac ccgtggcagc     420
aaccacgctc gtatcgacgc tgctgaaggt ccgtctgaca tcccggac                  468

<210> SEQ ID NO 4
<211> LENGTH: 471
<212> TYPE: DNA
<213> ORGANISM: Artificial Sequence
<220> FEATURE:
<223> OTHER INFORMATION: Synthetic wild-type human p16 protein coding
      DNA
```

-continued

<400> SEQUENCE: 4

```
atggagccgg cggcggggag cagcatggag ccttcggctg actggctggc cacggccgcg    60
gcccggggtc gggtagagga ggtgcgggcg ctgctggagg cggggcgct gcccaacgca    120
ccgaatagtt acggtcggag gccgatccag gtcatgatga tgggcagcgc ccgagtggcg    180
gagctgctgc tgctccacgg cgcggagccc aactgcgccg accccgccac tctcacccga    240
cccgtgcacg acgctgcccg ggagggcttc ctggacacgc tggtggtgct gcaccgggcc    300
ggggcgcggc tggacgtgcg cgatgcctgg ggccgtctgc ccgtggacct ggctgaggag    360
ctgggccatc gcgatgtcgc acggtacctg cgcgcggctg cgggggggcac cagaggcagt    420
aaccatgccc gcatagatgc cgcggaaggt ccctcagaca tccccgattg a             471
```

<210> SEQ ID NO 5
<211> LENGTH: 168
<212> TYPE: PRT
<213> ORGANISM: Artificial Sequence
<220> FEATURE:
<223> OTHER INFORMATION: Synthetic mouse_p16

<400> SEQUENCE: 5

```
Met Glu Ser Ala Ala Asp Arg Leu Ala Arg Ala Ala Gln Gly Arg
  1               5                  10                  15

Val His Asp Val Arg Ala Leu Leu Glu Ala Gly Val Ser Pro Asn Ala
             20                  25                  30

Pro Asn Ser Phe Gly Arg Thr Pro Ile Gln Val Met Met Met Gly Asn
         35                  40                  45

Val His Val Ala Ala Leu Leu Leu Asn Tyr Gly Ala Asp Ser Asn Cys
     50                  55                  60

Glu Asp Pro Thr Thr Phe Ser Arg Pro Val His Asp Ala Ala Arg Glu
 65                  70                  75                  80

Gly Phe Leu Asp Thr Leu Val Val Leu His Gly Ser Gly Ala Arg Leu
                 85                  90                  95

Asp Val Arg Asp Ala Trp Gly Arg Leu Pro Leu Asp Leu Ala Gln Glu
            100                 105                 110

Arg Gly His Gln Asp Ile Val Arg Tyr Leu Arg Ser Ala Gly Cys Ser
        115                 120                 125

Leu Cys Ser Ala Gly Trp Ser Leu Cys Thr Ala Gly Asn Val Ala Gln
    130                 135                 140

Thr Asp Gly His Ser Phe Ser Ser Thr Pro Arg Ala Leu Glu Leu
145                 150                 155                 160

Arg Gly Gln Ser Gln Glu Gln Ser
                165
```

<210> SEQ ID NO 6
<211> LENGTH: 159
<212> TYPE: PRT
<213> ORGANISM: Artificial Sequence
<220> FEATURE:
<223> OTHER INFORMATION: Synthetic rat_p16

<400> SEQUENCE: 6

```
Met Glu Ser Ser Ala Asp Arg Leu Ala Arg Ala Ala Leu Gly Arg
  1               5                  10                  15

Glu His Glu Val Arg Ala Leu Leu Glu Ala Gly Ala Ser Pro Asn Ala
             20                  25                  30

Pro Asn Thr Phe Gly Arg Thr Pro Ile Gln Val Met Met Met Gly Asn
         35                  40                  45
```

```
Val Lys Val Ala Ala Leu Leu Leu Ser Tyr Gly Ala Asp Ser Asn Cys
 50                  55                  60

Glu Asp Pro Thr Thr Leu Ser Arg Pro Val His Asp Ala Ala Arg Glu
 65                  70                  75                  80

Gly Phe Leu Asp Thr Leu Val Val Leu His Gln Ala Gly Ala Arg Leu
                 85                  90                  95

Asp Val Arg Asp Ala Trp Gly Arg Leu Pro Leu Asp Leu Ala Leu Glu
                100                 105                 110

Arg Gly His His Asp Val Val Arg Tyr Leu Arg Tyr Leu Leu Ser Ser
                115                 120                 125

Ala Gly Asn Val Ser Arg Val Thr Asp Arg His Asn Phe Cys Ser Ser
130                 135                 140

Thr Pro Arg Cys Leu Gly Leu Arg Gly Gln Pro Pro Lys Gln Arg
145                 150                 155

<210> SEQ ID NO 7
<211> LENGTH: 153
<212> TYPE: PRT
<213> ORGANISM: Artificial Sequence
<220> FEATURE:
<223> OTHER INFORMATION: Synthetic anti-EGFR DARPin-01

<400> SEQUENCE: 7

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Asp Asp
                 20                  25                  30

Thr Trp Gly Trp Thr Pro Leu His Leu Ala Ala Tyr Gln Gly His Leu
                 35                  40                  45

Glu Ile Val Glu Val Leu Leu Lys Asn Gly Ala Asp Val Asn Ala Tyr
 50                  55                  60

Asp Tyr Ile Gly Trp Thr Pro Leu His Leu Ala Ala Asp Gly His Leu
 65                  70                  75                  80

Glu Ile Val Glu Val Leu Leu Lys Asn Gly Ala Asp Val Asn Ala Ser
                 85                  90                  95

Asp Tyr Ile Gly Asp Thr Pro Leu His Leu Ala Ala His Asn Gly His
                100                 105                 110

Leu Glu Ile Val Glu Val Leu Leu Lys His Gly Ala Asp Val Asn Ala
                115                 120                 125

Gln Asp Lys Phe Gly Lys Thr Ala Phe Asp Ile Ser Ile Asp Asn Gly
                130                 135                 140

Asn Glu Asp Leu Ala Glu Ile Leu Gln
145                 150

<210> SEQ ID NO 8
<211> LENGTH: 154
<212> TYPE: PRT
<213> ORGANISM: Artificial Sequence
<220> FEATURE:
<223> OTHER INFORMATION: Synthetic Anti-EGFR DARPin-67

<400> SEQUENCE: 8

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Thr Asp
                 20                  25                  30

Asn Asp Gly Asn Thr Pro Leu His Leu Ser Ala Trp Ile Gly His Leu
```

```
                     35                  40                  45
Glu Ile Val Glu Val Leu Leu Lys His Gly Ala Asp Val Asn Ala Asp
         50                  55                  60

Asp Leu Leu Gly Met Thr Pro Leu His Leu Ala Ala Asp Thr Gly His
 65                  70                  75                  80

Leu Glu Ile Val Glu Val Leu Leu Lys Tyr Gly Ala Asp Val Asn Ala
                 85                  90                  95

Arg Asp Thr Arg Gly Lys Thr Pro Leu His Leu Ala Ala Arg Asp Gly
            100                 105                 110

His Leu Glu Ile Val Glu Val Leu Leu Lys His Asp Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 9
<211> LENGTH: 154
<212> TYPE: PRT
<213> ORGANISM: Artificial Sequence
<220> FEATURE:
<223> OTHER INFORMATION: Synthetic Anti-EGFR DARPin-68

<400> SEQUENCE: 9

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Phe Asp
             20                  25                  30

Tyr Trp Gly Met Thr Pro Leu His Leu Ala Ala Asp Asn Gly His Leu
         35                  40                  45

Glu Ile Val Glu Val Leu Leu Lys His Gly Ala Asp Val Asn Ala Ser
     50                  55                  60

Asp Asn Phe Gly Phe Thr Pro Leu His Leu Ala Ala Phe Tyr Gly His
 65                  70                  75                  80

Leu Glu Ile Val Glu Val Leu Leu Lys His Gly Ala Asp Val Asn Ala
                 85                  90                  95

Phe Asp Met Trp Gly Asn Thr Pro Leu His Leu Ala Ala Gln Asn Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 10
<211> LENGTH: 187
<212> TYPE: PRT
<213> ORGANISM: Artificial Sequence
<220> FEATURE:
<223> OTHER INFORMATION: Synthetic Anti-EGFR DARPin-69

<400> SEQUENCE: 10

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Asp Asp
             20                  25                  30
```

```
Asn Ala Gly Arg Thr Pro Leu His Leu Ala Ala Asn Phe Gly His Leu
            35                  40                  45

Glu Ile Val Glu Val Leu Leu Lys Asn Gly Ala Asp Val Asn Ala Lys
 50                  55                  60

Gly His His Cys Asn Thr Pro Leu His Leu Ala Ala Trp Ala Gly His
 65                  70                  75                  80

Leu Glu Ile Val Glu Val Leu Leu Lys Tyr Gly Ala Asp Val Asn Ala
                 85                  90                  95

Asp Asp Asp Glu Gly Tyr Thr Pro Leu His Leu Ala Ala Asp Ile Gly
            100                 105                 110

Asp Leu Glu Ile Val Glu Val Leu Leu Lys Tyr Gly Ala Asp Val Asn
            115                 120                 125

Ala Trp Asp Met Tyr Gly Arg Thr Pro Leu His Leu Ala Ala Ser Ala
130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 11
<211> LENGTH: 16
<212> TYPE: PRT
<213> ORGANISM: Artificial Sequence
<220> FEATURE:
<223> OTHER INFORMATION: Synthetic membrane-translocation sequence (MTS)

<400> SEQUENCE: 11

Ala Ala Val Ala Leu Leu Pro Ala Val Leu Leu Ala Leu Leu Ala Pro
 1               5                  10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic MTS fragment

<400> SEQUENCE: 12

Ala Ala Val Ala Leu Leu Pro
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic MTS fragment

<400> SEQUENCE: 13

Ala Val Leu Leu Ala Leu Leu Ala Pro
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic tMTS

<400> SEQUENCE: 14
```

```
Ala Val Leu Leu Ala Leu Leu Ala Ala
  1               5

<210> SEQ ID NO 15
<211> LENGTH: 16
<212> TYPE: PRT
<213> ORGANISM: Artificial Sequence
<220> FEATURE:
<223> OTHER INFORMATION: Synthetic MTS variant

<400> SEQUENCE: 15

Ala Ala Val Ala Leu Leu Pro Ala Val Leu Leu Ala Leu Leu Ala Ala
  1               5                  10                  15

<210> SEQ ID NO 16
<211> LENGTH: 5
<212> TYPE: PRT
<213> ORGANISM: Artificial Sequence
<220> FEATURE:
<223> OTHER INFORMATION: Synthetic Unit of basic amino acid

<400> SEQUENCE: 16

Lys Lys Lys Arg Lys
  1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Unit of basic amino acid

<400> SEQUENCE: 17

Lys Lys Lys Arg
  1

<210> SEQ ID NO 18
<211> LENGTH: 4
<212> TYPE: PRT
<213> ORGANISM: Artificial Sequence
<220> FEATURE:
<223> OTHER INFORMATION: Synthetic Unit of basic amino acid

<400> SEQUENCE: 18

Arg Lys Arg Lys
  1

<210> SEQ ID NO 19
<211> LENGTH: 6
<212> TYPE: PRT
<213> ORGANISM: Artificial Sequence
<220> FEATURE:
<223> OTHER INFORMATION: Synthetic Unit of basic amino acid

<400> SEQUENCE: 19

Arg Lys Arg Lys Arg Lys
  1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Unit of basic amino acid

<400> SEQUENCE: 20

Lys Lys Lys Lys Lys
```

```
<210> SEQ ID NO 21
<211> LENGTH: 6
<212> TYPE: PRT
<213> ORGANISM: Artificial Sequence
<220> FEATURE:
<223> OTHER INFORMATION: Synthetic Unit of basic amino acid

<400> SEQUENCE: 21

Lys Lys Lys Lys Lys Arg
 1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Unit of basic amino acid

<400> SEQUENCE: 22

Lys Lys Lys Arg Lys Arg
 1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Unit of basic amino acid

<400> SEQUENCE: 23

Arg Arg Arg Arg Arg
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Unit of basic amino acid

<400> SEQUENCE: 24

Arg Arg Arg Arg Arg Arg
 1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic MTD103

<400> SEQUENCE: 25

Leu Ala Leu Pro Val Leu Leu Leu Ala
 1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic MMP9 cleavage region

<400> SEQUENCE: 26

Ser Gly Lys Ile Pro Arg Thr Leu Thr Ala
 1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Synthetic MMP9 cleavage region

<400> SEQUENCE: 27

Ser Gly Lys Gly Pro Arg Gln Ile Thr Ala
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Synthetic MMP9 cleavage region

<400> SEQUENCE: 28

Ser Gly Pro Arg Ala Val Ser Thr Thr Ala
 1               5                  10

<210> SEQ ID NO 29
<211> LENGTH: 21
<212> TYPE: PRT
<213> ORGANISM: Artificial Sequence
<220> FEATURE:
<223> OTHER INFORMATION: Synthetic Fusion peptide (MST-NLS)

<400> SEQUENCE: 29

Ala Ala Val Ala Leu Leu Pro Ala Val Leu Leu Ala Leu Leu Ala Pro
 1               5                  10                  15

Lys Lys Lys Arg Lys
            20

<210> SEQ ID NO 30
<211> LENGTH: 184
<212> TYPE: PRT
<213> ORGANISM: Artificial Sequence
<220> FEATURE:
<223> OTHER INFORMATION: Synthetic Fusion protein (anti-EGFR
      DARPin-M9R-MTS-NLS)

<400> SEQUENCE: 30

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
                20                  25                  30

Thr Trp Gly Trp Thr Pro Leu His Leu Ala Ala Tyr Gln Gly His Leu
            35                  40                  45

Glu Ile Val Glu Val Leu Leu Lys Asn Gly Ala Asp Val Asn Ala Tyr
        50                  55                  60

Asp Tyr Ile Gly Trp Thr Pro Leu His Leu Ala Ala Asp Gly His Leu
65                  70                  75                  80

Glu Ile Val Glu Val Leu Leu Lys Asn Gly Ala Asp Val Asn Ala Ser
                85                  90                  95

Asp Tyr Ile Gly Asp Thr Pro Leu His Leu Ala Ala His Asn Gly His
            100                 105                 110

Leu Glu Ile Val Glu Val Leu Leu Lys His Gly Ala Asp Val Asn Ala
        115                 120                 125

Gln Asp Lys Phe Gly Lys Thr Ala Phe Asp Ile Ser Ile Asp Asn Gly

```
                    130                 135                 140
Asn Glu Asp Leu Ala Glu Ile Leu Gln Ser Gly Lys Ile Pro Arg Thr
145                 150                 155                 160

Leu Thr Ala Ala Ala Val Ala Leu Leu Pro Ala Val Leu Leu Ala Leu
                165                 170                 175

Leu Ala Pro Lys Lys Lys Arg Lys
            180
```

<210> SEQ ID NO 31
<211> LENGTH: 552
<212> TYPE: DNA
<213> ORGANISM: Artificial Sequence
<220> FEATURE:
<223> OTHER INFORMATION: Synthetic anti-EGFR DARPin-M9R-MTS-NLS coding DNA

<400> SEQUENCE: 31

```
gatctgggca aaaaactgct ggaagcggcg cgcgcgggcc aggatgatga agtgcgcatt    60
ctgatggcga atggtgcgga tgttaacgcg acgataccta ggggctggac cccactgcat   120
ctggccgcgt atcagggtca cctggaaatc gtggaggtgc tgctgaaaaa cggcgcggat   180
gtgaacgcgt atgattatat tggctggacc ccgctgcatc tggcggcgga tggccatctg   240
gaaattgtgg aagtgctgct gaaaaacggc gctgatgtta atgctagcga ttatattggc   300
gatacgccgc tgcacctggc agcgcataac ggccatctgg agattgttga agttctgctg   360
aagcatggcg ccgatgtgaa tgcgcaggat aaatttggca aaccgcgtt tgatattagc    420
attgataacg gcaacgaaga tctggcggaa attctgcaga gcggcaaaat tccgcgtacc   480
ctgaccgcgg ccgcggtagc gctgctcccg gcggtcctgc tggccttgct ggcgcccaaa   540
aagaagagaa ag                                                      552
```

<210> SEQ ID NO 32
<211> LENGTH: 12
<212> TYPE: PRT
<213> ORGANISM: Artificial Sequence
<220> FEATURE:
<223> OTHER INFORMATION: Synthetic pMI-alpha

<400> SEQUENCE: 32

```
Thr Asn Trp Tyr Ala Asn Leu Glu Lys Leu Leu Arg
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: Synthetic pMI-beta

<400> SEQUENCE: 33

```
Thr Ala Trp Tyr Ala Asn Phe Glu Lys Leu Leu Arg
1               5                   10
```

<210> SEQ ID NO 34
<211> LENGTH: 15
<212> TYPE: PRT
<213> ORGANISM: Artificial Sequence
<220> FEATURE:
<223> OTHER INFORMATION: Synthetic p53 fragment

<400> SEQUENCE: 34

```
Ser Gln Glu Thr Phe Ser Asp Leu Trp Lys Leu Leu Pro Glu Asn
```

<210> SEQ ID NO 35
<211> LENGTH: 340
<212> TYPE: PRT
<213> ORGANISM: Artificial Sequence
<220> FEATURE:
<223> OTHER INFORMATION: Synthetic Conjugate (anti-EGFR DARPin-M9R-MTS-NLS-p16M7)

<400> SEQUENCE: 35

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr
    50                  55                  60

Asp Tyr Ile Gly Trp Thr Pro Leu His Leu Ala Ala Asp Gly His Leu
65                  70                  75                  80

Glu Ile Val Glu Val Leu Leu Lys Asn Gly Ala Asp Val Asn Ala Ser
                85                  90                  95

Asp Tyr Ile Gly Asp Thr Pro Leu His Leu Ala Ala His Asn Gly His
            100                 105                 110

Leu Glu Ile Val Glu Val Leu Leu Lys His Gly Ala Asp Val Asn Ala
        115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln Ser Gly Lys Ile Pro Arg Thr
145                 150                 155                 160

Leu Thr Ala Ala Ala Val Ala Leu Leu Pro Ala Val Leu Leu Ala Leu
                165                 170                 175

Leu Ala Pro Lys Lys Lys Arg Lys Met Glu Pro Ala Ala Gly Ser Ser
            180                 185                 190

Met Glu Pro Ser Ala Asp Lys Leu Ala Thr Ala Ala Arg Gly Arg
        195                 200                 205

Val Glu Glu Val Arg Ala Leu Leu Glu Ala Gly Ala Asp Pro Asn Ala
    210                 215                 220

Pro Asn Ser Tyr Gly Arg Arg Pro Ile Gln Val Met Met Met Gly Ser
225                 230                 235                 240

Ala Arg Val Ala Glu Leu Leu Leu Lys His Gly Ala Glu Pro Asn Ser
                245                 250                 255

Ala Asp Pro Ala Thr Ser Thr Arg Pro Val His Asp Ala Ala Arg Glu
            260                 265                 270

Gly Phe Leu Asp Thr Leu Val Val Leu His Arg Ala Gly Ala Arg Leu
        275                 280                 285

Asp Ala Arg Asp Ala Trp Gly Arg Thr Pro Val Asp Leu Ala Glu Glu
    290                 295                 300

Leu Gly His Arg Asp Val Ala Arg Tyr Leu Arg Ala Ala Ala Gly Gly
305                 310                 315                 320

Thr Arg Gly Ser Asn His Ala Arg Ile Asp Ala Ala Glu Gly Pro Ser
                325                 330                 335

Asp Ile Pro Asp
            340
```

```
<210> SEQ ID NO 36
<211> LENGTH: 377
<212> TYPE: PRT
<213> ORGANISM: Artificial Sequence
<220> FEATURE:
<223> OTHER INFORMATION: Synthetic Conjugate precursor

<400> SEQUENCE: 36
```

Met Arg Gly Ser His His His His His His Asp Tyr Asp Ile Pro Thr
1               5                   10                  15

Thr Glu Asn Leu Tyr Phe Gln Gly Ser Gly Ser Gly Ser Asp Leu Gly
            20                  25                  30

Lys Lys Leu Leu Glu Ala Ala Arg Ala Gly Gln Asp Asp Glu Val Arg
        35                  40                  45

Ile Leu Met Ala Asn Gly Ala Asp Val Asn Ala Asp Asp Thr Trp Gly
    50                  55                  60

Trp Thr Pro Leu His Leu Ala Ala Tyr Gln Gly His Leu Glu Ile Val
65                  70                  75                  80

Glu Val Leu Leu Lys Asn Gly Ala Asp Val Asn Ala Tyr Asp Tyr Ile
                85                  90                  95

Gly Trp Thr Pro Leu His Leu Ala Ala Asp Gly His Leu Glu Ile Val
            100                 105                 110

Glu Val Leu Leu Lys Asn Gly Ala Asp Val Asn Ala Ser Asp Tyr Ile
        115                 120                 125

Gly Asp Thr Pro Leu His Leu Ala Ala His Asn Gly His Leu Glu Ile
    130                 135                 140

Val Glu Val Leu Leu Lys His Gly Ala Asp Val Asn Ala Gln Asp Lys
145                 150                 155                 160

Phe Gly Lys Thr Ala Phe Asp Ile Ser Ile Asp Asn Gly Asn Glu Asp
                165                 170                 175

Leu Ala Glu Ile Leu Gln Glu Phe Ser Gly Lys Ile Pro Arg Thr Leu
            180                 185                 190

Thr Ala Gly Ser Ala Ala Val Ala Leu Leu Pro Ala Val Leu Leu Ala
        195                 200                 205

Leu Leu Ala Pro Gly Ser Lys Lys Arg Lys Gly Ser Met Glu Pro
    210                 215                 220

Ala Ala Gly Ser Ser Met Glu Pro Ser Ala Asp Lys Leu Ala Thr Ala
225                 230                 235                 240

Ala Ala Arg Gly Arg Val Glu Val Arg Ala Leu Leu Glu Ala Gly
                245                 250                 255

Ala Asp Pro Asn Ala Pro Asn Ser Tyr Gly Arg Arg Pro Ile Gln Val
            260                 265                 270

Met Met Met Gly Ser Ala Arg Val Ala Glu Leu Leu Leu Lys His Gly
        275                 280                 285

Ala Glu Pro Asn Ser Ala Asp Pro Ala Thr Ser Thr Arg Pro Val His
    290                 295                 300

Asp Ala Ala Arg Glu Gly Phe Leu Asp Thr Leu Val Val Leu His Arg
305                 310                 315                 320

Ala Gly Ala Arg Leu Asp Ala Arg Asp Ala Trp Gly Arg Thr Pro Val
                325                 330                 335

Asp Leu Ala Glu Glu Leu Gly His Arg Asp Val Ala Arg Tyr Leu Arg
            340                 345                 350

Ala Ala Ala Gly Gly Thr Arg Gly Ser Asn His Ala Arg Ile Asp Ala
        355                 360                 365

Ala Glu Gly Pro Ser Asp Ile Pro Asp
        370                 375

<210> SEQ ID NO 37
<211> LENGTH: 1166
<212> TYPE: DNA
<213> ORGANISM: Artificial Sequence
<220> FEATURE:
<223> OTHER INFORMATION: Synthetic Conjugate precursor coding DNA

<400> SEQUENCE: 37

```
catatgagag gatcgcatca ccatcaccat cacgattacg atatcccaac gaccgaaaac      60
ctgtattttc agggatccgg cagcggcagc gatctgggca aaaaactgct ggaagcggcg     120
cgcgcgggcc aggatgatga agtgcgcatt ctgatggcga atggtgcgga tgttaacgcg     180
gacgatacct ggggctggac cccactgcat ctggccgcgt atcagggtca cctgaaaatc     240
gtggaggtgc tgctgaaaaa cggcgcggat gtgaacgcgt atgattatat ggctggacc     300
ccgctgcatc tggcggcgga tggccatctg gaaattgtgg aagtgctgct gaaaaacggc     360
gctgatgtta atgctagcga ttatattggc gatacgccgc tgcacctggc agcgcataac     420
ggccatctgg agattgttga agttctgctg aagcatggcg ccgatgtgaa tgcgcaggat     480
aaatttggca aaccgcgtt tgatattagc attgataacg caacgaaga tctggcggaa      540
attctgcagg aatttagcgg caaaattccg cgtaccctga ccgcgggcag cgccgcggta     600
gcgctgctcc cggcggtcct gctggccttg ctggcgcccg cagcaaaaa gaagagaaag     660
ggcagcatgg aaccggctgc tggcagctct atggaaccgt ctgctgacaa actggctacc     720
gctgctgctc gtggtcgtgt tgaagaagtt cgtgctctgc tggaagctgg tgctgatccg     780
aacgctccga actcttacgg tcgtcgtccg atccaggtta tgatgatggg cagcgctcgt     840
gttgctgaac tgctgctgaa acacggtgct gaaccgaaca gcgctgaccc ggctaccagc     900
acccgtccgg ttcacgacgc tgctcgtgaa ggtttcctgg acaccctggt tgttctgcac     960
cgtgctggtg ctcgtctgga cgcgcgtgac gcttggggtc gtaccccggt tgacctggct    1020
gaagaactgg gtcaccgtga cgttgctcgt tacctgcgtg ctgctgctgg tggtaccgt    1080
ggcagcaacc acgtcgtat cgacgctgct gaaggtccgt ctgacatccc ggactaataa    1140
ctcgagcacc accaccacca ccactg                                        1166
```

<210> SEQ ID NO 38
<211> LENGTH: 9
<212> TYPE: PRT
<213> ORGANISM: Artificial Sequence
<220> FEATURE:
<223> OTHER INFORMATION: Synthetic TAT

<400> SEQUENCE: 38

Arg Lys Lys Arg Arg Gln Arg Arg Arg
  1               5

<210> SEQ ID NO 39
<211> LENGTH: 21
<212> TYPE: PRT
<213> ORGANISM: Artificial Sequence
<220> FEATURE:
<223> OTHER INFORMATION: Synthetic TP10

<400> SEQUENCE: 39

Ala Gly Tyr Leu Leu Gly Lys Ile Asn Leu Lys Ala Leu Ala Ala Leu
  1               5                  10                  15

```
Ala Lys Lys Ile Leu
            20
```

<210> SEQ ID NO 40
<211> LENGTH: 16
<212> TYPE: PRT
<213> ORGANISM: Artificial Sequence
<220> FEATURE:
<223> OTHER INFORMATION: Synthetic Penetratin

<400> SEQUENCE: 40

```
Arg Gln Ile Lys Ile Trp Phe Gln Asn Arg Arg Met Lys Trp Lys Lys
  1               5                  10                  15
```

<210> SEQ ID NO 41
<211> LENGTH: 9
<212> TYPE: PRT
<213> ORGANISM: Artificial Sequence
<220> FEATURE:
<223> OTHER INFORMATION: Synthetic R9

<400> SEQUENCE: 41

```
Arg Arg Arg Arg Arg Arg Arg Arg Arg
  1               5
```

<210> SEQ ID NO 42
<211> LENGTH: 18
<212> TYPE: PRT
<213> ORGANISM: Artificial Sequence
<220> FEATURE:
<223> OTHER INFORMATION: Synthetic MAP

<400> SEQUENCE: 42

```
Lys Leu Ala Leu Lys Leu Ala Leu Lys Ala Leu Lys Ala Ala Leu Lys
  1               5                  10                  15

Leu Ala
```

<210> SEQ ID NO 43
<211> LENGTH: 126
<212> TYPE: PRT
<213> ORGANISM: Artificial Sequence
<220> FEATURE:
<223> OTHER INFORMATION: Synthetic Non-EGFR targeting DARPin

<400> SEQUENCE: 43

```
Gly Ser Asp Leu Gly Lys Lys Leu Leu Glu Ala Ala Arg Ala Gly Gln
  1               5                  10                  15

Asp Asp Glu Val Arg Ile Leu Met Ala Asn Gly Ala Asp Val Asn Ala
             20                  25                  30

Glu Asp Lys Val Gly Leu Thr Pro Leu His Leu Ala Ala Met Asn Asp
         35                  40                  45

His Leu Glu Ile Val Glu Val Leu Leu Lys Asn Gly Ala Asp Val Asn
     50                  55                  60

Ala Ile Asp Ala Ile Gly Glu Thr Pro Leu His Leu Val Ala Met Tyr
 65                  70                  75                  80

Gly His Leu Glu Ile Val Glu Val Leu Leu Lys His Gly Ala Asp Val
                 85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125
```

<210> SEQ ID NO 44
<211> LENGTH: 153
<212> TYPE: PRT
<213> ORGANISM: Artificial Sequence
<220> FEATURE:
<223> OTHER INFORMATION: Synthetic DARPin E_01

<400> SEQUENCE: 44

```
Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr
    50                  55                  60

Asp Tyr Ile Gly Trp Thr Pro Leu His Leu Ala Ala Asp Gly His Leu
65                  70                  75                  80

Glu Ile Val Glu Val Leu Leu Lys Asn Gly Ala Asp Val Asn Ala Ser
                85                  90                  95

Asp Tyr Ile Gly Asp Thr Pro Leu His Leu Ala Ala His Asn Gly His
            100                 105                 110

Leu Glu Ile Val Glu Val Leu Leu Lys His Gly Ala Asp Val Asn Ala
        115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln
145                 150
```

<210> SEQ ID NO 45
<211> LENGTH: 154
<212> TYPE: PRT
<213> ORGANISM: Artificial Sequence
<220> FEATURE:
<223> OTHER INFORMATION: Synthetic DARPin E_67

<400> SEQUENCE: 45

```
Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Thr Asp
            20                  25                  30

Asn Asp Gly Asn Thr Pro Leu His Leu Ser Ala Trp Ile Gly His Leu
        35                  40                  45

Glu Ile Val Glu Val Leu Leu Lys His Gly Ala Asp Val Asn Ala Asp
    50                  55                  60

Asp Leu Leu Gly Met Thr Pro Leu His Leu Ala Ala Asp Thr Gly His
65                  70                  75                  80

Leu Glu Ile Val Glu Val Leu Leu Lys Tyr Gly Ala Asp Val Asn Ala
                85                  90                  95

Arg Asp Thr Arg Gly Lys Thr Pro Leu His Leu Ala Ala Arg Asp Gly
            100                 105                 110

His Leu Glu Ile Val Glu Val Leu Leu Lys His Asp Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

```
<210> SEQ ID NO 46
<211> LENGTH: 154
<212> TYPE: PRT
<213> ORGANISM: Artificial Sequence
<220> FEATURE:
<223> OTHER INFORMATION: Synthetic DARPin E_68

<400> SEQUENCE: 46

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Phe Asp
             20                  25                  30

Tyr Trp Gly Met Thr Pro Leu His Leu Ala Ala Asp Asn Gly His Leu
         35                  40                  45

Glu Ile Val Glu Val Leu Leu Lys His Gly Ala Asp Val Asn Ala Ser
     50                  55                  60

Asp Asn Phe Gly Phe Thr Pro Leu His Leu Ala Ala Phe Tyr Gly His
 65                  70                  75                  80

Leu Glu Ile Val Glu Val Leu Leu Lys His Gly Ala Asp Val Asn Ala
                 85                  90                  95

Phe Asp Met Trp Gly Asn Thr Pro Leu His Leu Ala Ala Gln Asn Gly
             100                 105                 110

His Leu Glu Ile Val Glu Val Leu Leu Lys Asn Gly Ala Asp Val Asn
         115                 120                 125

Ala Gln Asp Lys Phe Gly Lys Thr Ala Phe Asp Ile Ser Ile Asp Asn
     130                 135                 140

Gly Asn Glu Asp Leu Ala Glu Ile Leu Gln
145                 150

<210> SEQ ID NO 47
<211> LENGTH: 187
<212> TYPE: PRT
<213> ORGANISM: Artificial Sequence
<220> FEATURE:
<223> OTHER INFORMATION: Synthetic DARPin E_69

<400> SEQUENCE: 47

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Asp Asp
             20                  25                  30

Asn Ala Gly Arg Thr Pro Leu His Leu Ala Ala Asn Phe Gly His Leu
         35                  40                  45

Glu Ile Val Glu Val Leu Leu Lys Asn Gly Ala Asp Val Asn Ala Lys
     50                  55                  60

Gly His His Cys Asn Thr Pro Leu His Leu Ala Ala Trp Ala Gly His
 65                  70                  75                  80

Leu Glu Ile Val Glu Val Leu Leu Lys Tyr Gly Ala Asp Val Asn Ala
                 85                  90                  95

Asp Asp Asp Glu Gly Tyr Thr Pro Leu His Leu Ala Ala Asp Ile Gly
             100                 105                 110

Asp Leu Glu Ile Val Glu Val Leu Leu Lys Tyr Gly Ala Asp Val Asn
         115                 120                 125

Ala Trp Asp Met Tyr Gly Arg Thr Pro Leu His Leu Ala Ala Ser Ala
     130                 135                 140

Gly His Leu Glu Ile Val Glu Val Leu Leu Lys Tyr Gly Ala Asp Val
145                 150                 155                 160
```

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 48
<211> LENGTH: 154
<212> TYPE: PRT
<213> ORGANISM: Artificial Sequence
<220> FEATURE:
<223> OTHER INFORMATION: Synthetic DARPin 9_16

<400> SEQUENCE: 48

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala His Asp
                20                  25                  30

Phe His Gly Leu Thr Pro Leu His Leu Ala Ala Gly Met Gly His Leu
            35                  40                  45

Glu Ile Val Glu Val Leu Leu Lys Asn Gly Ala Asp Val Asn Ala Val
        50                  55                  60

Asp Thr Asp Gly Ile Thr Leu Leu His Leu Ala Ala Tyr Tyr Gly His
 65                  70                  75                  80

Leu Glu Ile Val Glu Val Leu Leu Lys His Gly Ala Asp Val Asn Ala
                85                  90                  95

His Asp Tyr Ala Gly Ser Thr Pro Leu His Leu Ala Ala Asn Thr Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150

<210> SEQ ID NO 49
<211> LENGTH: 154
<212> TYPE: PRT
<213> ORGANISM: Artificial Sequence
<220> FEATURE:
<223> OTHER INFORMATION: Synthetic DARPin 9_26

<400> SEQUENCE: 49

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Lys Asp
                20                  25                  30

Phe Tyr Gly Ile Thr Pro Leu His Leu Ala Ala Ala Tyr Gly His Leu
            35                  40                  45

Glu Ile Val Glu Val Leu Leu Lys His Gly Ala Asp Val Asn Ala His
        50                  55                  60

Asp Trp Asn Gly Trp Thr Pro Leu His Leu Ala Ala Lys Tyr Gly His
 65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn

```
                    115                 120                 125
Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 50
<211> LENGTH: 154
<212> TYPE: PRT
<213> ORGANISM: Artificial Sequence
<220> FEATURE:
<223> OTHER INFORMATION: Synthetic DARPin 9_29
<220> FEATURE:
<221> NAME/KEY: MOD_RES
<222> LOCATION: (67)
<223> OTHER INFORMATION: Xaa is Ala, Ile, Leu, Met, Phe, Pro, Trp,
      Val, Asn, Cys, Gln, Gly, Ser, Thr, Tyr, Asp, Glu, Arg, His or Lys

<400> SEQUENCE: 50

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
            20                  25                  30

Phe Tyr Gly Ile Thr Pro Leu His Leu Ala Ala Asn Phe Gly His Leu
        35                  40                  45

Glu Ile Val Glu Val Leu Leu Lys His Gly Ala Asp Val Asn Ala Phe
    50                  55                  60

Asp Tyr Xaa Asp Asn Thr Pro Leu His Leu Ala Asp Ala Gly His
65                  70                  75                  80

Leu Glu Ile Val Glu Val Leu Lys Tyr Gly Ala Asp Val Asn Ala
                85                  90                  95

Ser Asp Arg Asp Gly His Thr Pro Leu His Leu Ala Ala Arg Glu Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 51
<211> LENGTH: 154
<212> TYPE: PRT
<213> ORGANISM: Artificial Sequence
<220> FEATURE:
<223> OTHER INFORMATION: Synthetic DARPin H_14

<400> SEQUENCE: 51

Asp Leu Gly Lys Lys Leu Leu Glu Ala Ala Arg Ala Gly Gln Asp Asp
1               5                   10                  15

Glu Val Cys Ile Leu Met Ala Asn Gly Ala Asp Val Asn Ala Thr Asp
            20                  25                  30

Ile His Gly His Thr Pro Leu His Leu Ala Ala Ala Met Gly His Leu
        35                  40                  45

Glu Ile Val Glu Val Leu Leu Lys Asn Gly Ala Asp Val Asn Ala Asn
    50                  55                  60

Asp Trp Arg Gly Phe Thr Pro Leu His Leu Ala Ala Leu Asn Gly His
65                  70                  75                  80

Leu Glu Ile Val Glu Val Leu Leu Lys Asn Gly Ala Asp Val Asn Ala
```

```
                85                  90                  95
Thr Asp Thr Ala Gly Asn Thr Pro Leu His Leu Ala Ala Trp Phe Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 52
<211> LENGTH: 187
<212> TYPE: PRT
<213> ORGANISM: Artificial Sequence
<220> FEATURE:
<223> OTHER INFORMATION: Synthetic DARPin B4_01

<400> SEQUENCE: 52

Asp Leu Gly Lys Lys Leu Leu Glu Ala Ala Arg Ala Gly Gln Asp Asp
 1               5                  10                  15

Glu Val His Ile Leu Met Ala Asn Gly Ala Asp Val Asn Ala Val Asp
            20                  25                  30

Trp Met Gly Asp Thr Pro Leu His Leu Ala Ala Phe Tyr Gly His Leu
        35                  40                  45

Glu Ile Val Glu Val Leu Leu Lys Asn Gly Ala Asp Val Asn Ala Lys
    50                  55                  60

Asp Thr Trp Gly Asp Thr Pro Leu His Leu Ala Ala Leu Leu Gly Arg
65                  70                  75                  80

Leu Glu Ile Val Glu Val Leu Leu Lys His Gly Ala Asp Val Asn Ala
                85                  90                  95

Ile Asp Met Arg Gly Thr Thr Pro Leu His Leu Ala Ala Pro Ala Gly
            100                 105                 110

His Leu Glu Ile Val Glu Val Leu Leu Lys Tyr Gly Ala Asp Val Asn
        115                 120                 125

Ala Asp Asp Val His Gly Asn Thr Pro Leu His Leu Ala Ala Met Ser
    130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 53
<211> LENGTH: 154
<212> TYPE: PRT
<213> ORGANISM: Artificial Sequence
<220> FEATURE:
<223> OTHER INFORMATION: Synthetic DARPin B4_02

<400> SEQUENCE: 53

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Lys Asp
            20                  25                  30

Asn Ala Gly Lys Thr Ala Leu His Leu Ala Ala Val Trp Gly His Leu
        35                  40                  45
```

```
Glu Ile Val Glu Val Leu Leu Lys Asn Gly Ala Asp Val Asn Ala Tyr
 50                  55                  60

Asp Ala Ser Gly Tyr Thr Leu Leu His Leu Ala Ala Arg Met Gly His
 65                  70                  75                  80

Leu Glu Ile Val Glu Val Leu Leu Lys Tyr Gly Ala Asp Val Asn Ala
                 85                  90                  95

Arg Asp Arg Phe Gly Ser Thr Pro Leu His Leu Ala Ala Trp His Gly
            100                 105                 110

His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150
```

<210> SEQ ID NO 54
<211> LENGTH: 154
<212> TYPE: PRT
<213> ORGANISM: Artificial Sequence
<220> FEATURE:
<223> OTHER INFORMATION: Synthetic DARPin B4_07

<400> SEQUENCE: 54

```
Asp Leu Gly Lys Lys Leu Leu Glu Ala Ala Arg Ala Gly Gln Asp Asp
 1               5                   10                  15

Glu Val Arg Ile Leu Met Ala Asn Gly Ala Asp Val Asn Ala Arg Asp
                 20                  25                  30

Val Phe Gly Trp Thr Pro Leu His Leu Ala Ala Val Asp Gly His Leu
             35                  40                  45

Glu Ile Val Glu Val Leu Leu Lys Tyr Gly Ala Asp Val Asn Ala Arg
 50                  55                  60

Asp Val Ala Gly Arg Thr Pro Leu His Leu Ala Ala Ser Phe Gly His
 65                  70                  75                  80

Leu Glu Ile Val Glu Val Leu Leu Lys Tyr Gly Ala Asp Val Asn Ala
                 85                  90                  95

Val Asp Tyr Thr Gly Thr Thr Pro Leu His Leu Ala Ala Trp His Gly
            100                 105                 110

His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150
```

<210> SEQ ID NO 55
<211> LENGTH: 154
<212> TYPE: PRT
<213> ORGANISM: Artificial Sequence
<220> FEATURE:
<223> OTHER INFORMATION: Synthetic DARPin B4_33

<400> SEQUENCE: 55

```
Asp Leu Gly Lys Lys Leu Leu Glu Ala Ala Arg Ala Gly Gln Asp Asp
 1               5                   10                  15

Glu Val Arg Ile Leu Met Ala Asn Gly Ala Asp Val Asn Ala Glu Asp
                 20                  25                  30

Ala Thr Gly Phe Thr Pro Leu His Leu Ala Ala Val Trp Gly His Leu
             35                  40                  45
```

-continued

```
Glu Ile Val Glu Val Leu Leu Lys Asn Gly Ala Asp Val Asn Ala Asn
 50                  55                  60

Asp Gln Tyr Gly Tyr Thr Pro Leu His Leu Ala Ala Arg Met Gly His
 65                  70                  75                  80

Leu Glu Ile Val Glu Val Leu Lys His Gly Ala Asp Val Asn Ala
                 85                  90                  95

Ile Asp Val Leu Gly Thr Thr Pro Leu His Leu Ala Ala Trp His Gly
                100                 105                 110

His Leu Glu Ile Val Glu Val Leu Leu Lys Asn Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150
```

<210> SEQ ID NO 56
<211> LENGTH: 154
<212> TYPE: PRT
<213> ORGANISM: Artificial Sequence
<220> FEATURE:
<223> OTHER INFORMATION: Synthetic DARPin B4_45

<400> SEQUENCE: 56

```
Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Arg Asp
                 20                  25                  30

Asp Gly Gly Thr Thr Pro Leu His Leu Ala Ala Asn His Gly His Leu
             35                  40                  45

Glu Ile Val Glu Val Leu Leu Lys Tyr Gly Ala Asp Val Asn Ala Asn
 50                  55                  60

Asp Arg Tyr Gly Tyr Thr Thr Leu His Leu Ala Ala Arg His Gly His
 65                  70                  75                  80

Leu Glu Ile Val Glu Val Leu Leu Lys His Gly Ala Asp Val Asn Ala
                 85                  90                  95

Phe Asp Asn Thr Gly Gln Thr Pro Leu His Leu Ala Ala Trp His Gly
                100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150
```

<210> SEQ ID NO 57
<211> LENGTH: 187
<212> TYPE: PRT
<213> ORGANISM: Artificial Sequence
<220> FEATURE:
<223> OTHER INFORMATION: Synthetic DARPin B4_50

<400> SEQUENCE: 57

```
Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala His Asp
                 20                  25                  30

Arg Tyr Gly Val Thr Pro Leu His Leu Ala Ala Tyr Phe Gly His Leu
```

```
            35                  40                  45

Glu Ile Val Glu Val Leu Leu Lys Asn Gly Ala Asp Val Asn Ala Asp
         50                  55                  60

Asp His Asp Gly Tyr Thr Pro Leu His Leu Ala Ala Asp Lys Gly His
 65                  70                  75                  80

Leu Glu Ile Val Glu Val Leu Leu Lys His Gly Ala Asp Val Asn Ala
                 85                  90                  95

Asp Asp Ser Met Gly Asn Thr Pro Leu His Leu Ala Ala Arg His Gly
                100                 105                 110

His Leu Glu Ile Val Glu Val Leu Leu Lys His Gly Ala Asp Val Asn
            115                 120                 125

Ala Asn Asp Phe Met Gly Ser Thr Pro Leu His Leu Ala Ala Trp Ser
        130                 135                 140

Gly His Leu Glu Ile Val Glu Val Leu Leu Lys His Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 58
<211> LENGTH: 220
<212> TYPE: PRT
<213> ORGANISM: Artificial Sequence
<220> FEATURE:
<223> OTHER INFORMATION: Synthetic DARPin B4_58

<400> SEQUENCE: 58

Asp Leu Gly Lys Lys Leu Leu Glu Ala Thr Arg Ala Gly Gln Asp Asp
  1               5                  10                  15

Glu Val Arg Ile Leu Met Ala Asn Gly Ala Asp Val Asn Ala Phe Asp
             20                  25                  30

Ser Asn Gly Ile Thr Pro Leu His Leu Ala Ala Phe Gly His Leu
         35                  40                  45

Glu Ile Val Glu Val Leu Leu Lys Asn Gly Ala Asp Val Asn Ala His
         50                  55                  60

Asp Ser Tyr Gly Ser Thr Pro Leu His Leu Ala Ala Asn Arg Gly His
 65                  70                  75                  80

Leu Glu Ile Val Glu Val Leu Leu Lys Tyr Gly Ala Asp Val Asn Ala
                 85                  90                  95

Phe Asp Ser Thr Gly Gln Thr Pro Leu His Leu Ala Ala Ser Gln Gly
                100                 105                 110

His Leu Glu Ile Val Glu Val Leu Leu Lys Tyr Gly Ala Asp Val Asn
            115                 120                 125

Ala Ser Asp Arg Met Gly Phe Thr Pro Leu His Leu Ala Ala Tyr Thr
        130                 135                 140

Gly His Leu Glu Ile Val Glu Val Leu Leu Lys Asn Gly Ala Asp Val
145                 150                 155                 160

Asn Ala Lys Asp Phe Val Gly Trp Thr Pro Leu His Leu Ala Ala Tyr
                165                 170                 175

Arg Gly His Leu Glu Ile Val Glu Val Leu Leu Lys His Gly Ala Asp
            180                 185                 190

Val Asn Ala Gln Asp Lys Phe Gly Lys Thr Ala Phe Asp Ile Ser Ile
        195                 200                 205

Asp Asn Gly Asn Glu Asp Leu Ala Glu Ile Leu Gln
```

-continued

```
              210                 215                 220
```

<210> SEQ ID NO 59
<211> LENGTH: 154
<212> TYPE: PRT
<213> ORGANISM: Artificial Sequence
<220> FEATURE:
<223> OTHER INFORMATION: Synthetic DARPin I_01

<400> SEQUENCE: 59

```
Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asn Asp
                20                  25                  30

Ile Ser Gly Tyr Thr Pro Leu His Leu Ala Ala Tyr Val Gly His Gln
            35                  40                  45

Glu Ile Val Glu Val Leu Leu Lys Asn Gly Ala Asp Val Asn Ala Asp
     50                  55                  60

Asp Thr Trp Gly Asp Thr Pro Leu His Leu Ala Ala Leu Phe Gly His
 65                  70                  75                  80

Leu Glu Ile Val Glu Val Leu Leu Lys Tyr Gly Ala Asp Val Asn Ala
                85                  90                  95

His Asp Arg Phe Gly Phe Thr Pro Leu His Leu Ala Ala Ser Ser Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

<210> SEQ ID NO 60
<211> LENGTH: 121
<212> TYPE: PRT
<213> ORGANISM: Artificial Sequence
<220> FEATURE:
<223> OTHER INFORMATION: Synthetic DARPin I_02

<400> SEQUENCE: 60

```
Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Arg Asp
                20                  25                  30

Met Ser Gly Tyr Thr Pro Leu His Leu Ala Ala His Met Gly His Leu
            35                  40                  45

Glu Ile Val Glu Val Leu Leu Lys Asn Gly Ala Asp Val Asn Ala Lys
     50                  55                  60

Asp Asn Trp Gly Asp Thr Pro Leu His Leu Ala Ala Ile Phe Gly His
 65                  70                  75                  80

Leu Glu Ile Val Glu Val Leu Leu Lys Asn Gly Ala Asp Val Asn Ala
                85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln
        115                 120
```

<210> SEQ ID NO 61
<211> LENGTH: 121

<212> TYPE: PRT
<213> ORGANISM: Artificial Sequence
<220> FEATURE:
<223> OTHER INFORMATION: Synthetic DARPin I_07

<400> SEQUENCE: 61

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Ser Asp
                20                  25                  30

Lys Ser Gly Tyr Thr Pro Leu His Leu Ala Ala His Ile Gly His Leu
            35                  40                  45

Glu Ile Val Glu Val Leu Leu Lys His Gly Ala Asp Val Asn Ala His
        50                  55                  60

Asp Ser Trp Gly Asp Thr Pro Leu His Leu Ala Ala Thr Phe Gly His
65                  70                  75                  80

Leu Glu Ile Val Glu Val Leu Leu Lys His Gly Ala Asp Val Asn Ala
                85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln
        115                 120

<210> SEQ ID NO 62
<211> LENGTH: 154
<212> TYPE: PRT
<213> ORGANISM: Artificial Sequence
<220> FEATURE:
<223> OTHER INFORMATION: Synthetic DARPin I_11

<400> SEQUENCE: 62

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Ile Asp
                20                  25                  30

Thr Ile Gly Leu Thr Pro Leu His Leu Ala Ala His Asp Gly His Leu
            35                  40                  45

Glu Ile Val Glu Val Leu Leu Lys Asn Gly Ala Asp Val Asn Ala Ala
     50                  55                  60

Asp Asn Trp Gly Ile Thr Pro Leu His Leu Ala Ala Arg Arg Gly His
65                  70                  75                  80

Leu Glu Ile Val Glu Val Leu Leu Lys His Gly Ala Asp Val Asn Ala
                85                  90                  95

Asp Asp Val Gln Gly Asn Thr Pro Leu His Leu Thr Ala His His Gly
            100                 105                 110

His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 63
<211> LENGTH: 121
<212> TYPE: PRT
<213> ORGANISM: Artificial Sequence
<220> FEATURE:
<223> OTHER INFORMATION: Synthetic DARPin I_13

<400> SEQUENCE: 63

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
                20                  25                  30

Met Ser Gly Tyr Thr Pro Leu His Leu Ala Ala Tyr Asp Gly His Leu
            35                  40                  45

Glu Ile Val Glu Val Leu Leu Lys Asn Gly Ala Asp Val Asn Ala Asn
        50                  55                  60

Asp Leu Trp Gly Asp Thr Pro Leu His Leu Ala Ala Thr Arg Gly His
65                  70                  75                  80

Leu Glu Ile Val Glu Val Leu Leu Lys Tyr Gly Ala Asp Val Asn Ala
                85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln
        115                 120

<210> SEQ ID NO 64
<211> LENGTH: 154
<212> TYPE: PRT
<213> ORGANISM: Artificial Sequence
<220> FEATURE:
<223> OTHER INFORMATION: Synthetic DARPin I_19

<400> SEQUENCE: 64

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
                20                  25                  30

Asn Lys Gly Asp Thr Pro Leu His Leu Ala Ala Ser Phe Gly His Leu
            35                  40                  45

Glu Ile Val Glu Val Leu Leu Lys Asn Gly Ala Asp Val Asn Ala Asp
        50                  55                  60

Asp Tyr Phe Gly Asp Thr Pro Leu His Leu Ala Ala Trp Ser Gly His
65                  70                  75                  80

Leu Glu Ile Val Glu Val Leu Leu Lys Tyr Gly Ala Asp Val Asn Ala
                85                  90                  95

Gln Asp Gln Arg Gly Phe Thr Pro Leu His Leu Ala Ala Ile Ala Gly
            100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 65
<211> LENGTH: 154
<212> TYPE: PRT
<213> ORGANISM: Artificial Sequence
<220> FEATURE:
<223> OTHER INFORMATION: Synthetic DARPin T_01

<400> SEQUENCE: 65

Asp Leu Gly Lys Lys Leu Leu Glu Ala Ala Arg Ala Asp Gln Asp Asp
1               5                   10                  15

Glu Val Arg Ile Leu Met Ala Asn Gly Ala Asp Val Asn Ala Asn Asp
            20                  25                  30

Ile Trp Gly Ile Thr Pro Leu His Leu Ala Ala Ile Phe Gly His Leu
        35                  40                  45

Glu Ile Val Glu Phe Leu Leu Lys Asn Gly Ala Asp Val Asn Ala Ser
    50                  55                  60

Asp Phe Ser Gly Phe Thr Pro Leu His Leu Ala Ala Tyr Lys Gly His
65                  70                  75                  80

Leu Glu Ile Val Glu Val Leu Leu Lys His Gly Ala Asp Val Asn Ala
                85                  90                  95

Asn Asp Ala Thr Gly Thr Thr Pro Leu His Leu Ala Ala Lys Lys Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 66
<211> LENGTH: 154
<212> TYPE: PRT
<213> ORGANISM: Artificial Sequence
<220> FEATURE:
<223> OTHER INFORMATION: Synthetic DARPin T_02

<400> SEQUENCE: 66

Asp Leu Gly Lys Lys Leu Leu Glu Val Ala Arg Ala Gly Gln Asp Asp
1               5                   10                  15

Glu Val Arg Ile Leu Met Ala Asn Gly Ala Asp Val Asn Ala Ala Asp
            20                  25                  30

His Gln Ser Phe Thr Pro Leu His Leu Tyr Ala Ile Phe Gly His Leu
        35                  40                  45

Glu Ile Val Glu Val Leu Leu Lys Asn Gly Ala Asp Val Asn Ala Ser
    50                  55                  60

Asp Trp His Gly Asn Thr Pro Leu His Leu Ala Ala Trp Ile Gly His
65                  70                  75                  80

Leu Glu Ile Val Glu Val Leu Leu Lys Tyr Gly Ala Asp Val Asn Ala
                85                  90                  95

Thr Asp His Ser Gly Ser Thr Pro Leu His Leu Ala Ala Thr Leu Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 67
<211> LENGTH: 154
<212> TYPE: PRT
<213> ORGANISM: Artificial Sequence
<220> FEATURE:
<223> OTHER INFORMATION: Synthetic DARPin T_07

<400> SEQUENCE: 67

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Trp Lys Gly Leu Thr Pro Leu His Leu Ala Ala Ile Phe Gly His Leu
        35                  40                  45

Glu Ile Val Glu Ser Ala Met Lys Asn Gly Ala Asp Val Asn Ala Ile
    50                  55                  60

Asp Phe Ser Gly Arg Thr Pro Leu His Leu Ala Ala Leu Ile Gly His
65                  70                  75                  80

Leu Glu Ile Val Glu Val Leu Leu Lys Tyr Gly Ala Asp Val Asn Ala
                85                  90                  95

His Asp Ser Ala Gly Ser Thr Pro Leu His Leu Ala Ala Thr Lys Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 68
<211> LENGTH: 154
<212> TYPE: PRT
<213> ORGANISM: Artificial Sequence
<220> FEATURE:
<223> OTHER INFORMATION: Synthetic DARPin T_08

<400> SEQUENCE: 68

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Trp Asp
            20                  25                  30

Phe Leu Gly Leu Ile Pro Leu Arg Leu Ala Ala Ala Phe Gly His Leu
        35                  40                  45

Glu Ile Val Glu Val Leu Leu Lys Asn Gly Ala Asp Val Asn Ala Lys
    50                  55                  60

Asp Thr Tyr Gly Ile Thr Pro Leu His Leu Ala Ala Met Asn Gly His
65                  70                  75                  80

Leu Glu Ile Val Glu Val Leu Leu Lys Asn Gly Ala Asp Val Asn Ala
                85                  90                  95

Leu Asp Asn Thr Gly Ser Thr Pro Leu His Leu Ala Ala Asn Tyr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 69
<211> LENGTH: 154
<212> TYPE: PRT
<213> ORGANISM: Artificial Sequence
<220> FEATURE:
<223> OTHER INFORMATION: Synthetic DARPin T_09

<400> SEQUENCE: 69

Asp Leu Gly Lys Lys Leu Leu Glu Ala Ala Arg Ala Ser Gln Asp Asp

```
            1               5                  10                 15
       Glu Val Arg Ile Leu Met Ala Asn Gly Ala Asp Val Asn Ala Asn Asp
                       20                 25                 30

Phe Gln Gly Ile Thr Pro Leu His Leu Ala Ala Ile Phe Gly His Leu
                       35                 40                 45

Glu Ile Val Glu Val Leu Leu Lys Asn Gly Ala Asp Val Asn Ala Tyr
                       50                 55                 60

Asp Gln Met Gly Met Thr Pro Leu His Leu Ala Ala Trp Thr Gly His
       65                      70                 75                 80

Leu Glu Ile Val Glu Val Leu Leu Lys His Gly Ala Asp Val Asn Ala
                           85                 90                 95

Asp Asp Thr His Gly Ala Thr Pro Leu His Leu Ala Ala His Thr Gly
                          100                105                110

His Leu Glu Ile Val Glu Val Leu Leu Lys Tyr Gly Ala Asp Val Asn
                          115                120                125

Ala Gln Asp Lys Phe Gly Lys Thr Ala Phe Asp Ile Ser Ile Asp Asn
                          130                135                140

Gly Asn Glu Asp Leu Ala Glu Ile Leu Gln
       145                    150
```

<210> SEQ ID NO 70
<211> LENGTH: 154
<212> TYPE: PRT
<213> ORGANISM: Artificial Sequence
<220> FEATURE:
<223> OTHER INFORMATION: Synthetic DARPin T_16

<400> SEQUENCE: 70

```
       Asp Leu Gly Lys Lys Pro Leu Glu Ala Ala Arg Ala Gly Gln Asp Asp
       1               5                  10                 15

Glu Val Arg Ile Leu Met Ala Asn Gly Ala Asp Val Asn Ala Tyr Asp
                       20                 25                 30

Ile Val Gly Ile Thr Pro Leu His Leu Ala Ala Ile Phe Gly His Leu
                       35                 40                 45

Glu Ile Val Glu Val Leu Leu Lys Asn Gly Ala Asp Val Asn Ala Tyr
                       50                 55                 60

Asp Met Gln Val Asn Thr Pro Leu His Leu Ala Ala Trp Leu Gly His
       65                      70                 75                 80

Leu Glu Ile Val Glu Val Leu Leu Lys Asn Gly Ala Asp Val Asn Ala
                           85                 90                 95

Glu Asp Ser Tyr Gly Asn Thr Pro Leu His Leu Ala Ala Asp Lys Gly
                          100                105                110

His Leu Glu Ile Val Glu Val Leu Leu Lys Asn Gly Ala Asp Val Asn
                          115                120                125

Ala Gln Asp Lys Phe Gly Lys Thr Ala Phe Asp Ile Ser Ile Asp Asn
                          130                135                140

Gly Asn Glu Asp Leu Ala Glu Ile Leu Gln
       145                    150
```

<210> SEQ ID NO 71
<211> LENGTH: 154
<212> TYPE: PRT
<213> ORGANISM: Artificial Sequence
<220> FEATURE:
<223> OTHER INFORMATION: Synthetic DARPin T_25

<400> SEQUENCE: 71

```
Asp Leu Gly Lys Lys Leu Leu Glu Ala Ala Arg Ala Gly Gln Asp Asp
 1               5                   10                  15

Glu Val Arg Ile Leu Met Ala Asn Gly Ala Asp Val Asn Ala Asp Asp
            20                  25                  30

Arg Arg Gly Ile Pro Pro Leu His Leu Ala Ala Ile Phe Gly His Leu
        35                  40                  45

Glu Ile Val Glu Val Leu Leu Lys His Gly Ala Asp Val Asn Ala His
    50                  55                  60

Asp Met Gln Gly Arg Thr Pro Leu His Leu Ala Ala Tyr Thr Gly His
65                  70                  75                  80

Leu Glu Ile Val Glu Val Leu Leu Lys Tyr Gly Ala Asp Val Asn Ala
                85                  90                  95

Ile Asp Phe Thr Gly His Thr Pro Leu His Leu Ala Ala Phe Arg Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

<210> SEQ ID NO 72
<211> LENGTH: 154
<212> TYPE: PRT
<213> ORGANISM: Artificial Sequence
<220> FEATURE:
<223> OTHER INFORMATION: Synthetic DARPin T_27

<400> SEQUENCE: 72

```
Asp Leu Gly Lys Lys Pro Leu Glu Ala Ala Arg Ala Gly Gln Asp Asp
 1               5                   10                  15

Glu Val Arg Ile Leu Met Ala Asn Gly Ala Asp Val Asn Ala Tyr Asp
            20                  25                  30

Arg His Gly Leu Thr Pro Leu His Leu Val Ala Ile Phe Gly His Leu
        35                  40                  45

Glu Ile Val Glu Val Leu Leu Lys His Gly Ala Asp Val Asn Ala Ile
    50                  55                  60

Asp Ile Ile Gly Tyr Thr Pro Leu His Leu Ala Ala Trp Ser Gly His
65                  70                  75                  80

Leu Glu Ile Val Glu Val Leu Leu Lys Asn Gly Ala Asp Val Asn Ala
                85                  90                  95

Ser Asp Val Thr Gly Ser Thr Pro Leu His Leu Ala Ala Asp Lys Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

<210> SEQ ID NO 73
<211> LENGTH: 154
<212> TYPE: PRT
<213> ORGANISM: Artificial Sequence
<220> FEATURE:
<223> OTHER INFORMATION: Synthetic DARPin T_37

<400> SEQUENCE: 73

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
            20                  25                  30

Lys Arg Gly Ile Thr Pro Leu His Leu Ala Ala Ile Thr Gly His Leu
        35                  40                  45

Glu Met Val Glu Val Leu Leu Lys His Gly Ala Asp Val Asn Ala Val
    50                  55                  60

Asp Ile Gln Gly Arg Thr Pro Leu His Leu Ala Ala Trp Ile Gly His
65                  70                  75                  80

Leu Glu Ile Val Glu Val Leu Leu Lys Tyr Gly Ala Asp Val Asn Ala
                85                  90                  95

Met Asp Asp Phe Gly Glu Thr Pro Leu His Leu Ala Ala Arg Thr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 74
<211> LENGTH: 154
<212> TYPE: PRT
<213> ORGANISM: Artificial Sequence
<220> FEATURE:
<223> OTHER INFORMATION: Synthetic DARPin T_40

<400> SEQUENCE: 74

Asp Leu Gly Lys Lys Leu Leu Glu Ala Ala Arg Ala Ser Gln Asp Asp
1               5                   10                  15

Glu Val Arg Ile Leu Met Ala Asn Gly Ala Asp Val Asn Ala Asn Asp
            20                  25                  30

Arg Val Gly Phe Thr Pro Leu His Leu Ala Ala Met Phe Gly His Leu
        35                  40                  45

Glu Leu Val Glu Val Leu Leu Lys Asn Gly Ala Asp Val Asn Ala Ile
    50                  55                  60

Asp Phe Gln Gly Lys Thr Pro Leu His Leu Ala Ala Gln Leu Gly His
65                  70                  75                  80

Leu Glu Ile Val Glu Val Leu Leu Lys Tyr Gly Ala Asp Val Asn Ala
                85                  90                  95

Leu Asp Ala Arg Gly Ile Thr Pro Leu His Leu Ala Ala Ile His Gly
            100                 105                 110

His Pro Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 75
<211> LENGTH: 220
<212> TYPE: PRT
<213> ORGANISM: Artificial Sequence
<220> FEATURE:
<223> OTHER INFORMATION: Synthetic DARPin
<220> FEATURE:
```

<221> NAME/KEY: MOD_RES
<222> LOCATION: (1)..(220)
<223> OTHER INFORMATION: each Xaa is independently Ala, Ile, Leu, Met, Phe, Pro, Trp, Val, Asn, Cys, Gln, Gly, Ser, Thr, Tyr, Asp, Glu, Arg, His or Lys

<400> SEQUENCE: 75

Asp Leu Gly Lys Lys Leu Leu Glu Ala Ala Arg Ala Gly Gln Asp Asp
 1               5                  10                  15
Glu Val Arg Ile Leu Met Ala Asn Gly Ala Asp Val Asn Ala Xaa Asp
                20                  25                  30
Xaa Xaa Gly Xaa Thr Pro Leu His Leu Ala Ala Xaa Xaa Gly His Leu
         35                  40                  45
Glu Ile Val Glu Val Leu Leu Lys Xaa Gly Ala Asp Val Asn Ala Xaa
 50                  55                  60
Asp Xaa Xaa Gly Xaa Thr Pro Leu His Leu Ala Ala Xaa Xaa Gly His
 65                  70                  75                  80
Leu Glu Ile Val Glu Val Leu Leu Lys Xaa Gly Ala Asp Val Asn Ala
                85                  90                  95
Xaa Asp Xaa Xaa Gly Xaa Thr Pro Leu His Leu Ala Ala Xaa Xaa Gly
            100                 105                 110
His Leu Glu Ile Val Glu Val Leu Leu Lys Xaa Gly Ala Asp Val Asn
            115                 120                 125
Ala Xaa Asp Xaa Xaa Gly Xaa Thr Pro Leu His Leu Ala Ala Xaa Xaa
130                 135                 140
Gly His Leu Glu Ile Val Glu Val Leu Leu Lys Xaa Gly Ala Asp Val
145                 150                 155                 160
Asn Ala Xaa Asp Xaa Xaa Gly Xaa Thr Pro Leu His Leu Ala Ala Xaa
                165                 170                 175
Xaa Gly His Leu Glu Ile Val Glu Val Leu Leu Lys Xaa Gly Ala Asp
            180                 185                 190
Val Asn Ala Gln Asp Lys Phe Gly Lys Thr Ala Phe Asp Ile Ser Ile
            195                 200                 205
Asp Asn Gly Asn Glu Asp Leu Ala Glu Ile Leu Gln
    210                 215                 220

<210> SEQ ID NO 76
<211> LENGTH: 30
<212> TYPE: PRT
<213> ORGANISM: Artificial Sequence
<220> FEATURE:
<223> OTHER INFORMATION: Synthetic N-terminal polypeptide of anti-EGFR DARPin

<400> SEQUENCE: 76

Asp Leu Gly Lys Lys Leu Leu Glu Ala Ala Arg Ala Gly Gln Asp Asp
 1               5                  10                  15
Glu Val Arg Ile Leu Met Ala Asn Gly Ala Asp Val Asn Ala
                20                  25                  30

<210> SEQ ID NO 77
<211> LENGTH: 8
<212> TYPE: PRT
<213> ORGANISM: Artificial Sequence
<220> FEATURE:
<223> OTHER INFORMATION: Synthetic TEV site

<400> SEQUENCE: 77

Glu Asn Leu Tyr Phe Gln Gly Ser
 1               5

<210> SEQ ID NO 78
<211> LENGTH: 24
<212> TYPE: DNA
<213> ORGANISM: Artificial Sequence
<220> FEATURE:
<223> OTHER INFORMATION: Synthetic nucleotide sequence coding TEV site

<400> SEQUENCE: 78
gaaaacctgt attttcaggg atcc                                              24

<210> SEQ ID NO 79
<211> LENGTH: 4
<212> TYPE: PRT
<213> ORGANISM: Artificial Sequence
<220> FEATURE:
<223> OTHER INFORMATION: Synthetic linker

<400> SEQUENCE: 79

Gly Ser Gly Ser
  1

<210> SEQ ID NO 80
<211> LENGTH: 12
<212> TYPE: DNA
<213> ORGANISM: Artificial Sequence
<220> FEATURE:
<223> OTHER INFORMATION: Synthetic nucleotide sequence coding linker

<400> SEQUENCE: 80
ggcagcggca gc                                                           12

<210> SEQ ID NO 81
<211> LENGTH: 459
<212> TYPE: DNA
<213> ORGANISM: Artificial Sequence
<220> FEATURE:
<223> OTHER INFORMATION: Synthetic nucleotide sequence coding anti-EGFR
      DARPin

<400> SEQUENCE: 81
gatctgggca aaaaactgct ggaagcggcg cgcgcgggcc aggatgatga agtgcgcatt        60
ctgatggcga atggtgcgga tgttaacgcg gacgatacct ggggctggac cccactgcat       120
ctggccgcgt atcagggtca cctggaaatc gtggaggtgc tgctgaaaaa cggcgcggat       180
gtgaacgcgt atgattatat tggctggacc ccgctgcatc tggcggcgga tggccatctg       240
gaaattgtgg aagtgctgct gaaaaacggc gctgatgtta atgctagcga ttatattggc       300
gatacgccgc tgcacctggc agcgcataac ggccatctgg agattgttga agttctgctg       360
aagcatggcg ccgatgtgaa tgcgcaggat aaatttggca aaaccgcgtt tgatattagc       420
attgataacg gcaacgaaga tctggcggaa attctgcag                              459

<210> SEQ ID NO 82
<211> LENGTH: 30
<212> TYPE: DNA
<213> ORGANISM: Artificial Sequence
<220> FEATURE:
<223> OTHER INFORMATION: Synthetic nucleotide sequence coding MMP9

<400> SEQUENCE: 82
agcggcaaaa ttccgcgtac cctgaccgcg                                        30

<210> SEQ ID NO 83

```
<211> LENGTH: 48
<212> TYPE: DNA
<213> ORGANISM: Artificial Sequence
<220> FEATURE:
<223> OTHER INFORMATION: Synthetic nucleotide sequence coding MTS

<400> SEQUENCE: 83
gccgcggtag cgctgctccc ggcggtcctg ctggccttgc tggcgccc                    48

<210> SEQ ID NO 84
<211> LENGTH: 15
<212> TYPE: DNA
<213> ORGANISM: Artificial Sequence
<220> FEATURE:
<223> OTHER INFORMATION: Synthetic nucleotide sequence coding NLS

<400> SEQUENCE: 84
aaaaagaaga gaaag                                                        15

<210> SEQ ID NO 85
<211> LENGTH: 468
<212> TYPE: DNA
<213> ORGANISM: Artificial Sequence
<220> FEATURE:
<223> OTHER INFORMATION: Synthetic nucleotide sequence coding p16M7

<400> SEQUENCE: 85
atggaaccgg ctgctggcag ctctatggaa ccgtctgctg acaaactggc taccgctgct       60
gctcgtggtc gtgttgaaga agttcgtgct ctgctggaag ctggtgctga tccgaacgct      120
ccgaactctt acggtcgtcg tccgatccag gttatgatga tgggcagcgc tcgtgttgct      180
gaactgctgc tgaaacacgg tgctgaaccg aacagcgctg acccggctac cagcacccgt      240
ccggttcacg acgctgctcg tgaaggtttc ctggacaccc tggttgttct gcaccgtgct      300
ggtgctcgtc tggacgcgcg tgacgcttgg ggtcgtaccc cggttgacct ggctgaagaa      360
ctgggtcacc gtgacgttgc tcgttacctg cgtgctgctg ctggtggtac ccgtggcagc      420
aaccacgctc gtatcgacgc tgctgaaggt ccgtctgaca tcccggac                   468
```

FUSION PROTEIN COMPRISING TARGETING MOIETY, CLEAVAGE SITE, AND CELL MEMBRANE PENETRATING DOMAIN, AND USE THEREOF

CROSS-REFERENCE TO RELATED APPLICATIONS

This application claims the benefit of Korean Patent Application No. 10-2014-0085106 filed on Jul. 8, 2014, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 77,877 Byte ASCII (Text) file named "720738_ST25.TXT" created Jul. 6, 2015.

BACKGROUND OF THE INVENTION

1. Field

Provided is a fusion protein including a targeting moiety, a cleavage site, and a cell membrane penetrating domain, a conjugate including the fusion protein and a bioactive substance, and medical uses relevant to the fusion protein and/or the conjugate.

2. Description of the Related Art

Various technologies for intracellular delivery of macromolecules such as proteins have been developed and spotlighted as a new therapeutic strategy. However, they have difficulties in accurately targeting to target cells or target organs. To solve such problems, there have been many studies on cell membrane penetration of proteins.

A protein transduction domain (PTD) was first suggested on the ground of the finding that TAT protein from Human Immunodeficiency Virus 1 (HIV-1) can be delivered inside a cell when it is added to a cell culture medium. Thereafter, drosophila antennapedia (Antp) homeotic transcription factor and herpes simplex virus-1 DNA binding protein VP22 were also reported to be capable of penetrating a cell membrane, thereby being introduced into a cell.

Based on the fact that a fusion protein wherein PTDs are linked to other peptides or proteins can be delivered into a cell, various attempts have been made to transfer drugs, peptides, proteins, and the like, for therapeutic purpose, into a cell using the PTDs.

BRIEF SUMMARY OF THE INVENTION

Provided is a fusion protein including a targeting moiety, a cleavage site, and a cell membrane penetrating domain, wherein the targeting moiety is an antibody, antigen-binding antibody fragment, or protein scaffold that specifically binds to a cell-surface receptor; the cleavage site is a protease or peptidase recognition site; and the cell membrane penetrating domain is a membrane-translocation sequence, a macromolecule intracellular transduction domain, a fusion peptide comprising a hydrophobic peptide and a basic peptide, or a combination thereof.

Also provided is a conjugate including the fusion protein and a bioactive substance (bioactive molecule). The bioactive substance may be a tumor suppressor, for example, a p16 protein variant wherein p16 is modified so that it can possess an improved solubility with maintaining the binding affinity to Cdk4/6.

Further provided is a pharmaceutical composition including the fusion protein or conjugate and a carrier.

Also provided is a method for intracellular delivery of a bioactive substance including administering the conjugate comprising the bioactive substance to a subject

BRIEF DESCRIPTION OF THE DRAWINGS

FIGS. 8A to 8G illustrate the amino acid sequences of various DARPins corresponding to SEQ ID NOs: 44-75.

DETAILED DESCRIPTION OF THE INVENTION

Figure 1:
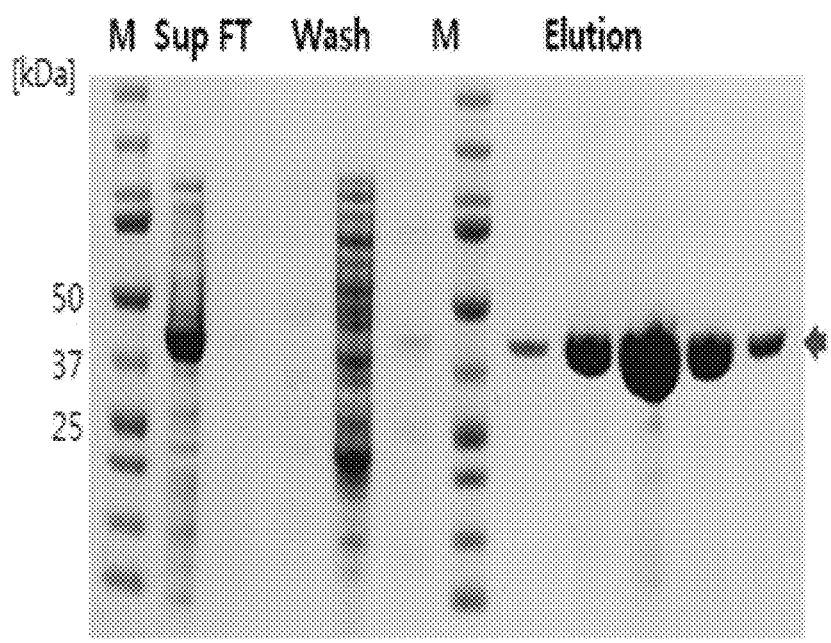
FIG. 1 is an immunoblot showing the expression and purification of an 'anti-EGFR DARPin-M9R-MTS-NLS-p16M7' conjugate.

Provided is a fusion protein, wherein a cell membrane penetrating domain and a targeting moiety are linked, thereby being delivered to a target cell with increased efficiency. In addition, the fusion protein may comprise a cleavage site between the cell penetrating peptide and the targeting moiety, where the cleavage site may be capable of being cleaved by an enzymatic activity in vivo. When the fusion protein is transferred to a target cell, the cleavage site may be cleaved, to release the cell membrane penetrating domain and the targeting moiety, thereby facilitating the intracellular delivery of the membrane penetrating domain. In addition, by conjugating a bioactive substance to the fusion protein, the targeting to a target cells and intracellular delivery of the bioactive substance can be more efficiently achieved.

Provided is a fusion protein comprising a targeting moiety, a cleavage site, and a cell membrane penetrating domain. In the fusion protein, the cleavage site may be located between the targeting moiety and the cell membrane penetrating domain, for example between the C-terminus of the targeting moiety and N-terminus of the cell membrane penetrating domain, or between the N-terminus of the targeting moiety and C-terminus of the cell membrane penetrating domain.

The targeting moiety may be a domain capable of specifically targeting a target cell or target tissue. For example, it may be a substance capable of targeting a specific cell such as a cancer cell or a specific tissue such as a cancer tissue. The targeting moiety may be at least one selected from the group consisting of an antibody, an antigen-binding fragment of an antibody, and a protein scaffold, but not limited thereto. In particular, the targeting moiety may be at least one selected from the group consisting of an antibody, an antigen-binding fragment of an antibody, and a protein scaffold, each of which independently and specifically recognizes and/or binds to one selected from the group consisting of cell surface receptors (e.g., receptor tyrosine kinase proteins, etc.) present or overexpressed specifically in a target cell (e.g., a cancer cell). The protein scaffold may be at least one selected from antibody-derived protein scaffolds and non-antibody-derived protein scaffolds, for example, a DARPin, a peptibody, a nanobody, an affibody, a binding peptide (e.g., peptide RGD or a peptide containing RGD (e.g., 4-20aa)), a lasso scaffold, a cyclotide, a knottin, an avimer (short for avidity multimer), a Kunitz domain, an anticalin, an adnectin, a pronectin, a fynomer, a nanofitin, an affilin, or any combination thereof.

Examples of the receptor tyrosine kinase protein may include receptors of various growth factors, and for example, be at least one selected from the group consisting of an ErbB family such as epidermal growth factor receptor (EGFR), HER2, HER3, etc., insulin receptor, platelet-derived growth factor receptor (PDGFR), fibroblast growth factor receptor (FGFR), vascular endothelial growth factor receptor (VEGFR), hepatocyte growth factor receptor (HGFR) such as c-Met, tropomyosin-receptor-kinase (Trk) receptor, Ephrin (Eph) receptor, AXL receptor, Leukocyte receptor tyrosine kinase (LTK) receptor, TIE receptor, receptor tyrosine kinase-like orphan (ROR) receptor, discoidin domain receptor (DDR), RET receptor, KLG receptor, related to receptor tyrosine kinase (RYK) receptor, Muscle-Specific Kinase (MuSK) receptor, and the like.

The antibody may be a monospecific or multispecific (e.g., bispecific) antibody which recognizes a cell surface receptor present or overexpressed in a target cell as described above, as an antigen. The antibody may refer to an antibody in an intact form of an immunoglobulin (e.g., IgA, IgD, IgE, IgG (IgG1, IgG2, IgG3, IgG4), or IgM), which comprises one to five large Y-shape dimers formed by linking two monomers where each monomer is formed by linking a heavy chain and a light chain. The antigen-binding fragment may be a polypeptide comprising a part of an antibody, which is responsible for specific binding to the antigen. The antigen-binding fragment refers to a polypeptide fragment of the antibody comprising a region specifically binding to an antigen, and may be a polypeptide comprising at least one heavy chain CDR (complementarity determining region), at least one light chain CDR, a heavy chain variable region, a light chain variable region, or any combination thereof (e.g., scFv, (scFv)2, scFv-Fc, Fab, Fab', or F(ab')2). In a particular embodiment, the targeting moiety may be an antigen-binding fragment of an antibody, such as scFv or scFv-Fc.

The protein scaffold is not an antibody but refers to a protein construct having a similar structure to an antibody or specifically recognizing and/or binding to a specific protein or a specific cell, and may be an antibody-derived protein scaffold, a non-antibody-derived protein scaffold, or a combination thereof. The protein scaffold may be fused (e.g., chemically linked) with an Fc fragment of an antibody to form a protein scaffold-Fc conjugate. The antibody-derived protein scaffold may be a protein construct having a similar structure to an antibody or an antigen-binding fragment thereof. A suitable protein scaffold includes, for example, a DARPin, a peptibody, a nanobody, an affibody, a binding peptide (e.g., peptide RGD or a peptide containing RGD (e.g., 4-20aa)), a lasso scaffold, a cyclotide, a knottin, an avimer (short for avidity multimer), a Kunitz domain, an anticalin, an adnectin, a pronectin, a fynomer, a nanofitin, an affilin, or any combination thereof.

DARPin (designed ankyrin repeat protein) refers to an antibody mimetic protein having high specificity and high binding affinity to a target protein, which is prepared via genetic engineering. DARPin is originated from natural ankyrin protein, and has a structure comprising at least 2 ankyrin repeat motifs, for example, comprising at least 3, 4 or 5 ankyrin repeat motifs. The DARPin can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively. DARPin includes a core part that provides structure and a target binding portion that resides outside of the core and binds to a target. The structural core includes a conserved amino acid sequence and the target binding portion includes an amino acid sequence that differs depending on the target.

Since the DARPin has high affinity to an antigen (target), and higher stability and smaller molecular weight compared to other antigen binding molecule such as an antibody fragment (e.g., scFv, (scFv)2, scFv-Fc, Fab, Fab', F(ab')2, or similar derivatives), it has advantageous properties (such as pharmacokinetic (PK) properties in the living body) and stability in the living body. In addition, the DARPin can be readily fused (e.g., via peptide bond; such as alpha-peptide bond) with other proteins. Therefore, the DARPin can be useful in preparing a fusion protein having excellent properties and stability in the body.

The fusion protein may comprise at least one DARPin, for example, about 1 to about 10, about 1 to about 5, or about 1 to about 3 DARPins, which include the same amino acid sequence, or at least two kinds of DARPins, for example, about 2 to about 10, about 2 to about 5, or about 2 to about 3 kinds of DARPins, which include different amino acid sequences from one another and target the same or different antigens.

Examples of DARPins (by clone ID no.) are summarized in the following table, and nucleotide sequences of the clones encoding the DARPins are illustrated in FIGS. 8A to 8G and SEQ ID NOs: 44-75:

| Target protein | DARPin Clone ID |
| --- | --- |
| Human IgG1-Fc | I_01/02/07/11/13/19 |
| TNF-alpha | T_01/02/07/08/09/16/25/27/37/40 |
| ErbB1 (EGFR) | E_01/67/68/69 |
| ErbB2 (1-509) | 9_16/26/29 |
| ErbB2 (1-631) | H_14 |
| ErbB4 | B4_01/02/07/33/45/50/58 |
| CitS | cp34_15/16 |

The targeting moiety may be an anti-EGFR DARPin which targets EGFR. The anti-EGFR DARPin may be any DARPin having DARPin's own unique structure and capable of specifically binding to EGFR. In one embodiment, the anti-EGFR DARPin may comprise, consist essentially of, or consist of a polypeptide of about 50-300 amino acids, about 100-250 amino acids, about 130-230 amino acids, or about 150-200 amino acids, which essentially comprise the amino acid sequence of "dlgkklleaaragqd-devrilmangadvna" (SEQ ID NO: 76) at the N-terminus. For example, the anti-EGFR DARPin may be at least on selected from the group consisting of the following 4 anti-EGFR DARPins:

```
Anti-EGFR DARPin (anti-EGFR DARPin-0;
SEQ ID NO: 7)
dlgkklleaaragqddevrilmangadvnaddtwgwtplhlaayqghlei vevllkngadvnaydyigwtplhlaadghleivevllkngadvnasdyig dtplhlaahnghleivevllkhgadvnaqdkfgktafdisidngnedlae ilq Anti-EGFR DARPin (Anti-EGFR DARPin-67;
SEQ ID NO: 8)
dlgkklleaaragqddevrilmangadvnatdndgntplhlsawighlei vevllkhgadvnaddllgmtplhlaadtghleivevllkygadvnardtr gktplhlaardghleivevllkhdadvnaqdkfgktafdisidngnedla eilq Anti-EGFR DARPin (Anti-EGFR DARPin-68;
SEQ ID NO: 9)
dlgkklleaaragqddevrilmangadvnafdywgmtplhlaadnghlei vevllkhgadvnasdnfgftplhlaafyghleivevllkhgadvnafdmw gntplhlaaqnghleivevllkngadvnaqdkfgktafdisidngnedla eilq Anti-EGFR DARPin (Anti-EGFR DARPin-69;
SEQ ID NO: 10)
Dlgkklleaaragqddevrilmangadvnaddnagrtplhlaanfghlei vevllkngadvnakghhentplhlaawaghleivevllkygadvnaddde gytplhlaadigdleivevllkygadvnawdmygrtplhlaasaghleiv evllkygadvnaqdkfgktafdisidngnedlaeilq.
```

Term "peptibody (peptide+antibody)" may refer to a fusion protein wherein a peptide is fused with the whole or a part of a constant region of an antibody, such as Fc region, and the peptide acts as an antigen-binding region (e.g., a CDR or variable region of a heavy chain and/or light chain), thereby having a structure and functions similar to an antibody.

Term "nanobody" that is also called as a single-domain antibody, may refer to an antibody fragment including a single variable domain in a monomeric form and selectively binding to a specific antigen, similarly to an antibody in a complete form. The nanobody usually has a molecular weight of about 12 kDa to about 15 kDa, which is much smaller than an general molecular weight (about 150 kDa to about 160 kDa) of an antibody in a complete form (including two heavy chains and two light chains), and in some case, smaller than a molecular weight of a Fab fragment or a scFv fragment.

The term "affibody", which is one class of antibody mimetics prepared by imitating monoclonal antibodies, refers to a small molecular protein with high affinity to a specific target protein or a specific target peptide. The original affibody protein scaffold was designed based on the Z domain (the immunoglobulin G binding domain) of protein A. In contrast to antibodies, the affibody molecules are composed of alpha helices and lack disulfide bridges.

The cleavage site refers to a restriction site (or region) (recognition site or region of a peptide) recognized by a cleavage enzyme such as a peptidase or a protease present in a living body or a specific cell, for example, a tumor cell (e.g., a cancer cell). The peptidase or protease present specifically in a cancer cell may be a tumor cell-specific cleavage enzyme which is secreted specifically from a tumor cell or located specifically on the cell membrane of a cancer cell (e.g., exposed to outside of cell membrane), for example, endopeptidase. The cleavage site may be any recognition (or restriction) site of the tumor cell-specific cleavage enzyme. For example, the cleavage site may be a recognition (or restriction) site (i.e., tumor specific cleavage site) of a tumor cell-specific cleavage enzyme, wherein the tumor cell-specific cleavage enzyme may be at least one selected from the group consisting of matrix metalloproteinase (MMP; e.g., MMP1, MMP2, MMP3, MMP1, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27, MMP28, etc.), cathepsin (e.g., cathepsin C, cathepsin H, etc.; cleaving the site of cysteine, serine or aspartic acid), urokinase-type plasminogen activator (uPA), and the like, or any combination thereof. In a particular example, the cleavage site may be a recognition site of MMP9 (e.g., SGKIPRTLTA (SEQ ID NO: 26; wherein the cleavage position is underlined), SGKGPRQITA (SEQ ID NO: 27), SGPRAVSTTA (SEQ ID NO: 28), etc.), but not be limited thereto.

When the cleavage site is a recognition (or restriction) site of a cleavage enzyme specifically present in a tumor cell, such as MMP, cathepsin, uPA, and the like, it can be cleaved specifically in a tumor cell, thereby promoting a tumor specific translocation with high efficiency.

The cell membrane penetrating domain may be any peptide or proteins capable of penetrating a cell membrane. For example, the cell membrane penetrating domain may be at least one selected from the group consisting of a membrane-translocation sequence (MTS), a macromolecule intracellular transduction domain (MTD), and a fusion peptide of a hydrophobic peptide and a basic peptide, or any combination thereof.

For example, the membrane-translocation sequence may be at least one selected from the group consisting of AAVALLPAVLLALLAP (SEQ ID NO: 11), a peptide fragment comprising or consisting of 7 to 16 consecutive amino acids within the amino acid sequence of SEQ ID NO: 11 (e.g., AAVALLP (SEQ ID NO: 12) or AVLLALLAP (SEQ ID NO: 13)), AVLLALLAA (tMTS; SEQ ID NO: 14), AAVALLPAVLLALLAA (SEQ ID NO: 15), TAT (RKKRRQRRR; SEQ ID NO: 38), TP10(AGYLLGKINLKA-LAALAKKIL; SEQ ID NO: 39), Penetratin (RQIKIWFQN-RRMKWKK; SEQ ID NO: 40), R9 (RRRRRRRRR; SEQ ID NO: 41), and MAP (KLALKLALKALKAALKLA; SEQ ID NO: 42), or any combination thereof. The macromolecule intracellular transduction domain may be a peptide comprising the amino acid sequence of LALPVLLLA (MTD103; SEQ ID NO: 25).

The fusion peptide of a hydrophobic peptide and a basic peptide may comprise or consisting essentially of:
a hydrophobic peptide comprising a total of about 5 to about 100 amino acids, about 5 to about 50 amino acids, about 5 to about 40 amino acids, or about 6 to about 30 amino acids, and comprising hydrophobic amino acids at a ratio of about 60% or more, about 70% or more, about 80% or more, or about 90% or more, for example, about 60 to about 100%, about 70 to about 100%, about 80 to about 100%, or about 90 to about 100%, based on the number of the total amino acids in the hydrophobic peptide; and a basic peptide, which consists of basic amino acids, comprising, consisting, or consisting essentially of a basic peptide unit including about 1 to about 6 basic amino acids (e.g., about 2 to about 6 basic amino acids), or a repeat including 2 to 6 basic peptide units.

The hydrophobic peptide comprises hydrophobic amino acids, which may include glycine, alanine, valine, leucine, isoleucine, methionine, proline, tryptophan, phenylalanine, and the like. That is, each hydrophobic amino acid of the hydrophobic peptide may be independently selected from the group consisting of glycine, alanine, valine, leucine, isoleucine, methionine, proline, tryptophan, phenylalanine, and the like. The hydrophobic peptide may comprise one kind or two or more different kinds of hydrophobic amino acids selected from the hydrophobic amino acid group described above. When the hydrophobic peptide includes one kind of hydrophobic amino acid, the hydrophobic amino acid may be included once or repeatedly. In one embodiment, the hydrophobic peptide may not include any basic amino acids.

The hydrophobic peptide may be at least one selected from the group consisting of a membrane translocation sequence (MTS; for example, AAVALLPAVLLALLAP (SEQ ID NO: 11)), a peptide fragment of the MTS (for example, a peptide fragment including 7 to 16 consecutive amino acids within the amino acid sequence of SEQ ID NO: 11; e.g., AAVALLP (SEQ ID NO: 12), AVLLALLAP (SEQ ID NO: 13), etc.), a peptide including the amino acid sequence of AVLLALLAA (tMTS; SEQ ID NO: 14), and a peptide including the amino acid sequence of AAVALLPAVLLALLAA (SEQ ID NO: 15), or any combination thereof.

The basic peptide may comprise, consisting essentially of or consisting of 1 to 6 basic amino acids (e.g., 2 to 6 basic amino acids). In a particular embodiment, the basic peptide may include lysine (K), arginine (R), or a combination thereof, with 1 to 6 amino acid length. In an embodiment, the basic peptide may be at least one selected from nuclear localization sequences (NLS). For example, the basic peptide may be at least one selected from the group consisting of KKKRK (SEQ ID NO: 16), KKKR (SEQ ID NO: 17), RKRK (SEQ ID NO: 18), RKRKRK (SEQ ID NO: 19), KKKKK (SEQ ID NO: 20), KKKKKR (SEQ ID NO: 21), KKKKKR (SEQ ID NO: 22), R5 (RRRRR; SEQ ID NO: 23), and R6 (RRRRRR; SEQ ID NO: 24), or any combination thereof, but not be limited thereto. Some of the basic peptides have been known to have a nuclear membrane penetrating activity; however, none of them has been known to have a cell membrane penetrating activity. In the present disclosure, the basic peptide is fused (e.g., linked) with a hydrophobic peptide (e.g., via a peptide bond), to produce a fusion peptide, thereby considerably increasing the cell membrane penetrating effect of the hydrophobic peptide or the fusion peptide.

When the basic peptide is conjugated (e.g., fused or chemically linked, such as by a covalent bond)) with the hydrophobic peptide to form a fusion peptide, a considerably increased cell membrane penetrability of the basic peptide or the fusion peptide can be achieved.

A basic peptide may be linked (e.g., covalently) to the N-terminus or the C-terminus of the hydrophobic peptide, or linked to both of the N-terminus and the C-terminus of the hydrophobic peptide (when two or more basic peptides are included). In some embodiments, a basic peptide may be linked to the C-terminus, of the hydrophobic peptide. The basic peptide may be linked to the N-terminus or the C-terminus of the hydrophobic peptide in a forward direction (i.e., the N-terminus of the basic amino acid is linked to the C-terminus of the hydrophobic peptide, or the C-terminus of the basic amino acid is linked to the N-terminus of the hydrophobic peptide), or in a reverse direction (i.e., the C-terminus of the basic amino acid is linked to the C-terminus of the hydrophobic peptide, or the N-terminus of the basic amino acid is linked to the N-terminus of the hydrophobic peptide). In an embodiment, the basic peptide may be linked to the N-terminus or the C-terminus, for example the C-terminus, of the hydrophobic peptide, in forward direction. When two or more basic peptides are respectively linked to both termini of the hydrophobic peptide, the basic peptides may be the same as or different from one another.

The fusion peptide of a hydrophobic peptide and a basic peptide may play a role in cell membrane penetration (cell membrane transfer). The term "cell membrane penetration" (cell membrane transfer) or "cell membrane penetrability" may refer to transporting a substance into of a cell by passing through a cell membrane with a lipid bilayer ex vivo and/or in vivo.

In a particular embodiment, the fusion peptide may comprise or consist essentially of:

a hydrophobic peptide and a basic peptide which is linked to the C-terminus of the hydrophobic peptide (that is, in the fusion peptide, a hydrophobic peptide is located at a N-terminal part and a basic peptide is located at a C-terminal part), or a hydrophobic peptide and a basic peptide which is linked to N-terminus of the hydrophobic peptide (that is, in the fusion peptide, a hydrophobic peptide is located at a C-terminal part and a basic peptide is located at a N-terminal part.

To further increase the cell membrane penetrability of the fusion peptide, the fusion peptide may comprise or consist essentially of a hydrophobic peptide and a basic peptide which is linked to the C-terminus of the hydrophobic peptide.

In a particular embodiment, the fusion peptide may comprise or consist essentially of the amino acid sequence of SEQ ID NO: 30 ("MST-NLS").

In a particular embodiment, the fusion protein comprising the targeting moiety, cleavage site, and cell membrane penetrating domain may comprise or consist essentially of the amino acid sequence of SEQ ID NO: 35 ("anti-EGFR DARPin-M9R-MTS-NLS-p16M7").

The fusion protein comprising a targeting moiety, a cleavage site, and a cell membrane penetrating domain may possess an increased transfer efficiency to a target cell (e.g., a tumor cell) due to the targeting moiety, and when the fusion protein is transferred to a target cell, the cleavage site located between the targeting moiety and the cell membrane penetrating domain is cleaved to release (or separate) the cell membrane penetrating domain from the targeting moiety, whereby the cell membrane penetrating domain can be more easily transferred to inside of a target cell. When a bioactive substance is linked (e.g., covalently) to the fusion protein, the bioactive substance can be more efficiently delivered to or into a desired target cell. In particular, when the targeting moiety is tumor specific, the bioactive substance contained in the fusion protein can be delivered specifically to a tumor cell, thereby increasing its anticancer effect. Therefore, the fusion protein may be useful for a medical use, e.g., an intracellular delivery of a bioactive substance.

Therefore, also provided is a pharmaceutical composition including the fusion protein comprising a targeting moiety, a cleavage site, and a cell membrane penetrating domain. In a particular embodiment, a pharmaceutical composition for cell membrane penetrating comprising the fusion protein is provided. In another particular embodiment, a pharmaceutical composition for intracellular delivery comprising the fusion protein is provided.

Also provided is a conjugate comprising or consisting essentially of a bioactive substance and a fusion protein comprising or essentially consisting of a targeting moiety, a cleavage site, and a cell membrane penetrating domain. In the conjugate, upon reaching a target cell, in order to be more easily released from the targeting moiety and more efficiently delivered to a target cell, the bioactive substance may be linked (e.g., covalently) to the cell membrane penetrating domain in the fusion protein. For example, in the conjugate, the bioactive substance may be located at a part which is not a binding site of the cell membrane penetrating domain and the cleavage site, e.g., at other side of a binding region of the cell membrane penetrating domain and the cleavage site, or between the cell membrane penetrating domain and the cleavage site. In a particular embodiment, the conjugate may comprise or consist essentially of a targeting moiety, a cleavage site linked (e.g., covalently) to the C-terminus of the targeting moiety, a cell membrane penetrating domain linked (e.g., covalently) to the C-terminus of the cleavage site, and a bioactive substance linked (e.g., covalently) to the cell membrane penetrating domain.

When the cell membrane penetrating domain is a fusion peptide of a hydrophobic peptide and a basic peptide, the conjugate may contain a bioactive substance at the N-terminus or the C-terminus of the fusion peptide or between the hydrophobic peptide and the basic peptide. In order to more increase the cell membrane penetrability, the bioactive substance may be linked (e.g., covalently via covalent bond, such as alpha-peptide bond) to the N-terminus or the C-terminus of the fusion peptide (e.g., between the fusion peptide and the cleavage site), for example, to the C-terminus of the fusion peptide.

The conjugate may further comprise a nuclear membrane penetrating peptide comprising or consisting of a basis peptide that is distinct from the basic peptide of the cell membrane penetrating domain comprised in the fusion peptide. The nuclear membrane penetrating peptide can be positioned at an N-terminal side and/or a C-terminal side of the conjugate, or inside the conjugate, in addition to the targeting moiety, the cleavage site, the cell membrane penetrating domain and the bioactive substance. The features of the basic peptide used as the nuclear membrane penetrating peptide are as described above description with respect to the basic peptide included in the fusion peptide. If the conjugate comprises a fusion peptide as a cell membrane penetrating domain, the nuclear membrane penetrating peptide may be the same (e.g., has the same amino acid sequence) or different (e.g., has a different amino acid sequence) from the basic peptide included in the fusion peptide in the conjugate. In this case, the nuclear membrane penetrating peptide may be contained at the N-terminus, the C-terminus, or both termini of the conjugate, or between (at the junction or linking part of) the fusion peptide and the bioactive substance. In a particular embodiment, the conjugate may comprise or consist essentially of a targeting moiety, a cleavage site linked (e.g., covalently) to the C-terminus of the targeting moiety, a hydrophobic peptide linked to the C-terminus of the targeting moiety, a basic peptide linked (e.g., covalently) to the C-terminus of the hydrophobic peptide, a bioactive substance linked (e.g., covalently) to the C-terminus of the basic peptide, and optionally, a nuclear membrane penetrating peptide linked (e.g., covalently) to the C-terminus of the bioactive substance (in case the bioactive substance is a peptide or a protein).

Also provided is a composition for cell membrane penetration or intracellular delivery of a bioactive substance, which comprises the conjugate comprising a fusion protein and a bioactive substance.

Yet further provided is a method of cell membrane penetration or intracellular delivery of a bioactive substance, which comprises administering the conjugate comprising a fusion protein and a bioactive substance to a subject. The method may further comprise a step of identifying a subject in need of delivery (e.g., intracellular delivery) of the substance of interest included in the cell membrane penetrating conjugate, prior to the administration step.

The subject may be any animal selected from mammals such as primates including human, monkeys, etc., rodents including rats, mice, etc., and the like; or a cell, a tissue, or body fluid (e.g., serum) derived (isolated) from the animal or a culture thereof. The subject may be an animal, or a cell, a tissue, or body fluid derived (isolated) from the animal (living body), which is in need of delivery (e.g., intracellular delivery) of the bioactive substance included in the conjugate.

The conjugate may be administered to a subject in need of administration of the bioactive substance, via oral or parenteral route, or administered by being contacted with a cell, tissue, or body fluid isolated from a living body.

The bioactive substance may be any substance which is required to be delivered into a cell for various purposes such as treatment, diagnosis, and the like. The bioactive substance may refer to any biocompatible substances capable of functioning and exhibiting advantageous effects in vivo or ex vivo. The bioactive substance may be at least one selected from the group consisting of various proteins, peptides, nucleic acids (e.g., DNA, RNA, siRNA, shRNA, microRNA, etc.), small-molecule chemical drugs (e.g., any chemicals except proteins, peptide, and nucleic acids), contrast materials, and the like, and for example, the bioactive substance may be at least one selected from the group consisting of proteins and peptides. When the bioactive substance is a protein and/or a peptide, it may be linked with the fusion protein via a peptide bond.

A bioactive protein may be at least one selected from the group consisting of any bioactive proteins having a molecular weight of about 2 KDa to about 150 KDa, and for example, the protein may be at least one selected from the group consisting of antibodies (e.g., at least one selected from the group consisting of IgA, IgD, IgG (e.g., IgG1, IgG2, IgG3, or IgG4), IgE, IgM, and the like), antigen-binding fragments of the antibodies (e.g., at least one selected from the group consisting of scFv, scFvFc, (scFv)$_2$, Fab, Fab', F(ab')$_2$, and the like), hormones, hormone analogues, enzymes, tumor suppressor, signal transduction proteins, receptors, adhesion proteins, structural proteins, regulatory proteins, toxoproteins, cytokines, transcription factors, hemocoagulation factors, and the like.

A bioactive peptide may include at least 2 amino acids, for example, about 5 to about 100 amino acids, about 10 to about 50 amino acids, or about 15 to about 45 amino acids. The peptide may be at least one selected from the group consisting of (D)pMI-alpha(TNWYANLEKLLR; SEQ ID NO: 32), (D)pMI-beta (TAWYANFEKLLR; SEQ ID NO: 33), p53 fragment (SQETFSDLWKLLPEN; SEQ ID NO: 34), various growth factors, aptamers including about 10 to about 50 amino acids or about 15 to about 45 amino acids, and the like, or a combination thereof.

In a particular embodiment, the bioactive peptide or protein may be at least one selected from the group consisting of p15, p16, p18, p53, p21, p25, p57, p16 variants (e.g., SEQ ID NO: 2, etc.), NIP71, neuroregulin 1, PTEN (phosphatase and tensin homolog) tumor suppressor, ARF tumor suppressor, APC, CD95, folliculin, MEN1 (menin), BRCA1, Von Hippel-Lindau tumor suppressor, RKIP (Raf kinase inhibitor protein), nm23, endostatin, insulin, IGF-1 (insulin-like growth factor 1), growth hormones, erythropoietin, G-CSFs (granulocyte-colony stimulating factors), GM-CSFs (granulocyte/macrophage-colony stimulating factors), interferon-alpha, interferon-beta, interferon-gamma, interleukin-1 alpha, interleukin-1 beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II(GHRH-II), gonadorelin, goserelin, histrelin, leuprorelin, lypressin, octreotide, oxytocin, pitressin, secretin, sincalide, terlipressin, thymopentin, thymosine al, triptorelin, bivalirudin, carbetocin, cyclosporine, exedine, lanreotide, luteinizing hormone-releasing hormone (LHRH), nafarelin, parathyroid hormone (PTH), pramlintide, T-20 (enfuvirtide), thymalfasin, ziconotide, (D)pMI-alpha (TNWYANLEKLLR; SEQ ID NO: 32), (D)pMI-beta (TAWYANFEKLLR; SEQ ID NO: 33), p53 fragment (SQETFSDLWKLLPEN; SEQ ID NO: 34), and the like, and a combination thereof.

The nucleic acids may be single-stranded or double-stranded one in lengths of about 1 to about 100 bp, about 2 to about 70 bp, about 5 to about 50 bp, or about 10 to about 40 bp, and may be at least one selected from the group consisting of DNAs, RNAs, small interfering RNAs (siRNAs), small hairpin RNAs (shRNAs), micro RNAs (miRNAs), and the like, or a combination thereof.

The chemical drug may be any chemical element (e.g., a radioisotope) or any small-molecule compound (except proteins, peptide, and nucleic acids) having a molecular weight of about 2 KDa to about 150 KDa, which is capable of being used for treating, alleviating, improving, diagnosing, and/or regulating various diseases. For example, the chemical drug may be at least one selected from the group consisting of various radioisotopes, anti-cancer agents, anti-inflammatory agents, immune-regulatory agents, and the like, such as nutilin 3a, PD0332991, monomethyl auristatin E (MMAE), emtansine (DM1), pyrrolobenzodiazepine (PBD), SN38 (CAS#: 86639-52-3; (S)-4,11-diethyl-4,9-dihydroxy-1H-pyrano[3',4': 6,7] indolizino[1,2-b] quinoline-3,14(4H, 12H)-dione), doxorubicin (DOX), docetaxel, paclitaxel, or the like.

The contrast material may be any compound having a molecular weight of about 2 KDa to about 150 KDa, capable of being used for the visualization of cells. For example, the contrast material may be at least one selected from the group consisting of endosome markers (e.g., anti-EEA1 (early endosome antigen) antibody, mannose-6-phosphate receptor, anti-Rab4 antibody, anti-Rab5 antibody, anti-LAMP-1 (lysosome-associated membrane protein-1) antibody, etc.), golgi markers (e.g., anti-58K golgi protein antibody, anti-mannosidase II antibody, etc.), Cre recombinase (e.g., DQ023272.1, etc.), integrase (e.g., phiC31, X59938, etc.), and the like, or a combination thereof. The markers and/or enzymes may be in a form of conjugate which is conjugated with a coloring material, a fluorescent material, or a luminous material.

Kinds and properties of radioisotopes available for therapy of a disease or cell visualizing are well known in the relevant arts. On the basis of the knowledge of the art, selection may be made of appropriate radioisotopes according to purposes. Representative radioisotopes are summarized, together with their properties, in Table 1, below:

TABLE 1

| Radioisotope | Representative | Description |
|---|---|---|
| Gallium | Gallium-67 | Produced in an accelerator. Used for medicinal diagnosis such as to image tumors and inflammation |
| | Gallium-68 | Produced in a generator (Ge-68). Positron emitting isotope for use in PET, and PET/CT |
| Copper | Copper-64 | Produced in an accelerator. Used in the imaging analysis of the effect of copper metabolism on genetic diseases, and the imaging analysis and treatment of Wilson and Menke diseases, and tumor. |
| | Copper-67 | Produced in an accelerator. Used in tumor treatment, injected together with monoclonal antibody into tumors so as to kill tumors and help the antibody act in tumors |
| Dysprosium | Dysprosium-165 | Produced in a nuclear reactor. Used to aggregate hydroxides for radiosynovectomy |
| Rhenium | Rhenium-186 | Produced in a nuclear reactor. Used to perform treatment and diagnosis simultaneously because of simultaneous emitting of beta and gamma radiation, relieving the pain of bone cancer. |
| | Rhenium-188 | Produced in a nuclear reactor. Used to irradiate beta radiation on the coronary artery upon vascular surgery |
| Rubidium | Rubidium-82 | Produced in a generator (Sr-82). Myocardial perfusion imaging, PET mechanism |
| Lutetium | Lutetium-177 | Produced in a nuclear reactor. Half life of 6.7. Emitting of beta/gamma radiation, prepared from Lu-176. Simultaneous diagnosis/treatment, intracranial treatment, relieving arthritis pain on synovial membrane extension |
| Fluorine | Florine-18 | Produced in an accelerator. Used as a tracer, a positron-emitting isotope for FLT, F-miso, and PET in the study of cerebral physiology and pathogenesis, such as in epilepsy, dementia, psychosis, etc. |
| Bismuth | Bismuth-213 | Produced in a nuclear reactor. Half life of 46 ⏃. High energy (8.4 MeV) used to treat cancer by an alpha targeting method |
| Samarium | Samarium-153 | Produced in a nuclear reactor. Relieving pain of secondary cancer within bone, effective for treatment of prostate cancer and breast cancer |

TABLE 1-continued

| Radioisotope | Representative | Description |
|---|---|---|
| Oxygen | Oxygen-15 | Produced in an accelerator, a positron emitting isotope for PET, used in the study of cerebral physiology and pathology, such as in epilepsy, dementia, psychosis, etc. |
| Cesium | Cesium -137 | Produced in a nuclear reactor. Tumor treatment, measurement of accurate radiation doses to patients, intracranial treatment, relieving arthritis pain upon synovial membrane extension |
| Strontium | Strontium-85 | Used in the study of bone structure and metabolism |
|  | Strontium-89 | Produced in a nuclear reactor. Beta radiation emitting radionuclide, effective for pain relief of prostate cancer and bone cancer. |
| Iodine | Erbium-169 | Produced in a nuclear reactor. Relieving arthritis pain at synovitis arthritis |
| Iodine | Iodine-123 | Produced in an accelerator. Used in the treatment of thyroid grand disease, brain disease, and other metabolic diseases |
|  | Iodine-125 | Produced in a nuclear reactor. Used in the treatment of prostate cancer, intracranial treatment, the estimation and diagnosis of prostate cancer clearance, the diagnosis of leg thrombosis, and as radiation diagnosis reagent for clinical trial, and thyroid disease. Applied to biomedical study |
|  | Iodine-131 | Produced in a nuclear reactor. Diagnosis and treatment of thyroid cancer, diagnosis of abnormal liver function, impaired bladder functions, and renal blood flow |
| Ytterbium | Ytterbium-169 | Produced in a nuclear reactor. Used in the study of cerebrospinal fluid, and to obtain gamma images in NDT |
| Yttrium | Yttrium-90 | Produced in a nuclear reactor. Intracranial treatment. Relieving pain of arthritis upon synovial membrane extension, Ce, Au, Ru also used |
| Gold | Au-198 | Applied to vessels or tissues to obtain images. Intracranial treatment, Relieving pain of arthritis upon synovial membrane extension |
| Phosphorus | Phosphorus-32 | Produced in a nuclear reactor. Used in the treatment of polycythemia, and the molecular biology and genetics study |
| Indium | Indium-111 | Produced in an accelerator. Used in the study of brain diseases, rectal diseases, infections, special diagnosis, etc. |
| Germanium | Germanium-68 | Produced in an accelerator. PET, Ga-68 generator |
| Nitrogen | Nitrogen-13 | Produced in an accelerator. Positron emitting isotope for PET. Used in the study of cerebral physiology and pathogenesis, such as in epilepsy, dementia, psychosis, etc. |
| Cobalt | Cobalt-57 | Produced in an accelerator. Used as a maker for inferring organ sizes, an intrapulmonary diagnostic reagent, and a tracer for diagnosis of pernicious anemia |
|  | Cobalt-60 | Produced in a nuclear reactor. External radiation source, used to sterilize surgical instruments, improve the reliability and safety of industrial periroleum bunners, and investigate foods, and in radiographic examination |
| Krypton | Krypton-81: | Produced in a generator (Rh-81). Images of the lung of asthma patients, diagnosis of lung function and diseases |
| Carbon | Carbon-11 | Produced in an accelerator. Positron emitting isotope for PET, used in the study of cerebral physiology and pathogenesis, such as in epilepsy, dementia, psychosis, etc. |
| Thallium | Thallium-201 | Produced in an accelerator. Used in nuclear medicine for heart diseases and tumors |
| Technetium | Technetium-99m | Produced in a generator (inclusive of Mo-99). Nuclear medicine diagnosis, radiopharmaceuticals. Used as different forms in the study of brain, bone, liver, kidney, and blood flow |
| Palladium | Palladium-103 | Produced in a nuclear reactor. Treatment of early prostate cancer. Radiation source for permanent skin graft |
| Potassium | Potassium-42 | Produced in a nuclear reactor. Used to determine potassium change in coronary flow |
| Holmium | Holmium-166 | Produced in a nuclear reactor. Diagnosis and treatment of liver cancer |

The bioactive substance may be a p16 protein variant. The p16 protein variant is characterized by an improvement in solubility, with maintaining affinity for Cdk4/6, by a mutation (e.g., substitution) on at least one selected from amino acids at such positions that they are exposed externally (e.g., to aqueous environment) on the three dimensional structure of the intact protein and irresponsible for binding to Cdk4/6.

p16 is a cyclin-dependent kinase (CDK) inhibitor functioning to arrest the cell cycle by inactivating CDKs that phosphorylate retinoblastoma protein (Rb). With this function, p16 contributes to prevention of the infinite division of cells to the development of cancer cells, and therefor acts as a tumor suppressor.

The p16 protein may be originated from mammals including primates, such as humans, monkeys and the like; and rodents, such as mice, rat, and the like. For example, the p16 may be a human p16 protein (SEQ ID NO: 1), a mouse p16 protein (SEQ ID NO: 5), or a rat p16 protein (SEQ ID NO: 6).

The p16 protein variant may be resulted from a mutation of at least one amino acid on the amino acid sequence of p16 protein; wherein the at least one amino acid is a hydrophobic residue at a position externally exposed on the three dimensional structure of the protein and is not involved in binding to CDKs (e.g., Cdk4/6). The term "position externally exposed on the three dimensional structure of the protein" may refer to a position in contact with a solvent (e.g., an aqueous solvent) or aqueous environment when the protein is formulated or administered into a body. As used herein, the term "mutation" employed in association with amino acid sequences of p16 may refer to substitution of at least one amino acid with a different amino acid(s), for example, a change from a hydrophobic amino acid(s) to a hydrophilic amino acid(s).

In the amino acid sequence of a wild-type p16 protein, for example, the human p16 protein comprising the amino acid sequence of (SEQ ID NO: 1), the amino acid to undergo such mutation (e.g., substitution) may be at least one selected from the group consisting of tryptophan at position 15 (W15), leucine at position 37 (L37), leucine at position 65 (L65), cysteine at position 72 (C72), leucine at position 78 (L78), valine at position 106 (V106), and leucine at position 113 (L113). Inter alfa, at least one of W15, L65, C72, and L113 are found to have great influence on the solubility of the protein. The mutation (e.g., substitution), therefore, may occur on at least one amino acid residue selected from the group consisting of W15, L65, C72, L113, or any combination thereof, and optionally, may additionally occur on at least one amino acid residue selected from the group consisting of L37, L78, and V106, or any combination thereof.

Amino acid residues to be substituted on the amino acid sequence of SEQ ID NO: 1 are as follows:

```
Wild-Type Human p16
                                         (SEQ ID NO: 1)
MEPAAGSSME PSADWLATAA ARGRVEEVRA LLEAGALPNA

PNSYGRRPIQ VMMMGSARVA ELLLLHGAEP NCADPATLTR

PVHDAAREGF LDTLVVLHRA GARLDVRDAW GRLPVDLAEE

LGHRDVARYL RAAAGGTRGS NHARIDAAEG PSDIPD
```

(possible amino acid residues to undergo substitution are expressed in bold and underlined)

The amino acid to be substituted on the human P16 protein may be at least one selected from the group consisting of tryptophan at position 15(W15), leucine at position 37 (L37), leucine at position 65 (L65), cysteine at position 72 (C72), leucine at position 78 (L78), valine at position 106 (V106), and leucine at position 113 (L113), or any combination thereof. For example, the amino acid to be substituted on the human P16 protein may be at least one selected from the group consisting of W15, L65, C72, and L113, and optionally, may be further selected from the group consisting of L37, L78, and V106.

These amino acids are hydrophobic residues exposed externally on the three-dimensional structure of p16 protein, and may be substituted with hydrophilic amino acids such as negatively or positively charged amino acids or polar amino acids.

By way of example, the human p16 protein variant may be prepared by substituting each of the at least one selected from the group consisting of the above amino acid residues, that is, tryptophan at position 15 (W15), leucine at position 37 (L37), leucine at position 65 (L65), cysteine at position 72 (C72), leucine at position 78 (L78), valine at position 106 (V106), and leucine at position 113 (L113), independently with lysine (K), aspartic acid (D), glutamic acid (E), glutamine (Q), asparagine (N), serine (S), alanine (A), threonine (T), or arginine (R). In order to further increase the solubility of the protein, the variant may necessarily comprise a substitution on cysteine at position 72 (C72) (e.g., substitution with serine (S)). To achieve better improvement in solubility, p16 protein variants having only at least one selected from a substitution of leucine at position 37(L37) (e.g., substitution of leucine at position 37 with aspartic acid (D)), a substitution of leucine at position 78 (L78) (e.g., substitution of leucine at position 78 with serine (S)), and a substitution of valine at position 106 (V106) (e.g., substitution of valine at position 106 with alanine (A)), for example, having all the three substitutions, without any other substitution, may be excluded from the scope of the p16 protein variants in this description.

In detail, the human p16 protein variant may comprise a substitution of at least one selected from the group consisting of tryptophan at position 15 (W15), leucine at position 65 (L65), cysteine at position 72 (C72), and leucine at position 113 (L113), independently with lysine (K), aspartic acid (D), glutamic acid (E), glutamine (Q), asparagine (N), serine (S), alanine (A), threonine (T), or arginine (R); and optionally, further comprise a substitution of at least one selected from the group consisting of leucine at position 37 (L37), leucine at position 78(L78), and valine at position 106 (V106) independently with lysine (K), aspartic acid (D), glutamic acid (E), glutamine (Q), asparagine (N), serine (S), alanine (A), threonine (T), or arginine (R).

For example, the human p16 protein variant may comprise at least one of the following mutations:

a substitution of tryptophan at position 15 (W15) of SEQ ID NO: 1 with lysine (K), arginine (R), aspartic acid (D), glutamic acid (E), glutamine (Q), asparagine (N), or serine (S), a substitution of leucine at position 37 (L37) of SEQ ID NO: 1 with aspartic acid (D), arginine (R), lysine (K), glutamic acid (E), glutamine (Q), serine (S), or asparagine (N), a substitution of leucine at position 65 (L65) of SEQ ID NO: 1 with lysine (K), arginine (R), aspartic acid (D), glutamic acid (E), glutamine (Q), asparagine (N), or serine (S), a substitution of cysteine at position 72 (C72) of SEQ ID NO: 1 with serine (S), a substitution of leucine at position 78 (L78) of SEQ ID NO: 1 with serine (S), arginine (R), lysine (K), aspartic acid (D), glutamic acid (E), glutamine (Q), or asparagine (N), a substitution of valine at position 106 (V106) of SEQ ID NO: 1 with alanine (A), aspartic acid (D), glutamic acid (E), glutamine (Q), or asparagine (N), and a substitution of leucine at position 113 (L113) of SEQ ID NO: 1 with threonine (T), arginine (R), lysine (K), aspartic acid (D), glutamic acid (E), glutamine (Q), asparagine (N), or serine (S).

Out of the amino acid residues, cysteine at position 72 (C72) may act as a factor to decrease the solubility of the protein by forming an inter-chain disulfide bridge with an adjacent amino acid. Therefore, the human p16 protein variant may necessarily comprise a mutation of the cysteine at position 72 (C72) on the amino acid sequence of SEQ ID NO: 1. By way of example, the p16 protein variant may necessarily comprise a substitution of the cysteine at position 72 (C72) of SEQ ID NO: 1 with a different amino acid, e.g., serine (S).

In more detail, the human p16 protein variant may comprise a substitution of the cysteine at position 72 (C72) of SEQ ID NO: 1 with serine (S) either alone or optionally in combination with at least one mutation selected from the group consisting of:

a substitution of tryptophan at position 15 (W15) with lysine (K) arginine (R), aspartic acid (D), glutamic acid (E), glutamine (Q), asparagine (N), or serine (S), a substitution of leucine at position 37 (L37) with aspartic acid (D), arginine (R), lysine (K), glutamic acid (E), glutamine (Q), serine (S), or asparagine (N), a substitution of leucine at position 65 (L65) with lysine (K), arginine (R), aspartic acid (D), glutamic acid (E), glutamine (Q), asparagine (N), or serine (S), a substitution of leucine at position 78 (L78) with serine (S), arginine (R), lysine (K), aspartic acid (D), glutamic acid (E), glutamine (Q), or asparagine (N), a substitution of valine at position 106 (V106) with alanine (A), aspartic acid (D), glutamic acid (E), glutamine (Q), or asparagine (N), and a substitution of leucine at position 113 (L113) with threonine (T), arginine (R), lysine (K), aspartic acid (D), glutamic acid (E), glutamine (Q), asparagine (N), or serine (S).

In a further embodiment, the human p16 protein variant may comprise all of the following: a substitution of tryptophan at position 15 (W15) with lysine (K), arginine (R), aspartic acid (D), glutamic acid (E), glutamine (Q), asparagine (N), or serine (S), a substitution of leucine at position 37(L37) with aspartic acid (D), arginine (R), lysine (K), glutamic acid (E), glutamine (Q), serine (S), or asparagine (N), a substitution of leucine at position 65 (L65) with lysine (K), arginine (R), aspartic acid (D), glutamic acid (E), glutamine (Q), asparagine (N), or serine (S), a substitution of cysteine at position 72(C72) with serine (S), a substitution of leucine at position 78 (L78) with serine (S), arginine (R), lysine (K), aspartic acid (D), glutamic acid (E), glutamine (Q), or asparagine (N), a substitution of valine at position 106 (V106) with alanine (A), aspartic acid (D), glutamic acid (E), glutamine (Q), or asparagine (N), and a substitution of leucine at position 113 (L113) with threonine (T), arginine (R), lysine (K), aspartic acid (D), glutamic acid (E), glutamine (Q), asparagine (N), or serine (S), on the amino acid sequence of SEQ ID NO: 1 (for instance, as in SEQ ID NO: 2).

Human p16 variant (SEQ ID NO: 2)

```
MEPAAGSSME PSADKLATAA ARGRVEEVRA LLEAGADPNA

PNSYGRRPIQ VMMMGSARVA ELLLKHGAEP NSADPATSTR

PVHDAAREGF LDTLVVLHRA GARLDARDAW GRTPVDLAEE

LGHRDVARYL RAAAGGTRGS NHARIDAAEG PSDIPD
```

(substituted amino acid residues are shown in bold and underline)

Alignment of amino acid sequences of p16 proteins from sources other than humans, for example, mouse p16 protein (SEQ ID NO: 5) or rat p16 protein (SEQ ID NO: 6) with the amino acid sequence of human p16 protein shows that residues at positions 7, 29, 57, 64, 70, 98 and 105 (corresponding to positions 15, 37, 65, 72, 78, 106, and 113, respectively, on the amino acid sequence of SEQ ID NO: 1) are exposed externally on the three dimensional structure in contact with an aqueous solvent. Of them, the amino acids at positions 7 (R), 29 (S), 57 (N or S) on the amino acid sequence of SEQ ID NO: 5 or 6 which corresponds, respectively, to tryptophan at position 15(W15), leucine at position 37 (L37), and leucine at position 65 (L65) on the amino acid sequence of the human p16 protein (SEQ ID NO: 1) may not be substituted because they all are hydrophilic. In contrast, the amino acids at positions 64 (C), 70 (F or L), 98 (V) and 105 (L) on the amino acid sequence of SEQ ID NO: 5 or SEQ ID NO: 6, which corresponds, respectively, to cysteine at position 72 (C72), leucine at position 78 (L78), valine at position 106 (V106), and leucine at position 113 (L113) on the amino acid sequence of the human p16 protein (SEQ ID NO: 1) are hydrophobic residues so that at least one of them needs to be substituted by a hydrophilic amino acid, for example, a negatively or positively charged or polar amino acid, to improve the solubility of the p16 protein.

The p16 protein variant may comprise a substitution of at least one of amino acids at positions 64, 70, 98, and 105 on the amino acid sequence of SEQ ID NO: 5 or SEQ ID NO: 6 independently with lysine (K), aspartic acid (D), glutamic acid (E), glutamine (Q), asparagine (N), serine (S), alanine (A), threonine (T), or arginine (R).

For example, the p16 protein variant may comprise at least one selected from the group consisting of:

a substitution of the amino acid at position 64 on the amino acid sequence of SEQ ID NO: 5 or SEQ ID NO: 6 with serine (S), a substitution of the amino acid at position 70 on the amino acid sequence of SEQ ID NO: 5 or SEQ ID NO: 6 with serine (S), arginine (R), lysine (K), aspartic acid (D), glutamic acid (E), glutamine (Q), or asparagine (N), a substitution of the amino acid at position 98 on the amino acid sequence of SEQ ID NO: 5 or SEQ ID NO: 6 with alanine (A), aspartic acid (D), glutamic acid (E), glutamine (Q), or asparagine (N), and a substitution of the amino acid at position 105 on the amino acid sequence of SEQ ID NO: 5 or SEQ ID NO: 6 with threonine (T), arginine (R), lysine (K), aspartic acid (D), glutamic acid (E), glutamine (Q), asparagine (N), or serine (S).

The conjugate may comprise or consist essentially of the amino acid sequence of SEQ ID NO: 34.

The targeting moiety, cleavage site, cell membrane penetrating domain, bioactive substance, and/or hydrophobic peptide or basic peptide (in case the cell membrane penetrating domain is a fusion peptide of a hydrophobic peptide or a basic peptide) may be linked (e.g., covalently) to one another directly (with no linker) or via a linker. The linker may be a peptide liker, and if two or more linkers are used, the linkers may be the same with or different from each other. The peptide linker may include 1 to 100 or 2 to 50 (e.g., 5 to 25, 1 to 10, or 2 to 5) amino acids, and the kinds of the amino acids included in the peptide linker may not have any limitation. For example, the peptide linker may include Gly, Asn and/or Ser residues, or may include neutral amino acids such as Thr and/or Ala. Amino acid sequences suitable for a peptide linker may be well known in the relevant art. The length of the peptide linker may be properly determined so that there is no negative effect on the function of the fusion peptide or conjugate. For example, the peptide linker may include at least one amino acid selected from the group consisting of Gly, Asn, Ser, Thr, and Ala, wherein the total number of the amino acids in the linker may be about 1 to about 100, about 2 to about 50, or about 5 to about 25. The peptide linker may be represented as (GGGGS)n, wherein "n" is an integer from 1 to 10 (e.g., an integer from 2 to 5).

The composition may further include or the conjugate may be administered with a pharmaceutically acceptable carrier. The pharmaceutically acceptable carrier may be any one that is commonly used in formulation of drugs, and may be, but not limited to, at least one selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, mineral oil, and the like. The pharmaceutically composition may further include at least one selected from the group consisting of a diluent, an excipient, a lubricant, a wetting agent, a sweetener, a flavor enhancer, an emulsifying agent, a suspension agent, a preservative, and the like.

The conjugate or the composition may be administered via oral or parenteral route. Parenteral administration may be performed by intravenous injection, subcutaneous injection, muscular injection, intraperitoneal injection, endothelial administration, local administration, intranasal administration, intrapulmonary administration, and/or rectal administration. Since oral administration leads to digestion of proteins or peptides, an active ingredient in the compositions for oral administration must be coated or formulated to prevent digestion in stomach.

In addition, the conjugate may be in a form of solution in oil or an aqueous medium, suspension, syrup, or emulsifying solution form, or may be formulated into a form of an extract, powders, granules, a tablet or a capsule. The cell membrane penetrating conjugate may further include a dispersing agent and/or a stabilizing agent for its formulation.

When the conjugate includes a contrast material as a bioactive substance, the conjugate can be used for visualization of a cell or a cell component (e.g., cytoplasm).

Therefore, also provided is a composition for visualization of a cell (e.g., cytoplasm), which comprises or consists essentially of a fusion protein and a contrast material. Further provided is a method of visualization of a cell including administering a conjugate including a fusion peptide and a contrast material to a subject. The method may further comprise visualizing the cell (e.g., the contrast material in the cell) by any suitable technique.

The subject may be any animal selected from mammals such as primates including human, monkeys, etc., rodents including rats, mice, etc., and the like; a cell, a tissue, or body fluid (e.g., serum) derived (isolated) from the animal (living body); or a culture thereof. The subject may be in need of visualization of a cell. The cell membrane penetrating conjugate including a contrast material may be administered to a subject in need of visualization of a cell, via oral or parenteral route, or administered by being contacted with a cell, tissue, or body fluid isolated from a living body.

The cell to be visualized by the composition or via a method for visualization of a cell may be a normal cell or a cell from lesion, for example, the cell may be a normal cell or a tumor cell (e.g., cancer cell).

Also provided is a method of preparing a fusion protein, including linking (e.g., covalently) a targeting moiety, a cleavage site, and a cell membrane penetrating domain. The linking order is as described herein. The linking step may be performed ex vivo. The linking also may be performed by providing a nucleic acid encoding the fusion peptide, and expressing the nucleic acid in a cell.

Further provided is a method of improving cell membrane penetrability or intracellular delivery efficiency of a bioactive substance, including linking (e.g., covalently) a bioactive substance and a fusion protein comprising a targeting moiety, a cleavage site, and a cell membrane penetrating domain. The linking order is as described herein. The linking step may be performed ex vivo. When the bioactive substance is a peptide or protein, the linking also may be performed by providing a nucleic acid encoding a fusion protein comprising the hydrophobic peptide, basic peptide, and bioactive substance, and expressing the nucleic acid in a cell.

Also provided is a polynucleotide encoding a fusion protein comprising a targeting moiety, a cleavage site, and a cell membrane penetrating domain, a recombinant vector carrying (comprising) the polynucleotide, and a recombinant cell harboring (comprising) the recombinant vector.

The polynucleotide encoding the fusion protein may encode the amino acid sequence of SEQ ID NO: 30. For example, the polynucleotide may comprise the nucleotide sequence of SEQ ID NO: 31.

As used herein, the term "vector" refers to a means for expressing a gene of interest in a host cell, as exemplified by a plasmid vector, a cosmid vector, and a viral vector, such as a bacteriophage vector, an adenovirus vector, a retrovirus vector and an adeno-associated virus vector. The recombinant vector may be constructed from well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by manipulation.

In the recombinant vector, the polynucleotide encoding the protein conjugate may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be constructed typically as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g, a $pL^\lambda$ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as, but not limited to, an f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed. Examples of the prokaryotic host cell available may be at least one selected from the group consisting of *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium*, *Serratia marcescens*, and various *Pseudomonas* species. Eukaryotic host cells to be transformed may be at least one selected from the group consisting of *Saccharomyces cerevisiae*, insect cells, plant cells and animal cells including Sp2/0, CHO (Chinese hamster ovary) K1, CHO DG44, PER.C6, W138, BHK, COS-7, 293, HepG2, Huh7, 3T3, RIN, and MDCK, but not be limited thereto.

Using a method well known in the art, the polynucleotide or a recombinant vector carrying the polynucleotide may be introduced (incorporated) into a host cell. This transformation is carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a (recombinant vector) transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

In the p16 protein variant, the mutated amino acid residues are those that are hydrophobic with external exposure on the three-dimensional structures and have influence on the solubility of the protein in contact with an aqueous solvent. The p16 protein variant is improved in solubility compared to the wild-type because at least one of the externally exposed, hydrophobic residues is substituted by a hydrophilic amino acid, such as an electrically charged amino acid or a polar amino acid. This improvement in protein solubility prevents the p16 protein variant from precipitating upon expression or purification, which leads to increasing the expression of the protein (or the external secretion of the protein). Given an increase in solubility, the p16 protein variant is improved in stability upon formulation and/or storage, and thus can maintain its effective delivery at a high level in vivo upon administration. On the other hand, because the amino acid residues which are or will be mutated exist at positions not involved in binding to Cdk4/6, the p16 protein variant retains affinity for CDKs such as Cdk4/6 at the same level as that of the wild-type p16 and thus functions normally to regulate the cell cycle. As such, the p16 protein variant is advantageous for mass production thanks to improvement in expression level in host cells, and exhibits such high stability that it can be delivered in an elevated, effective amount in vivo upon administration. In addition, the p16 protein variant retains affinity for CDKs sufficiently to regulate the cell cycle and thus to exert inhibitory activity against cancerous infinite cell division. Hence, the p16 protein variant is suggested as an effective and potent anticancer agent.

Therefore, also provided is a pharmaceutical composition comprising a conjugate comprising a fusion protein and a p16 protein variant as an active ingredient. Still further provided is a pharmaceutical composition for the preventing and/or treating cancer, comprising a conjugate comprising a fusion protein and a p16 protein variant as an active ingredient.

Yet still further provided is a method of preventing and/or treating cancer, comprising administering a conjugate comprising a fusion protein and a p16 protein variant to a subject in need thereof. The conjugate comprising a fusion protein and a p16 protein variant may be used in a pharmaceutically effective amount, which amount may be determined by the skilled medical practitioner or medical researcher. This method may further comprise identifying the subject is in need of the prevention and/or treatment of cancer, prior to the administration. The step of identifying may be conducted by any manners and/or methods known to relevant field for identifying whether or not a subject needs the prevention and/or treatment of cancer. For example, the step of identifying may include diagnosing a subject to have a cancer, or identifying a subject who is diagnosed as a cancer patient.

The pharmaceutical composition may further comprise or the conjugate may be administered with a pharmaceutical additive, such as a carrier, a diluent and/or an excipient.

A pharmaceutically acceptable carrier which is typically used for drug formulations may be available for the pharmaceutical composition. Examples of the carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but are not limited thereto. In addition, the pharmaceutical composition may further comprise at least one selected from the group consisting of a diluent, an excipient, a lubricant, a humectant, a sweetener, a flavoring agent, an emulsifier, a suspending agent, and a preservative.

The pharmaceutical composition or the conjugate may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

A dose of the conjugate in the pharmaceutical composition may vary depending on various factors including the type of formulation; the patient's age, weight, and sex; the severity of the disorder being treated; diet; the time of administration; the route of administration; the rate of excretion; and sensitivity. For example, the pharmaceutically effective amount of the active ingredient in the pharmaceutical composition may range in daily dose from 0.001 to 1,000 mg/kg, particularly from 0.01 to 100 mg/kg, and more particularly from 0.1 to 50 mg/kg, but is not limited thereto. The daily dose may be formulated into a unit dose form or distributed into separate dose forms, or may be included within a multiple dose package. As used herein, the term "pharmaceutically effective amount" refers to an amount at which the active ingredient (the conjugate) can exert a desired effect, and may fall within the range set forth above.

The pharmaceutical composition or the conjugate may be formulated into: solutions in oil or aqueous media, suspensions, syrup, emulsions, elixirs, powders, granules, tablets, or capsules, and in this context, a dispersant or a stabilizer may be further employed.

The "subject" may encompass all animals that need the delivery of the bioactive substance (the p16 protein variant) to or into a tumor (cancer) cell, and cells derived (originated or isolated) therefrom. For example, all mammals including primates such as humans and monkeys, and rodents such as mice and rats, cells or tissues derived (originated or isolated) therefrom, and cultures of the cells or tissues may fall into the scope of the subject. To quote an example, the subject may be a patient suffering from cancer, or at risk of cancer, or cancer cells or tissues derived (originated or isolated) from the patient, a culture thereof, or any combination thereof.

The cancer may be related to the aberrant function of p16. The cancer may be a solid cancer or blood cancer. Examples of the cancer include squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, or any combination thereof. The cancer may be primary or metastatic cancer.

With regard to the prophylactic and/or therapeutic effect on cancer, the composition suppresses cancer cells from undergoing migration, invasion and/or metastasis, in addition to inhibiting the growth of primary cancer cells. Therefore, the composition not only inhibits cancer cell growth, but also suppresses the malignancy of cancer due to migration, invasion and metastasis.

As described above, when the conjugate comprises a tumor suppressor such as p16 protein or p16 protein variant as a bioactive substance, it can be used as an anticancer therapeutic protein. In this case, the conjugate has advantages such as low side effects by tumor specific response due to a targeting moiety and more expanded therapeutic effects on various cancers, even on solid cancers which are difficult to treat with pre-existing anticancer agents.

EXAMPLES

Hereafter, the present invention will be described in detail by examples.

The following examples are intended merely to illustrate the invention and are not to be construed to restrict the invention.

Example 1

Preparation of Conjugate
"D(EGFR)-M9R-MTS-NLS-p16M7"

A conjugate precursor of 'N-terminus-(NdeI)-His6-TEV-D(EGFR)-M9R-MTS-NLS-p16(M7)-STOPx2-(XhoI)-C-terminus', which has EGFR DARPin (D(EGFR); SEQ ID NO: 7) as a targeting moiety, M9R (SEQ ID NO: 26) as a cleavage site, MTS(SEQ ID NO: 11)-NLS(SEQ ID NO: 16) fusion peptide as a cell membrane penetrating domain, and p16 variant (p16M7); SEQ ID NO: 2) as a bioactive substance, was prepared (amino acid sequence: SEQ ID NO: 36; nucleotide sequence: SEQ ID NO: 37). 'TEV sequence', which is a peptide derived from tobacco etch virus protease (Tev), was used as a cleavage position for separating is His tag used for purification.

The amino acid sequences and nucleotide sequences of each component used for preparation of the conjugate are summarized in Table 2:

| component | Amino acid sequence (SEQ ID NO: 36) | Nucleotide sequence (SEQ ID NO: 37) |
|---|---|---|
| TEV | ENLYFQGS (SEQ ID NO: 77) | GAAAACCTGTATTTTCAGGGATCC (SEQ ID NO: 78) |
| Linker | GSGS (SEQ ID NO: 79) | GGCAGCGGCAGC (SEQ ID NO: 80) |
| EGFR DARPin [D(EGFR)] | DLGKKLLEAARAGQDDEVRILMANGA DVNADDTWGWTPLHLAAYQGHLEIVE VLLKNGADVNAYDYIGWTPLHLAADG HLEIVEVLLKNGADVNASDYIGDTPLHL AAHNGHLEIVEVLLKHGADVNAQDKF GKTAFDISIDNGNEDLAEILQ (SEQ ID NO: 7) | GATCTGGGCAAAAAACTGCTGGAAGCGGCG CGCGCGGGCCAGGATGATGAAGTGCGCATTCT GATGGCGAATGGTGCGGATGTTAACGCGGAC GATACCTGGGGCTGGACCCCACTGCATCTGG CCGCGTATCAGGGTCACCTGGAAATCGTGGA GGTGCTGCTGAAAAACGGCGCGGATGTGAAC GCGTATGATTATATTGGCTGGACCCCGCTGC ATCTGGCGGCGGATGGCCATCTGGAAATTGT GGAAGTGCTGCTGAAAAACGGCGCTGATGTT AATGCTAGCGATTATATTGGCGATACGCCGC TGCACCTGGCAGCGCATAACGGCCATCTGGA GATTGTTGAAGTTCTGCTGAAGCATGGCGCC GATGTGAATGCGCAGGATAAATTTGGCAAAA CCGCGTTTGATATTAGCATTGATAACGGCAA CGAAGATCTGGCGGAAATTCTGCAG (SEQ ID NO: 81) |
| M9R (MMP9) | SGKIPRTLTA (SEQ ID NO: 26) | AGCGGCAAAATTCCGCGTACCCTGACCGCG (SEQ ID NO: 82) |
| Linker | GS | GGCAGC |
| MTS | AAVALLPAVLLALLAP (SEQ ID NO: 11) | GCCGCGGTAGCGCTGCTCCCGGCGGTCCTGC TGGCCTTGCTGGCGCCC (SEQ ID NO: 83) |
| Linker | GS | GGCAGC |

| component | Amino acid sequence (SEQ ID NO: 36) | Nucleotide sequence (SEQ ID NO: 37) |
|---|---|---|
| NLS | KKKRK (SEQ ID NO: 16) | AAAAAGAAGAGAAAG (SEQ ID NO: 84) |
| Linker | GS | GGCAGC |
| p16M7 (wherein the mutated positions are underlined) | MEPAAGSSMEPSADKLATAAARGRVE EVRALLEAGADPNAPNSYGRRPIQVMM MGSARVAELLLKHGAEPNSADPATSTR PVHDAAREGFLDTLVVLHRAGARLDA RDAWGRTPVDLAEELGHRDVARYLRA AGGTRGSNHARIDAAEGPSDIPD (SEQ ID NO: 2) | ATGGAACCGGCTGCTGGCAGCTCTATGGAAC CGTCTGCTGACAAACTGGCTACCGCTGCTGCT CGTGGTCGTGTTGAAGAAGTTCGTGCTCTGCT GGAAGCTGGTGCTGATCCGAACGCTCCGAAC TCTTACGGTCGTCGTCCGATCCAGGTTATGAT GATGGGCAGCGCTCGTGTTGCTGAACTGCTG CTGAAACACGGTGCTGAACCGAACAGCGCTG ACCCGGCTACCAGCACCCGTCCGGTTCACGA CGCTGCTCGTGAAGGTTTCCTGGACACCCTG GTTGTTCTGCACCGTGCTGGTGCTCGTCTGGA CGCGCGTGACGCTTGGGGTCGTACCCCGGTT GACCTGGCTGAAGAACTGGGTCACCGTGACG TTGCTCGTTACCTGCGTGCTGCTGCTGGTGGT ACCCGTGGCAGCAACCACGCTCGTATCGACG CTGCTGAAGGTCCGTCTGACATCCCGGAC (SEQ ID NO: 85) |

An expression (recombinant) vector comprising the nucleotide sequence of SEQ ID NO: 37 was prepared, to produce a conjugate comprising 'targeting moiety[D (EGFR)]-cleavage site(M9R)-fusion peptide[(MTS)-(NLS)]-tumor suppressor[p16M7]' in order from the N-terminus to the C-terminus (conjugate "D(EGFR)-M9R-MTS-NLS-p16M7"). In addition, for comparison to the conjugate, expression vectors for producing conjugate which lacks one or more component from the conjugate "D(EGFR)-M9R-MTS-NLS-p16M7" were prepared.

The expression vectors were prepared by Geno Tech Corp. (Korea), and pET-21b(+)(EMD Biosciences) was used as a vector for protein overexpression. The insert DNA fragment (SEQ ID NO: 37) contains a restriction site of NdeI at 5' terminus and a restriction site of XhoI at 3' terminus, to be inserted into NdeI-XhoI cleavage site of the pET21b(+) vector.

The prepared conjugate was referred as D(EGFR)-M9R-MTS-NLS-p16M7.

Example 2

Purification of D(EGFR)-M9R-MTS-NLS-p16M7

The D(EGFR)-M9R-MTS-NLS-p16M7 was purified.

The vector provided in Example 1 was transfected into *E. coli* BL21(DE3) cell and expressed, to produce the conjugate. The transfected cells were cultured in LB media. When the optical density (O.D.) value of absorbance at 600 nm reached 0.5, 1 mM of IPTG (isopropyl-β-D-thio-galactoside) was added to the cell culture, which was further cultured at 18° C. for 16 hours. The obtained cultured cells were sonicated in the presence of 20 mM Tris-HCl buffer solution (pH 7.4) supplemented with 10% (w/v) glycerol and 0.25M NaCl, and centrifuged at 10,000 g, to obtain a supernatant. The obtained supernatant was applied to Ni$^{2+}$-NTA superflow column (Qiagen) which was equilibrated with the buffer solution. The column was washed with a washing buffer (20 mM Tris-HCl, pH 7.4, 10% glycerol. and 1 M NaCl) in the amount of 5-fold of the column volume, and then treated with an eluting buffer (20 mM Tris-HCl, pH 7.4, 10% glycerol, 0.25 M NaCl and 0.2M imidazole), to elute the conjugate. The fractions including the conjugate were collected and salts comprised in the fractions were removed using Amicon Ultra-15 Centrifugal Filter (Milipore), to concentrate and purify the conjugate. The concentration of the purified conjugate was measured using BSA as a standard substance.

The obtained results are summarized in Table 3:

TABLE 3

| Purity (%) | Elution Time (min) | Molecular weight (kDa, calculated) | Molecular weight (Mw$_{app}$, kDa) |
|---|---|---|---|
| 96.57 | 17.066 | 40.12 | 115.31 |

FIG. 1 shows immunoblotting results obtained by SDS-PAGE, which indicate the expression and purification of the conjugates expressed by the vectors prepared in Example 1.

Example 3

Tumor Cell Targeting of the Conjugate

To examine the tumor cell targeting ability of the targeting moiety [D(EGFR)] of the conjugate purified in Example 2, a targeting test was conducted using a A431 cell line.

To examine the targeting ability of proteins, Erbitux (EGFR antibody; Merck Serono, Germany; used as a positive control), a targeting moiety [D(EGFR); Darpin which targets EGFR] (SEQ ID NO: 7), and Darpin (as a negative control; Mock Darpin having no binding target; GSDLGK-KLLEAARAGQDDEVRILMANGADVNAEDKVGLT-PLHLAAMNDHLEIVEVLL KNGADVNAIDAIGETPL-HLVAMYGHLEIVEVLLKHGADVNAQDKFGKTAFDIS IDNGNE DLAEILQKLN; SEQ ID NO: 43) were provided and A431 cells (ATCC; 2×10$^5$ cells/well) were cultured in 8 well imaging chamber for 20 hours, and treated with each of the provided proteins at the amount of 7.5 or 15 ug/ml for one hour. Thereafter, the medium was exchanged with FBS-containing medium. Imaging was conducted sequentially and the obtained images were analyzed using image J (JAVA).

The imaging and image analysis were conducted as follows. For imaging, a confocal microscope (LSM710, Carl Zeiss) and Live cell Chamber (LCI; Live cell instrument)

were used. Four average imaging was conducted using an ×63 objective lens (ZEISS Plan-Apochromat 63×/1.4 oli DIC) at a resolution of 1024×1024. Digital zoom (1- to 2.5-fold) and a range indicator were used for gain/offset control. The imaging was conducted with LCI setting under the conditions of 37° C. and 5% $CO_2$, and maximum imaging tine were set as 2.5 hours. The obtained cell images were analyzed using Zen (carl zeiss) and image J (public), and plotted using Excel (Microsoft) and Sigmaplot. Image J was of a version equipped with 'UCSD Confocal Microscopy Plugins and MBF ImageJ for Microscopy Collection by Tony Collins'.

Figure 2:
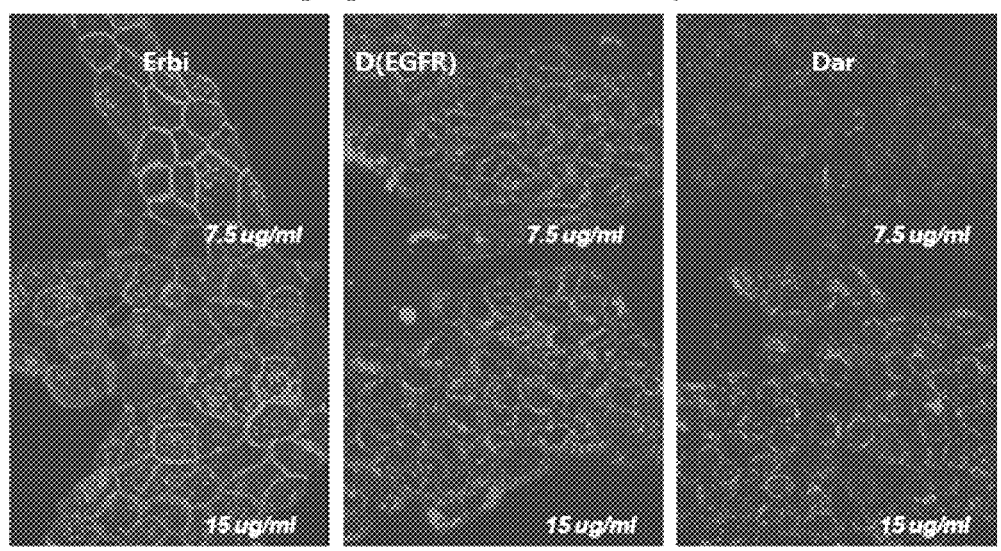
FIG. 2 is a set of fluorescent images showing the cancer cell targeting of an 'anti-EGFR DARPin-M9R-MTS-NLS-p16M7' conjugate.

The obtained results are shown in FIG. 2. As shown in FIG. 2, the targeting moiety [D(EGFR)](middle) exhibits excellent binding ability to EGFR present in A431 at the similar level to the positive control Erbitux(left), whereas the negative control Darpin showed little binding ability.

Example 4

Cell Cycle Arrest Test

A vector containing a gene encoding 'p16M7' or 'p16WT' (wild-type) was transfected into A431 cells (ATCC) by liposomal transfection method using Lipofectamine 2000 (Invitrogen) (see Example 1). The transfection was performed according to a manual provided by Invitrogen. 24 hours after the transfection, the medium was exchanged with a fresh medium. At 24 hours 48 hours thereafter, DNA contents were measured by FACS.

Figure 3:
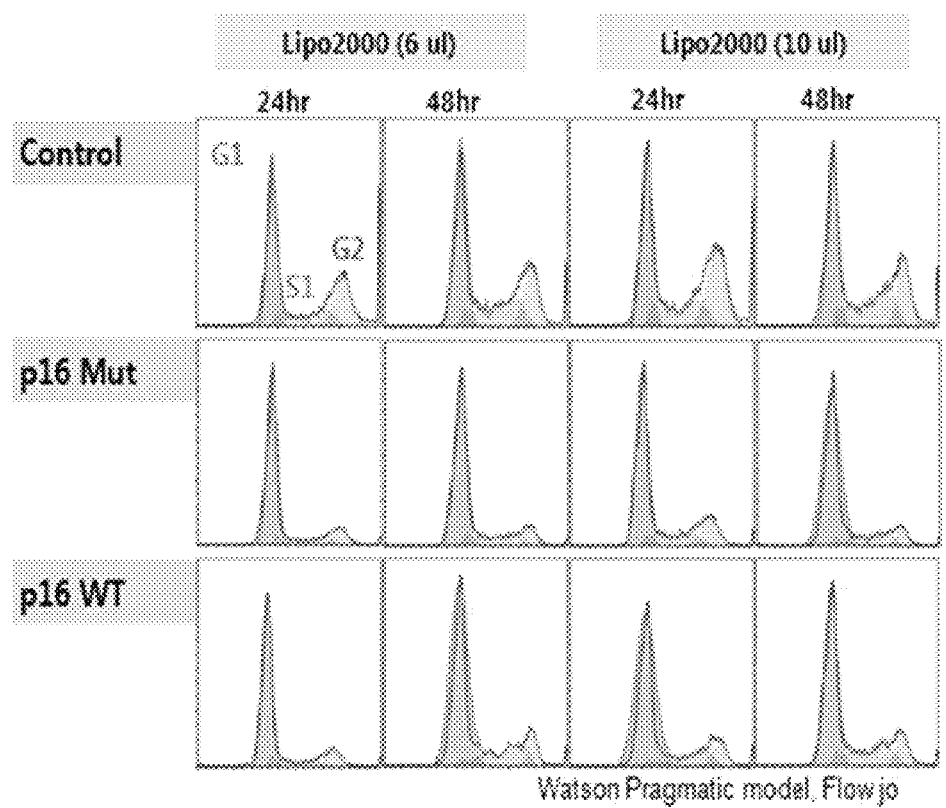
FIG. 3 is a set of graphs showing the cell cycle arrest effects of p16M7 and p16WT proteins (X axis: PI area, Y axis: cell population (event); wherein for labeling, pEGFP-C2 vector was used for p16WT and p16M7; control: enhanced green fluorescent protein (EGFP) used only).
Figure 4:
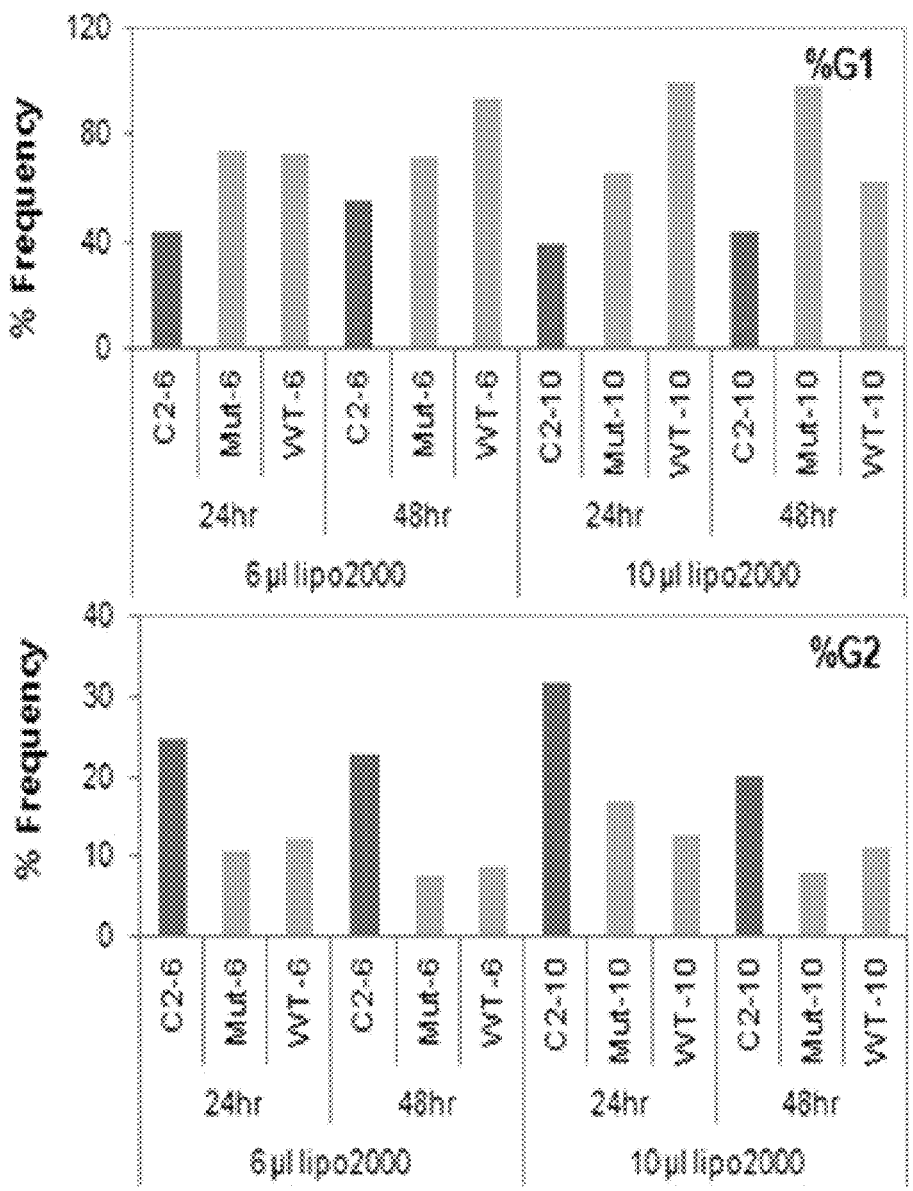
FIG. 4 provides two graphs quantitatively showing the cell cycle arrest of FIG. 3.

After transfecting the p16M7 gene or p16WT gene into cells using Lipo2000, the presence of cell cycle arrest was observed. All experiments were performed three times, and the average values of the obtained results were shown in FIGS. 3 and 4. In FIG. 3, X axis refers to PI (Propidium iodide) area, which shows cell viability by signal intensity from nucleic acid staining, and Y axis refers to cell population (event). For labeling, pEGFP-C2 vector (Clontech) for p16WT and p16M7 (indicated as "p16 Mut" in FIG. 3). The control used enhanced green fluorescent protein (EGFP) only, meaning it did not contain a gene encoding 'p16M7' or 'p16WT'. FIG. 4 contains graphs quantitatively showing the degree of cell cycle arrest of FIG. 3, wherein "% frequency" of Y axis refers to a value of cell population obtained through Flow jo software, each symbol in X axis refers to the follows: C2-6: using EGFP only (6 ul), C2-10: using EGFP only (10 ul), Mut: using p16M7 (6 ul or 10 ul) and WT: using p16WT (6 ul or 10 ul). As shown in FIGS. 3 and 4, p16M7 has improved properties compared to p16WT, with maintaining the cell cycle arrest effect.

Example 5

Tumor Cell Proliferation Inhibition by the Conjugate

The anticancer effect of the p16M7 conjugate of Example 2 was examined using human breast cancer cell lines HCC1143 (ATCC) and MDA-MB-231 (ATCC), and a human lung cancer cell line A549(ATCC).

Each cell line was seeded on 10% (v/v) FBS-containing RPMI medium (Gibco) or DMEM medium (Gibco) in 96-well plate at the amount of $1 \times 10^3$ cells/well. On the next day, each well was treated with each of various conjugates comprising p16M7 (tMTS-NLS-p16M7, TATp16M7, MTS-NLS-p16M7, NLS-NLS-p16M7, and TEV-MTS-NLS-p16M7) with concentration of 0, 2.5, 5, 10, or 20 uM at the amount of 100 uL per a well (see FIG. 5), or with concentration of 0, 2, 4, 6, 8, 10 or 12 uM at the amount of 100 uL per a well (see FIG. 6), and thereafter, cultured in CO2 incubator under the conditions of 37° C. and 5% CO2 for 72 hours. For comparison, PD0332991 (Selleckchem) and buffer (RPMI 1640, Gibco), each of which has the concentration of 0, 2, 4, 6, 8, 10 or 12 uM, were used at the amount of 100 uL per a well, respectively, and the same experiment was performed as above. In the conjugate, tMTS refers to 'AVLLALLAA' (SEQ ID NO: 14), NLS refers to "KKKRK" (SEQ ID NO: 16), and TAT refers to 'RKKRRQRRR' (SEQ ID NO: 38). 80 uL of CellTiter-Glo reagent (Promega) was added to each well, and then the luminescence was measured by EnVision Multilabel Reader (PerkinElmer) to measure the cell viability (%).

Figure 5:
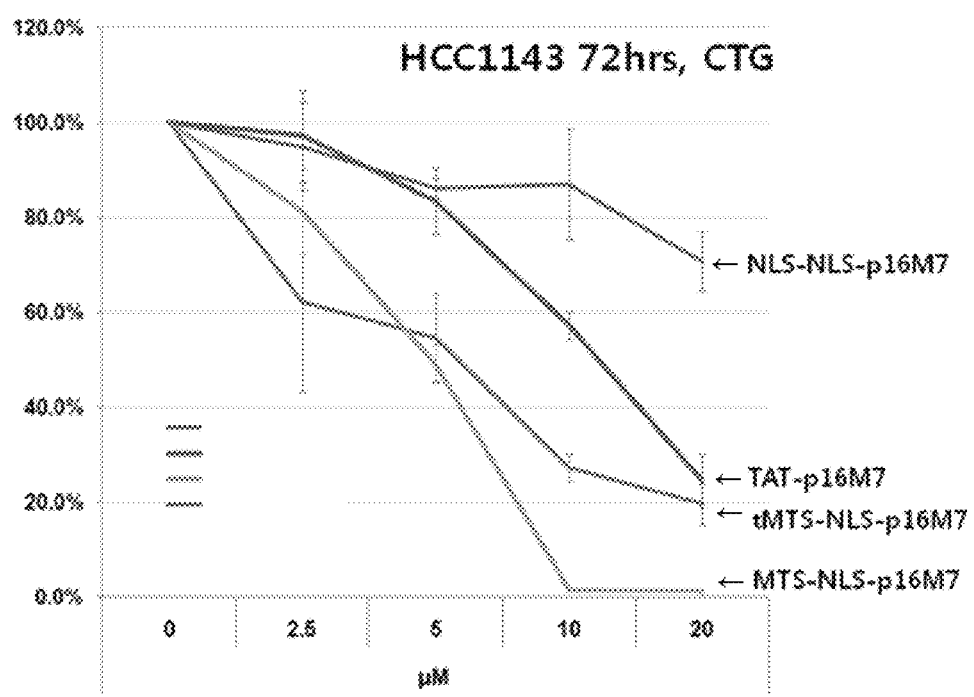
FIG. 5 is a graph showing the relative cell viability of HCC1143 cell lines treated with 'NLS-NLS-p16M7', 'tMTS-NLS-p16M7', 'MTS-NLS-p16M7', and 'TAT-p16M7' conjugates, respectively.
Figure 6:
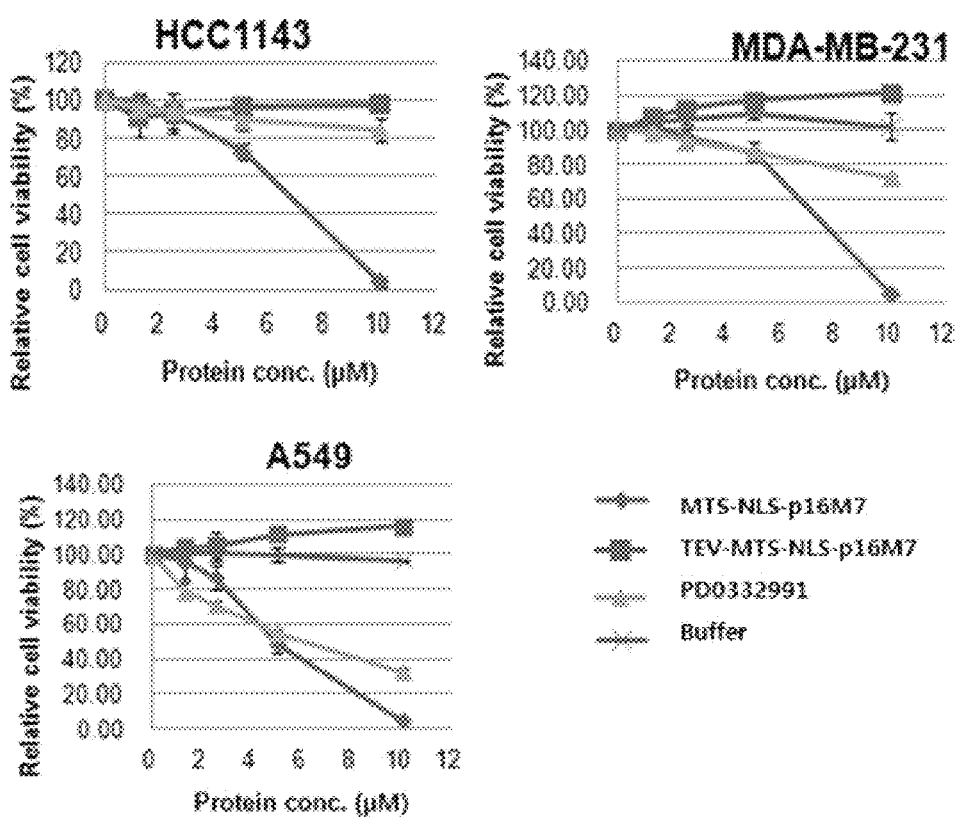
FIG. 6 provides three graphs showing the relative cell viability of various cell lines treated with a 'MTS-NLS-p16M7' or 'TEV-MTS-NLS-p16M7' conjugate or with PD0332991.

All experiments were performed three times, and the average values of the obtained results are shown in FIGS. 5 and 6. As shown in FIGS. 5 and 6, MTS-NLS-p16M7 conjugate exhibits most excellent transferring effect in all the HCC1143, MDA-MB-231, and A549 cells. These results indicate that the conjugate comprising MTS-NLS fusion peptide exhibits most excellent intracellular transferring effect.

Example 6

Anticancer Effect of the Conjugate in MDA-MB-231 Xenograft Mouse Model

To examine the anticancer effect of the conjugate of Example 2, a xenograft mouse model was employed. The xenograft mouse model was prepared by an intravenous injection of intractable breast cancer cell line MDA-MB-231 into breast tissue of 6-week old BALB/c nude mouse to form a tumor tissue.

In particular, $8 \times 10^6$ cells (in 0.08 ml of PBS with matrigel) of MDA-MB-231 (ATCC) were intravenously injected into tail of 6-week old BALB/c nude mouse to prepare a xenograft mouse model (Orthotopic mouse model). When the tumor size reaches $10^4$ $mm^3$, the xenograft mouse model was used in the following experiment.

Each of buffer (RPMI 1640, Gibco; 0.1 ml/mouse), D(EGFR)-M9R-MTS-NLS-p16M7 (75 uM/0.1 ml/mouse), D(EGFR)-M9R-p16M7 (SEQ ID NO: 7-SEQ ID NO: 26-SEQ ID NO: 2) (75 uM/0.1 ml/mouse), D(EGFR) (SEQ ID NO: 7) (75 uM/0.1 ml/mouse), and PD0332991 (Selleckchem) (150 mg/kg) was administered to the tumor tissue of the xenograft mouse model once a day, and then the tumor size was observed (n=10).

Figure 7:
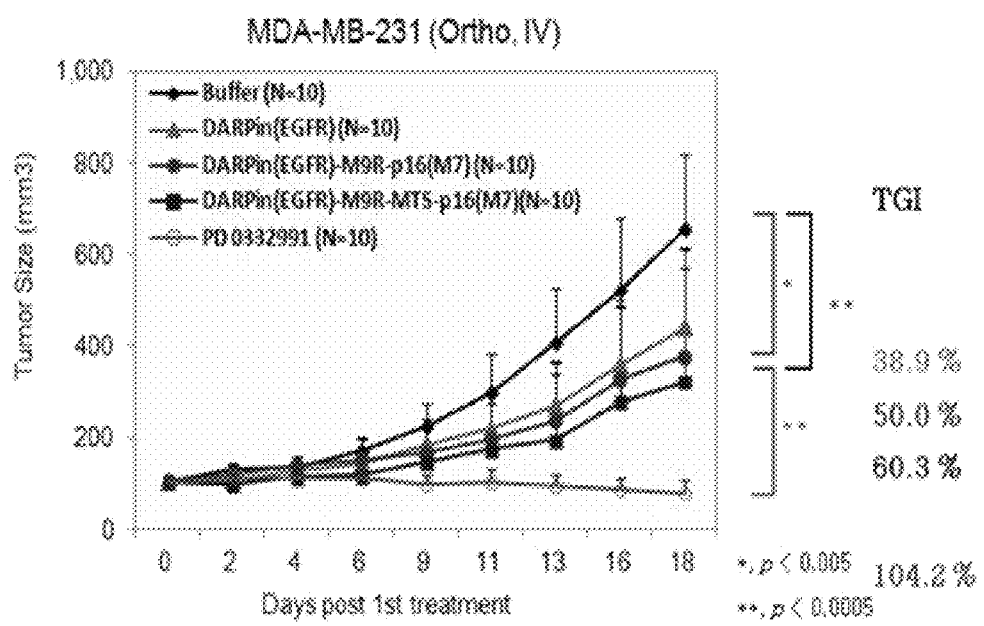
FIG. 7 is a graph showing a tumor size after treatment with an 'anti-EGFR DARPin-M9R-MTS-NLS-p16M7' (indicated 'anti-EGFR DARPin-M9R-MTS-p16M7' in this figure) or 'anti-EGFR DARPin-M9R-p16 conjugate or with PD0332991.

The obtained results are shown in FIG. 7, and the degree (%) of tumor size reduction (tumor growth inhibition; TGI) compared to the buffer administered group calculated from the results of FIG. 7 was shown in Table 4:

TABLE 4

| | degree (%) of tumor size reduction ([(tumor size of buffer administered group-tumor size of each conjugate administered group)/tumor size of buffer administered group]*100) |
|---|---|
| Buffer | 0% |
| D(EGFR) | 38.9% |
| D(EGFR)-M9R-p16M7 | 50.0% |
| D(EGFR)-M9R-MTS-NLS-p16M7 | 60.3% |

As shown in FIG. 7 and Table 4, the group administered with the conjugate "D(EGFR)-M9R-MTS-NLS-p16M7" exhibits about 21.4% increased anticancer effect compared to the control [Darpin(EGFR)], and about 60% or more increased anticancer effect compared to the buffer administered group. These results suggest that MMP9 (M9R) in the conjugate "D(EGFR)-M9R-MTS-NLS-p16M7" can effectively be cleaved in an animal body (in vivo) to release the end product "MTS-NLS-p16M7", which is successfully delivered into a cancer cell.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fusion protein comprising a targeting moiety, a cleavage site, and a cell membrane penetrating domain, wherein
the targeting moiety is an antibody or antigen-binding fragment thereof, a designed ankyrin repeat protein (DARPin), or a combination thereof, that specifically binds an ErbB family receptor tyrosine kinase protein;

the cleavage site is a recognition site of a matrix metalloproteinase (MMP), cathepsin, or urokinase-type plasminogen activator (uPA); and the cell membrane penetrating domain is a membrane-translocation sequence, a macromolecule intracellular transduction domain, a fusion peptide comprising a hydrophobic peptide and a basic peptide, or a combination thereof.

2. The fusion protein of claim 1, wherein the targeting moiety is an antibody or antigen-binding fragment thereof, a DARPin, or a combination thereof, that specifically binds epidermal growth factor receptor (EGFR).

3. The fusion protein of claim 2, wherein the targeting moiety is at least one anti-EGFR DARPin selected from SEQ ID NOs: 7 to 10.

4. The fusion protein of claim 1, wherein the cell membrane penetrating domain comprises SEQ ID NO: 11, SEQ ID NO: 12, SEQ ID NO: 13, SEQ ID NO: 14, SEQ ID NO: 15, SEQ ID NO: 38, or a combination thereof.

5. The fusion protein of claim 1, wherein the cell membrane penetrating domain is a fusion peptide comprising a hydrophobic peptide and a basic peptide, wherein the hydrophobic peptide comprises a total of about 5 to about 40 amino acids of which 70% or more are hydrophobic amino acids, and each hydrophobic amino acid is independently selected from the group consisting of glycine, alanine, valine, leucine, isoleucine, methionine, proline, tryptophan, and phenylalanine, and the basic peptide consists of a basic peptide unit consisting of about 1 to about 6 basic amino acids or a repeat comprising 2 to 6 basic peptide units.

6. The fusion protein of claim 5, wherein the hydrophobic peptide comprises SEQ ID NO: 11, SEQ ID NO: 12, SEQ ID NO: 13, SEQ ID NO: 14, or SEQ ID NO: 15, or a combination thereof.

7. The fusion protein of claim 5, wherein the basic peptide comprises SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

8. The fusion protein of claim 5, wherein the basic peptide is linked to the C-terminus of the hydrophobic peptide.

9. The fusion protein of claim 1, comprising SEQ ID NO: 30.

10. A pharmaceutical composition comprising the fusion protein of claim 1.

11. A conjugate comprising the fusion protein of claim 1 and a bioactive molecule, wherein the bioactive molecule is a protein, a peptide, a nucleic acid, a small-molecule drug, or a combination thereof.

12. The conjugate of claim 11, wherein the bioactive molecule is a p16 protein variant comprising SEQ ID NO: 1 with an amino acid substitution at one or more of positions 15 (W15), 37 (L37), 65 (L65), 72 (C72), 78 (L78), 106 (V106), and 113 (L113) independently with lysine (K), aspartic acid (D), glutamic acid (E), glutamine (Q), asparagine (N), serine (S), alanine (A), threonine (T), or arginine (R).

13. The conjugate of claim 12, wherein the amino acid substitution is at least one selected from the group consisting of:
- a substitution of tryptophan at position 15 (W15) with lysine (K), arginine (R), aspartic acid (D), glutamic acid (E), glutamine (Q), asparagine (N), or serine (S),
- a substitution of leucine at position 37 (L37) with aspartic acid (D), arginine (R), lysine (K), glutamic acid (E), glutamine (Q), serine (S), or asparagine (N),
- a substitution of leucine at position 65 (L65) with lysine (K), arginine (R), aspartic acid (D), glutamic acid (E), glutamine (Q), asparagine (N), or serine (S),
- a substitution of cysteine at position 72 (C72) with serine (S),
- a substitution of leucine at position 78 (L78) with serine (S), arginine (R), lysine (K), aspartic acid (D), glutamic acid (E), glutamine (Q), or asparagine (N),
- a substitution of valine at position 106 (V106) with alanine (A), aspartic acid (D), glutamic acid (E), glutamine (Q), or asparagine (N), and
- a substitution of leucine at position 113 (L113) with threonine (T), arginine (R), lysine (K), aspartic acid (D), glutamic acid (E), glutamine (Q), asparagine (N), or serine (S).

14. The conjugate of claim 12, wherein the p16 protein variant comprises SEQ ID NO: 2.

15. A method of intracellular delivery of a bioactive molecule in a subject, the method comprising administering the conjugate of claim 11 to the subject.

16. The method of claim 15, wherein the bioactive molecule is a p16 protein variant comprising SEQ ID NO: 1 with an amino acid substitution at one or more of positions 15 (W15), 37 (L37), 65 (L65), 72 (C72), 78 (L78), 106 (V106), and 113 (L113) independently with lysine (K), aspartic acid (D), glutamic acid (E), glutamine (Q), asparagine (N), serine (S), alanine (A), threonine (T), or arginine (R).

17. The method of claim 16, wherein the amino acid substitution is at least one selected from the group consisting of:
- a substitution of tryptophan at position 15 (W15) with lysine (K), arginine (R), aspartic acid (D), glutamic acid (E), glutamine (Q), asparagine (N), or serine (S),
- a substitution of leucine at position 37 (L37) with aspartic acid (D), arginine (R), lysine (K), glutamic acid (E), glutamine (Q), serine (S), or asparagine (N),
- a substitution of leucine at position 65 (L65) with lysine (K), arginine (R), aspartic acid (D), glutamic acid (E), glutamine (Q), asparagine (N), or serine (S),
- a substitution of cysteine at position 72 (C72) with serine (S),
- a substitution of leucine at position 78 (L78) with serine (S), arginine (R), lysine (K), aspartic acid (D), glutamic acid (E), glutamine (Q), or asparagine (N),
- a substitution of valine at position 106 (V106) with alanine (A), aspartic acid (D), glutamic acid (E), glutamine (Q), or asparagine (N), and
- a substitution of leucine at position 113 (L113) with threonine (T), arginine (R), lysine (K), aspartic acid (D), glutamic acid (E), glutamine (Q), asparagine (N), or serine (S).

18. The method of claim 16, wherein the p16 protein variant comprises SEQ ID NO: 2.

19. A method of treating breast cancer in a subject, comprising administering the conjugate of claim 12 to a subject in need of breast cancer treatment.

20. The method of claim 19, wherein the amino acid substitution is at least one selected from the group consisting of:
- a substitution of tryptophan at position 15 (W15) with lysine (K), arginine (R), aspartic acid (D), glutamic acid (E), glutamine (Q), asparagine (N), or serine (S),
- a substitution of leucine at position 37 (L37) with aspartic acid (D), arginine (R), lysine (K), glutamic acid (E), glutamine (Q), serine (S), or asparagine (N),
- a substitution of leucine at position 65 (L65) with lysine (K), arginine (R), aspartic acid (D), glutamic acid (E), glutamine (Q), asparagine (N), or serine (S),
- a substitution of cysteine at position 72 (C72) with serine (S),
- a substitution of leucine at position 78 (L78) with serine (S), arginine (R), lysine (K), aspartic acid (D), glutamic acid (E), glutamine (Q), or asparagine (N),
- a substitution of valine at position 106 (V106) with alanine (A), aspartic acid (D), glutamic acid (E), glutamine (Q), or asparagine (N), and
- a substitution of leucine at position 113 (L113) with threonine (T), arginine (R), lysine (K), aspartic acid (D), glutamic acid (E), glutamine (Q), asparagine (N), or serine (S).

21. A polynucleotide encoding a fusion protein of claim 1, optionally in a vector.

22. A cell comprising the polynucleotide of claim 21.

* * * * *